(12) United States Patent
Brawn

(10) Patent No.: US 11,957,930 B2
(45) Date of Patent: Apr. 16, 2024

(54) METHOD AND APPARATUS FOR TOOTH-MOVEMENT REGULATION

(71) Applicant: LLLT TECHNOLOGIES SA, Anieres (CH)

(72) Inventor: Peter Robert Brawn, Vancouver (CA)

(73) Assignee: LLLT Technologies SA, Geneva (CH)

( * ) Notice: Subject to any disclaimer, the term of this patent is extended or adjusted under 35 U.S.C. 154(b) by 32 days.

(21) Appl. No.: 17/555,073

(22) Filed: Dec. 17, 2021

(65) Prior Publication Data

US 2022/0105357 A1 Apr. 7, 2022

Related U.S. Application Data

(63) Continuation of application No. 16/428,773, filed on May 31, 2019, now abandoned, which is a continuation of application No. 15/856,831, filed on Dec. 28, 2017, now abandoned, which is a continuation of application No. 15/454,763, filed on Mar. 9, 2017, now abandoned, which is a continuation of application No. 13/826,383, filed on Mar. 14, 2013, now abandoned, which is a continuation of application No. PCT/CA2011/050639, filed on Oct. 12, 2011.

(Continued)

(51) Int. Cl.
| | |
|---|---|
| *A61N 5/06* | (2006.01) |
| *A61C 7/00* | (2006.01) |
| *A61C 7/08* | (2006.01) |
| *A61C 19/00* | (2006.01) |
| *A61N 5/067* | (2006.01) |

(52) U.S. Cl.
CPC .............. *A61N 5/0603* (2013.01); *A61C 7/00* (2013.01); *A61C 7/08* (2013.01); *A61N 5/0601* (2013.01); *A61N 5/0613* (2013.01); *A61C 19/00* (2013.01); *A61N 2005/0606* (2013.01); *A61N 2005/0628* (2013.01); *A61N 2005/0647* (2013.01); *A61N 2005/0651* (2013.01); *A61N 2005/0659* (2013.01); *A61N 2005/0662* (2013.01); *A61N 2005/0663* (2013.01); *A61N 5/067* (2021.08)

(58) Field of Classification Search
None
See application file for complete search history.

(56) References Cited

U.S. PATENT DOCUMENTS 6,063,108 A * 5/2000 Salansky .............. A61N 5/0616
606/9
6,471,716 B1 * 10/2002 Pecukonis .............. A61C 19/06
606/9

(Continued)

*Primary Examiner* — Carl H Layno
*Assistant Examiner* — Manolis Pahakis
(74) *Attorney, Agent, or Firm* — Levine Bagade Han LLP

(57) ABSTRACT

Methods are provided for regulating tooth movement and for maintaining or improving tissue health using heavy forces. Such methods comprise allowing a heavy force to be exerted on one or more teeth of a patient in need thereon and administering an effective amount of light to the maxillary or mandibular alveolar bone of the patient, wherein the light is administered before, during, or after the heavy force is exerted. The light can have a wavelength in the range of about 585 nm to about 665 nm, or about 815 nm to about 895 nm. An apparatus useful for providing light therapy is also provided.

25 Claims, 25 Drawing Sheets

Related U.S. Application Data

(60) Provisional application No. 61/392,809, filed on Oct. 13, 2010.

(56) References Cited

U.S. PATENT DOCUMENTS

| | | | | |
|---|---|---|---|---|
| 2003/0009205 A1* | 1/2003 | Biel | ............... | A61N 5/0601 |
| | | | | 607/88 |
| 2004/0193236 A1* | 9/2004 | Altshuler | ............ | A61B 18/203 |
| | | | | 607/88 |
| 2006/0200212 A1* | 9/2006 | Brawn | ............... | A61N 5/0622 |
| | | | | 607/88 |
| 2007/0248930 A1* | 10/2007 | Brawn | ............... | A61N 5/0613 |
| | | | | 433/25 |

* cited by examiner

METHOD AND APPARATUS FOR TOOTH-MOVEMENT REGULATION

CROSS-REFERENCE TO RELATED APPLICATIONS

This application is a continuation of U.S. patent application Ser. No. 16/428,773 filed May 31, 2019, now abandoned, which is a continuation of U.S. patent application Ser. No. 15/856,831, filed Dec. 28, 2017, now abandoned, which is a continuation of U.S. patent application Ser. No. 15/454,763 filed Mar. 9, 2017, now abandoned, which is a continuation of U.S. patent application Ser. No. 13/826,383 filed Mar. 14, 2013, now abandoned, which is a continuation of and claims priority to International Patent Application No. PCT/CA2011/050639 filed Oct. 12, 2011, which claims a benefit of priority to U.S. Provisional Patent Application No. 61/392,809, filed Oct. 13, 2010, the disclosure of each of which is incorporated by reference herein in its entirety.

FIELD OF INVENTION

This invention relates to methods and apparatuses useful in orthodontics, and in particular to methods and apparatuses useful for regulating tooth movement; reducing, preventing or minimizing tooth-root resorption; reducing bone resorption or inflammatory dentin resorption or cementum resorption of the tooth root or periodontium; preventing or minimizing inflammation of tissue surrounding one or more teeth upon which heavy forces are or were exerted; or regenerating maxillary or mandibular alveolar bone, using heavy forces.

BACKGROUND

Orthodontics involves the movement of teeth through bone. By applying pressure to a tooth, bone can be broken down at a leading edge of the tooth to facilitate tooth movement. New bone is then created at a trailing edge of the tooth. Bone is resorbed in (e.g., broken down) in areas of pressure between a tooth root and periodontium, and bone is deposited (created) in areas of tension between a tooth root and periodontium. Pressure can cause resorption and tension can cause deposition regardless of where they occur along a tooth root surface. Movement of teeth through bone is slow based on the speed of the remodeling process while teeth are undergoing conventional orthodontic treatment, thereby necessitating treatments of long duration in order to achieve the desired tooth position. Long-term orthodontic treatment can have an increased risk of root resorption, gingival inflammation and dental caries. Moreover, movement of teeth through bone can be uneven, as teeth might "tip" due to the force applied, i.e., the crown of the tooth can move in the desired direction more quickly than the root of the tooth, resulting in tipping of the tooth. When teeth move "bodily" through the bone (i.e., in a more or less perpendicular orientation relative to the bone), the teeth move without tipping or with only a low degree of tipping.

Methods for increasing the rate of tooth movement without damage to the tooth and periodontium have been sought out. For example, acceleration of tooth movement can be produced by the local injection of prostaglandins, the active form of vitamin D3, and osteocalcin around the alveolar socket. These substances might increase the rate of tooth movement, but might also cause side effects such as local pain and discomfort for a patient during the process of injection.

An alternative strategy for increasing the rate of tooth movement is to improve bone regeneration. For example, light therapy has been found to be effective in the treatment of bone disorders and the biostimulation of bone and soft tissue, and can be effective in accelerating alveolar bone regeneration. Light can stimulate a variety of biological activities in cells and tissues that are compromised in function, for example, by stimulating cytochrome C oxidase or nitric oxide synthase.

Phototherapy or light therapy treatment is typically administered by a physician or therapist who directs light from a hand-held light emitting apparatus at an affected area. Light emitting apparatuses can be difficult to position consistently over the affected area. Sometimes a tattoo is used to identify the affected area. However, even with a tattoo or other reference mark it can be difficult to consistently administer light therapy treatments to an affected area.

Light therapy typically involves repeated treatments over at least several days. Thus, patients undergoing light therapy might be required to make multiple visits to a practitioner's office or clinic in order to complete a therapy regimen. Such repeated visits can be time consuming or expensive.

LEDs and other light emitters suitable for generating light for light therapy can get hot when they operate. Such light emitters can be inefficient at higher temperatures. Hot apparatuses can also be uncomfortable or even dangerous to patients.

Apparatuses for delivering light therapy to the dental and maxillofacial areas of a patient have been developed, for example as described in PCT publication numbers WO 2009/000075 and WO 2006/087633, both of which are hereby incorporated by reference in their entirety. However, there remains a need for light-therapy apparatuses that can deliver specifically targeted light therapy to flood desired regions of a patient's jawbone with light having desired characteristics.

There further remains a need for methods and apparatuses that are useful for increasing the velocity or improving the quality of tooth movement through bone in response to orthodontic treatment, to decrease treatment times for patients without undesirable side effects or pain. There is also a need for methods and apparatuses that can be used to achieve a desired mode or quality of movement of teeth through the bone, e.g., bodily movement of teeth through bone, and that are adjustable to permit tooth movement to be modulated at a desired specific location or locations within a patient's jaw region.

The foregoing examples of the related art and limitations related thereto are intended to be illustrative and not exclusive. Other limitations of the related art will become apparent to those of skill in the art upon a reading of the specification and a study of the drawings.

SUMMARY OF THE INVENTION

An aspect of the invention relates to methods for regulating tooth movement, comprising allowing a heavy force to be exerted on one or more teeth of a patient in need thereof; and administering an effective amount of light to the maxillary or mandibular alveolar bone of the patient, wherein the light is administered before, during, or after the heavy force is exerted.

Another aspect of the invention provides methods for maintaining or improving tissue health, comprising allowing a heavy force to be exerted on one or more teeth of a patient in need thereof; and administering an effective amount of light to the maxillary or mandibular alveolar bone of the patient, wherein the light is administered before, during, or after the heavy force is exerted.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

Each publication, patent, and patent application referenced in this specification is herein incorporated by reference in its entirety.

BRIEF DESCRIPTION OF THE DRAWINGS

Reference is now made to the following detailed description and the accompanying drawings of which.

DETAILED DESCRIPTION OF THE INVENTION

Figure 1:
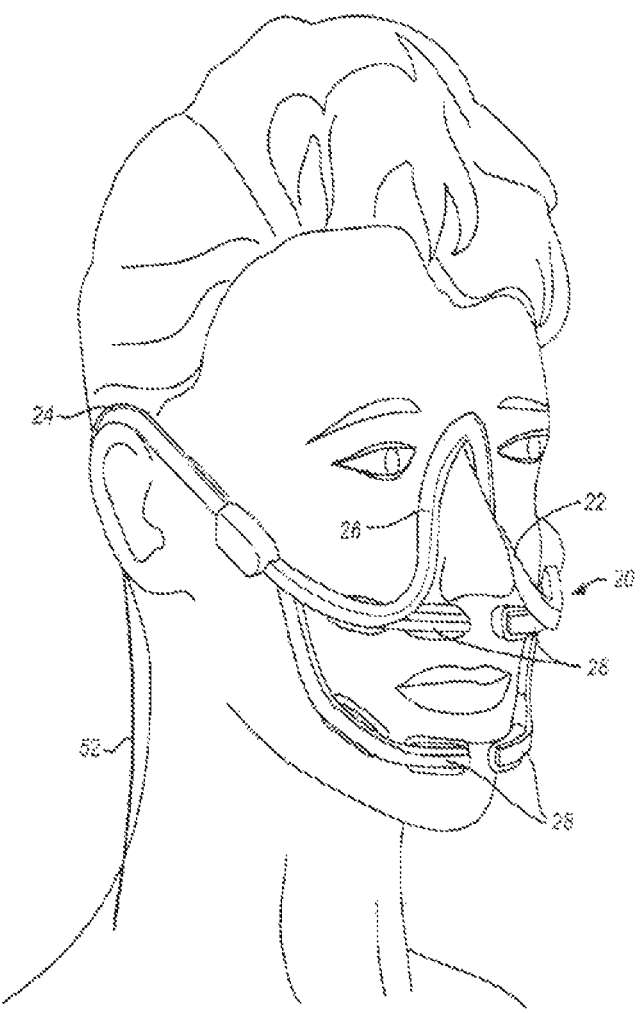
FIG. 1 is an isometric view of an embodiment of a light-therapy apparatus useful for providing light therapy to specified regions of a patient's maxillary or mandibular alveolar bone.

The term "about" as used herein in connection with a referenced numeric indication means the referenced numeric indication plus or minus up to 10% of that referenced numeric indication. For example, the language "about 50" units covers the range of 45 units to 55 units.

The term "surrounding" (or any variation thereof) as used herein means within about one (1) centimeter of a target object. For example, in some embodiments, the tissue that surrounds a tooth can refer to the tissue within about 1 cm of the tooth. In some embodiments, the methods disclosed herein are useful for preventing or minimizing inflammation that is within about 1 cm of a tooth.

The term "patient" as used herein refers to any living subject that can receive medical treatment. A patient can be, for example, a mammal such as a human. The patient can be an adult patient or a child patient. In some embodiments, the patient can be a living subject that receives light treatment, e.g., light administered to the patient extra-orally or intra-orally. In some such embodiments, the patient currently wears an orthodontic appliance. In other embodiments, however, the patient had worn, or previously wore, an orthodontic appliance prior to being administered with an effective amount of light transdermally or nontransdermally to a region of the patient's maxillary or mandibular alveolar bone. In yet other embodiments, the patient will wear an orthodontic appliance subsequent to being administered with an effective amount of light transdermally or nontransdermally to a region of the patient's maxillary or mandibular alveolar bone.

Methods for Regulating Tooth Movement or for Maintaining or Improving Tissue Health In accordance with an aspect of the invention, methods are provided for regulating tooth movement, comprising allowing a heavy force to be exerted on one or more teeth of a patient in need thereof; and administering to a patient in need thereof an effective amount of light to a region of the patient's maxillary or mandibular alveolar bone, wherein the light is administered before, during or after the heavy force is exerted. As is described in more detail herein, the light can be administered transdermally from an extra-oral light source or nontransdermally from an extra-oral or intra-oral light source.

Other embodiments of the invention provide methods for reducing, minimizing or preventing tooth root resorption comprising allowing a heavy force to be exerted on one or more teeth of a patient in need thereof; and administering an effective amount of light to the maxillary or mandibular alveolar bone of the patient, wherein the light is administered before, during, or after the heavy force is exerted.

Methods for reducing bone resorption or inflammatory dentin or cementum resorption of the tooth root or periodontium are further provided in accordance with another aspect of the invention. Such methods comprise allowing a heavy force to be exerted on one or more teeth of a patient in need thereof; and administering an effective amount of light to the maxillary or mandibular alveolar bone of the patient, wherein the light is administered before, during, or after the heavy force is exerted.

Another aspect of the invention provides methods for preventing or minimizing inflammation of tissue surrounding one or more teeth upon which heavy forces are or were exerted, comprising allowing a heavy force to be exerted on one or more teeth of a patient in need thereof; and administering an effective amount of light to the maxillary or mandibular alveolar bone of the patient, wherein the light is administered before, during, or after the heavy force is exerted.

Another aspect of the invention provides methods for regenerating maxillary or mandibular alveolar bone, comprising allowing a heavy force to be exerted on one or more teeth of a patient in need thereof; and administering an effective amount of light to the maxillary or mandibular alveolar bone of the patient, wherein the light is administered before, during, or after the heavy force is exerted.

Heavy Forces

The phrase "heavy force" as used herein refers to a force that ranges from about 150 grams of force to about 600 grams of force, and that is exerted on a tooth. For example, in some embodiments, a heavy force is a force having a magnitude of greater than about 150 grams of force. In other embodiments, a heavy force is a force having a magnitude of greater than or equal to about 175 grams of force, greater than or equal to about 190 grams of force, greater than or equal to about 200 grams of force, greater than or equal to about 210 grams of force, greater than or equal to about 225 grams of force, or greater than or equal to about 250 grams of force. In other embodiments, a heavy force is a force having a magnitude of less than or equal to about 300 grams of force, less than or equal to about 350 grams of force, less than or equal to about 400 grams of force, less than or equal to about 450 grams of force, less than or equal to about 500 grams of force, less than or equal to about 550 grams of force, or less than or equal to about 600 grams of force. In other embodiments, the heavy force's lower range is about 175 grams of force, about 190 grams of force, about 200 grams of force, about 210 grams of force, about 225 grams of force or about 250 grams of force. In other embodiments the heavy force's upper range is about 300 grams of force, about 350 grams of force, about 400 grams of force, about 450 grams of force, about 500 grams of force, about 550 grams of force, or about 600 grams of force. In some embodiments, the heavy force ranges from about 200 grams of force to about 500 grams of force. In other embodiments, the heavy force ranges from about 250 grams of force to about 450 grams of force. In one embodiment, the heavy force ranges from about 150 grams of force to about 300 grams of force.

In some embodiments, a heavy force is exerted on one or more teeth of the patient. For example, a heavy force can be exerted on one or more of the patient's teeth before, during, or after being administered with an effective amount of light to a region of the patient's maxillary or mandibular alveolar bone. In other embodiments, however, a force that is less than a heavy force is exerted on one or more of a patient's teeth. In this embodiment, the force has a magnitude of less than 150 grams of force, for example, a magnitude of about 100 grams of force or about 125 grams of force.

The phrase "magnitude of heavy force" as used herein refers to the amount of force exerted per tooth. Alternatively, the "magnitude of heavy force" can refer to the amount of force exerted on a plurality of teeth. The magnitude of force exerted per tooth in the latter instance is the total magnitude of force divided by the number of teeth. For example, if about 300 grams of force are exerted on to two teeth, then the force exerted on each tooth is about 150 grams. The phrase "gram of force" as used herein refers to a unit of force equal to the magnitude of force exerted on one gram of mass by a force of 9.80665 m/s$^2$ (i.e., standard gravity). In some embodiments, the magnitude of heavy force is a gram of force that is exerted on a tooth. In other embodiments, the magnitude of heavy force is a gram of force that is exerted on a plurality of teeth.

In some embodiments, a heavy force is a force of sufficient magnitude to cause at least some amount of root resorption. In some embodiments, a heavy force has sufficient magnitude to have pathophysiological effects, to create a hyalinized zone or tissue death, to cause cell death, or to cause tissue inflammation when the heavy force is exerted without any other form of treatment, such as light treatment. The heavy force can be an excessive pathophysiological force. A pathophysiological force may cause necrosis or root resorption. The heavy force can also cause pressure on the periodontium that can result in ischemia, decreased blood flow, or cell death.

A heavy force can be exerted on a tooth in any suitable manner. For example, in some embodiments, the heavy force is exerted normal (e.g., orthogonal or at a 90 degree angle) relative to a side of one or more teeth. In some embodiments, the heavy force is exerted at an angle relative to a side of one or more teeth. For example, the heavy force can be exerted at an angle of about 45 degrees, about 60 degrees, about 70 degrees, about 75 degrees, about 80 degrees, about 85 degrees, about 90 degrees, about 95 degrees, about 100 degrees, about 105 degrees, about 110 degrees, about 120 degrees, or about 135 degrees relative to a side of one or more teeth. A heavy force can be exerted normal (e.g., orthogonal or at a 90 degree angle) to, downwards to, or upwards to one or more teeth at any angle. In some embodiments, a heavy proximal force is applied to one or more teeth. In some other embodiments, a heavy distal force is applied to one or more tooth. In some embodiments, the heavy force is coronal pressure, e.g., a pressure exerted in the direction of or on the crown of the tooth, which is useful to intrude teeth; in other embodiments, the heavy force is apical pressure, e.g., a pressure exerted in the direction of or on the root, which is useful to extrude teeth. In some embodiments, a heavy force is exerted on a mesial (e.g., side of tooth towards front of mouth) side of the tooth. In some embodiments, a heavy force is exerted on a distal, e.g., side of tooth towards back of mouth) side of the tooth. A heavy force can be exerted on a buccal, e.g., side of tooth towards cheek, side of the tooth, or a heavy force can be exerted on a lingual, e.g., side of tooth towards tongue) side of the tooth. A heavy force can be exerted on an occlusal surface of a tooth. A heavy force can be exerted on an incisal surface of a tooth. A heavy force can be exerted on a proximal surface of a tooth, e.g., mesial or distal surfaces in between teeth. A heavy force can be exerted on an apical, e.g., toward a root end, surface of a tooth.

A heavy force may be directed to push one or more teeth toward one another. A heavy force may be directed to push one or more teeth apart. A heavy force may be directed to move one or more teeth toward a side. In some embodiments, a heavy force may shift a tooth sideways along a maxilla or mandible. Alternatively, a heavy force may move a tooth forwards or backwards relative to a maxilla or mandible.

In some embodiments, a heavy force is exerted at any point or region along a side of one or more teeth. In some embodiments, a heavy force is exerted at or near the top of one or more teeth, i.e., the side of a tooth opposite its root or roots. In some embodiments, a heavy force is exerted at or near the middle of the clinical crown, e.g., exposed to the air, above the gums, of one or more teeth. In other embodiments, a heavy force is exerted at or near the bottom of the clinical crown of one or more teeth, i.e., the clinical crown of a tooth closer to its root. In some embodiments, the heavy force is applied to the root of the one or more teeth. A heavy force can be exerted on one or more of the points or regions described above on one or more teeth. In some embodiments, a heavy force is exerted along the side of the tooth. Depending on where or for how long the heavy force is exerted, some or no tipping may occur to the tooth. Tipping is described in more detail below.

In some embodiments, a heavy force can increase the velocity of tooth movement relative to where no force or where a lighter force is exerted. In these embodiments, in other words, the heavy force reduces the amount of time it takes for the tooth to move to its desired position within the gum. Exertion of a heavy force on one or more of a patient's teeth, particularly where the patient is administered with an effective amount of light to his or her maxillary or mandibular alveolar bone, can further reduce the amount of time of orthodontic treatment that a patient might undergo.

In some embodiments, a heavy force is exerted on one or more teeth of a patient by one or more orthodontic appliances. Accordingly, in one embodiment, an orthodontic appliance can exert a heavy force on one or more of the patient's teeth to facilitate tooth movement. Orthodontic appliances are described in more detail below. In some embodiments, the orthodontic appliance can be present on one or more of the patient's teeth. In some embodiments, the patient wears two or more orthodontic appliance and less than all of these appliances exert a heavy force on one or more of the patient's teeth. For example, the orthodontic appliance can exert a heavy force on only one tooth of the patient or, alternatively, the orthodontic appliance can exert a heavy force on a plurality of teeth of the patient. In another embodiment, the orthodontic appliance can selectively exert a heavy force on less than all the teeth of the patient.

In some embodiments, an orthodontic appliance can be used for external anchorage, and can be the form of a temporary anchorage device or in the form of headgear. For example, a patient that wears a first orthodontic appliance for an extended period of time, e.g., 2 years, can concurrently wear a second orthodontic appliance, e.g., in the form of headgear, for temporary period of time, e.g., at night. The externally worn headgear can physically or electronically communicate with the first orthodontic appliance to facilitate tooth movement as well as to provide an external anchorage for the first orthodontic appliance. External anchorage can be used to facilitate the exertion of heavy forces to prevent untoward movement of anchorage teeth during use of heavy forces.

As is described in more detail below, the patient can wear an orthodontic appliance subsequent to initiating the administration of light. For example, the patient can wear an orthodontic appliance after one or more light treatment sessions are completed. In this manner, a heavy force can be exerted on one or more teeth of the patient by the orthodontic appliance(s) subsequent to initiating the administration of light. In some embodiments, however, a heavy force is exerted on one or more teeth of the patient during the administration of light. In such an embodiment, the patient wears an orthodontic appliance while receiving the light treatment. In other embodiments, a heavy force is exerted on one or more teeth of the patient prior to initiating the administration of light. The patient, for example, could wear her orthodontic appliance for any length of time before beginning the light treatment.

In some instances, heavy forces can cause a periodontal ligament to compress, which can eventually lead to ischemia or cell death. To prevent ischemia or eventual cell death, the heavy force is exerted with the light treatment as described above. In one embodiment, however, the heavy force is exerted after the light treatment has started. In some embodiment, the heavy force is exerted minutes, hours, or days after light treatment has started. In this manner, the light treatment can provide additional adenosine-5'-triphosphate (ATP) energy to tissue cells that will become stressed and could potentially become ischemic as a result of the heavy force. Illustrative frequencies of light treatment are described herein. In some embodiments, the heavy force is exerted concurrently with administration of light. In other embodiments, the heavy force is exerted subsequent to administration of light.

As described above, a heavy force can be exerted on one of more teeth from any direction. More particularly, in some embodiments, the force pushes two or more teeth together or apart, or pushes one or more teeth to one side or area of a patient's mouth. For example, in some embodiments, the force can push two or more teeth toward the front of the patient's mouth, to the back of the patient's mouth, to the left of the patient's mouth, or to the right of the patient's mouth.

The phrase "regulating tooth movement" as used herein refers to and includes one or more of the following functions and/or operations. For example, regulating tooth movement can include controlling the position of one or more teeth relative to a supporting tissue. Regulating tooth movement can also include controlling (e.g., increasing, decreasing, maintaining) the velocity of tooth movement relative to a supporting tissue. For example, regulating tooth movement can include increasing the velocity, or speed, of tooth movement. Regulating tooth movement can also include controlling (e.g., increasing, decreasing) bodily movement, e.g., less tipping, more tipping, of one or more teeth. Regulating tooth movement can comprise moving one or more teeth bodily. "Bodily" movement occurs when the tooth movement is generally perpendicular to the bone; "tipping" occurs when the crown or coronal region of the tooth moves more quickly than the root or apical region of the tooth. Bodily tooth movement can include moving a tooth without causing significant tipping of the tooth. By "significant tipping" is meant that about 20% of the tooth does not move in the same lateral direction as the remaining about 80%; in another embodiment about 10% of the tooth does not move in the same lateral direction as the remaining about 90%; in another embodiment about 5% of the tooth does not move in the same lateral direction as the remaining about 95%. Tooth movement can include lateral displacement of one or more teeth. Regulating tooth movement can include inducing the tilting or tipping one or more teeth, minimizing or preventing the tilting or tipping one or more teeth, or maintaining an alignment or orientation of the one or more teeth. Regulating tooth movement can also include stabilizing tooth movement. In some instances, regulating tooth movement can include causing one or more teeth to maintain their position. In some embodiments, regulating tooth movement can include a combination of causing the displacement of one or more teeth and causing one or more other teeth to maintain their position.

Administering Light Treatment

Light can be administered to the patient in any of the following ways. The act or process of administering light is also referred to herein as "light treatment". These terms are used interchangeably herein but are intended to have similar meanings unless otherwise stated.

Light can be administered to a region of the patient's maxillary or mandibular alveolar bone, or other region of the patient. In some embodiments, the light can be directed to one or more regions of a patient. The region can be within the patient's mouth. Some examples of these regions include, but are not limited to, one or more teeth (e.g., incisor, canine, premolar, or molar, such as a maxillary central incisor, maxillary lateral incisor, maxillary canine, maxillary first premolar, maxillary second premolar, maxillary first molar, maxillary second molar, maxillary third molar, mandibular central incisor, mandibular lateral incisor, mandibular canine, mandibular first premolar, mandibular second premolar, mandibular first molar, mandibular second molar, or mandibular third molar), a root of one or more teeth (e.g., wherein a root of a tooth may include a portion of one or more roots supporting the tooth, one root supporting the tooth, a plurality of roots supporting the tooth, or all of the roots supporting the tooth), tissue supporting one or more teeth, a portion of the maxilla (e.g., portion of the patient's maxillary alveolar bone), a portion of the mandible (e.g., portion of the patient's mandibular alveolar bone), alveolus, basal tissue, gingiva, periodontal ligaments, cementum, periodontium, a region of a jaw bone or tissue, or at least a portion of the patient's other oral soft tissue or bone tissue. The region can be located on a left side or right side of the patient's face. In some embodiments, one or more regions are located on both the left and right side of the patient's face. In some embodiments, the region can be located on the front side of the patient's face. The region can include one, two, three, four, five, six, seven, eight, or more teeth, or tissue surrounding or supporting the teeth. The region can include one or more roots of one, two, three, four, five, six, seven, eight, or more teeth, or periodontium of teeth. Regions can include tissue (e.g., alveolar or basal tissue) surrounding or supporting any of the teeth specifically described with or without including the tooth itself. Regions can include teeth or tissue supported by the maxilla or teeth supported by the mandible. One or more regions can be adjacent to one another, continuous with one another, or separate from one another. Any description herein of regions or examples of regions can apply to any other region or examples of treatment regions provided herein.

In some embodiments, light can irradiate a region that can include a portion of tissue (e.g., bone tissue, or soft tissue) or other regions within the patient's oral cavity without irradiating one or more other portions of the patient's oral cavity. For example, light can irradiate the mandibular first molar on the right side of the patient's oral cavity without irradiating the mandibular third molar that is also located on the right side of the patient's oral cavity. In some embodiments, light is administered to one or more roots of only one tooth root and to only one periodontium. Alternatively, light is administered to one or more roots of a plurality of teeth and to a plurality of periodontia. Light can be administered to one or more roots of all or less than all the teeth and periodontia in the patient's oral cavity. One or more selected teeth, roots or periodontia can be irradiated with light. For example, the mandibular first molar and the mandibular third molar on the right side of the patient's oral cavity can be irradiated without the mandibular second molar being irradiated.

In some embodiments, light can irradiate a region that can include a portion of tissue (e.g., bone tissue, or soft tissue) or other regions within the patient's oral cavity at a much greater intensity than it irradiates other portions of the patient's oral cavity. For example, light can irradiate a first region at an intensity that is 3×, 5×, 10×, 20×, 50×, or 100× greater than the intensity that irradiates any other region or portion of the patient's oral cavity. In one embodiment, light can irradiate a portion of a patient's maxillary or mandibular alveolar bone at a greater intensity than that of light that irradiates any of the patient's teeth. In another embodiment, light can irradiate or be focused with a greater intensity on the one or more teeth upon which heavy forces are applied (that are desired to be moved), relative to the one or more teeth on which heavy forces are not exerted. Teeth with lower forces or anchorage teeth can be selectively shielded from light or irradiated at lower light intensity so that they can move less and the anchorage effect can be enhanced. In some embodiments, this is achieved by applying to the patient, or adjusting within the patient, one or more intra-oral or extra-oral light-translucent or light-opaque masks that shield from light one or more non-regions. In some embodiments, light reaching a region can have an intensity that is greater than a threshold value. In some embodiments, the threshold value can have an intensity as described elsewhere herein.

In some embodiments, the region can be close to a surface within the patient's mouth, or within a soft tissue or bone tissue. The region can be at a depth from the surface of the patient's face. For example, the region can be about 1 µm, about 10 µm, about 50 µm, about 100 µm, about 200 µm, about 300 µm, about 500 µm, about 750 µm, about 1 mm, about 2 mm, about 3 mm, about 4 mm, about 5 mm, about 7 mm, about 10 mm, about 15 mm, about 20 mm, about 25 mm, about 30 mm, about 40 mm, about 50 mm, about 60 mm, or about 70 mm from the surface of the patient's face. Light can irradiate a region, which can have an area greater than, less than, or about 1 nm$^2$, about 1 µm$^2$, about 0.1 mm$^2$, about 0.2 mm$^2$, about 0.3 mm$^2$, about 0.4 mm$^2$, about 0.5 mm$^2$, about 0.7 mm$^2$, about 1 mm$^2$, about 10 mm$^2$, about 0.2 cm$^2$, about 0.5 cm$^2$, about 1 cm$^2$, about 2 cm$^2$, about 3 cm$^2$, about 5 cm$^2$, about 7 cm$^2$, about 10 cm$^2$, about 15 cm$^2$, about 20 cm$^2$, about 25 cm$^2$, about 30 cm$^2$, about 35 cm$^2$, about 40 cm$^2$, about 50 cm$^2$, or about 60 cm$^2$. Light can irradiate one area, a plurality of areas, a point, or a plurality of points. In some embodiments, light can irradiate a particular area without irradiating with significant intensity surrounding areas. For example, light can irradiate a portion of jawbone without significant amounts of light irradiating teeth on that jawbone. In another embodiment, light can irradiate a particular tooth or set of teeth without significant amounts of light irradiating adjacent teeth. In one embodiment, irradiating a tooth includes irradiating an exposed surface of the tooth, a tooth root, or a periodontium of the tooth.

In some embodiments, light can be administered extra-orally to the patient. In some embodiments, light can be provided from a light-therapy apparatus, embodiments of which are described below. Light can be emitted from a light source that can include characteristics, features, components, or configurations of any of the light-therapy apparatus embodiments, as described below. A method for regulating tooth movement can further comprise providing a light-therapy apparatus. The method for regulating tooth movement can also further comprise administering light from a light-therapy apparatus. Light can be provided from any other source, and is not limited to a light-therapy apparatus as described herein.

Light administered extra-orally can include or refer to light administered from outside the patient's face. In some embodiments, light can be provided from a light source that can contact the patient's face, e.g., the stratum corneum of the patient's face. Similarly, light can be emitted from a plurality of light sources that can contact the patient's face. In one embodiment, one or more light sources can contact skin of the patient's face overlaying a region. Light can be administered from a light source that can provide pressure on the patient's face. Light can pass through the patient's face to irradiate the region. The region can be located within a patient's oral cavity. In some embodiments, a light emitter can be provided externally to the oral cavity. A portion of a patient's face, such as the cheek, skin over the jaw, lips, or chin can be located between the light emitter and the oral cavity. Light can be administered transcutaneously to a region that is located within the patient's oral cavity. The light can transcutaneously pass through the skin of the patient to irradiate the region. Light can pass through the cheek of the patient, the skin overlaying the jaw of the patient, the chin of the patient, the lips of the patient, or any other region circumscribed or otherwise defined by the patient's face. In some embodiments, light can irradiate a region by manually retaining one or more light sources providing light of one or more wavelengths to one or more regions of a patient. In some embodiments, light can irradiate a region only transdermally through the skin of the patient. In some embodiments, light is administered only extra-orally, and is not administered intra-orally. In some alternate embodiments, light can be administered intra-orally or extra-orally. In one embodiment the patient to whom the light is administered has his or her mouth closed.

In other embodiments of extra-orally administered light, the light source does not contact the patient's face. For example, extra-oral light can be administered to the patient wherein a gap exists between a light source and skin of the patient's face. The light source can be in close proximity to the skin of the patient's face without contacting the patient's face. In some embodiments, light can be administered from a light source that does not contact a patient's face when the patient's face is relaxed but can contact the face if the patient flexes a portion of the patient's face or tenses the face. In some embodiments, a light source is about 1 mm or less, about 2 mm or less, about 3 mm or less, about 5 mm or less, about 7 mm or less, about 1 cm or less, about 1.5 cm or less, about 2 cm or less, about 2.5 cm or less, or about 3 cm or less away from a patient's face while the patient's face is relaxed or tensed. Light can be emitted from a light source located at a particular distance from a region. In some embodiments the distance is about 0.1 mm or less, about 0.5 mm or less, about 1 mm or less, about 2 mm or less, about 3 mm or less, about 5 mm or less, about 7 mm or less, about 1 cm or less, about 1.5 cm or less, about 2 cm or less, about 2.5 cm or less, or about 3 cm or less. In some embodiments, a light source is about 0.1 mm, about 0.5 mm, about 1 mm, about 3 mm, about 5 mm, about 7 mm, about 1 cm, about 1.5 cm, about 2 cm and about 2.5 cm, about 2.75 cm, about 3 cm, about 3.5 cm, or about 4 cm away from the region to be treated by or irradiated by an effective amount of light.

In some embodiments, light is administered intra-orally to the patient. For example, the light source may be located within the patient's oral cavity. In some embodiments, light is administered directly, i.e., nontransdermally, to a selected region or to a surface overlaying the selected region. In some embodiments, light is administered to a selected region through the patient's gums or soft tissue. Light need not be applied transdermally or through the patient's face. In some embodiments, the light source may contact the selected region or surface overlaying the selected region. For example, the light source may contact a patient's tooth or gum.

Extra-oral or intraoral light can be administered from a single light source. Alternatively, light can be administered from multiple light sources. Light can irradiate a continuous region or one or more discrete regions. Light can irradiate various regions from different directions. For example, light can be administered from a right side of a patient's face and from a left side of a patient's face. Light can be administered so that it is angled upward toward a region, or can be administered so that it is angled downward to toward a region. In some embodiments, light can be administered from one or more stationary sources. For example, a light source can remain stationary during administration. In some embodiments, light can be administered from one or more moving light sources. A light source can be displaced, can be angled, can be rotated, or any combination thereof. Light can be administered from a continuously moving source, or can be administered from a discretely or abruptly moving source.

As described above, an effective amount of light can be administered. An effective amount of light is an amount of light that, when administered before, during or after exertion of a heavy force on one or more of a patient's teeth, is effective for regulating tooth-movement; reducing, preventing or minimizing tooth-root resorption; reducing bone resorption, inflammatory dentin resorption or cementum resorption; preventing or minimizing inflammation of tissue surrounding one or more teeth upon which heavy forces are or were exerted; or regenerating maxillary or mandibular alveolar bone. The light's properties can include, but are not limited to: its intensity, wavelength, coherency, range, peak wavelength of emission, energy density, continuity, pulsing, duty cycle, frequency or duration.

In some embodiments, a method for regulating tooth movement can further comprise determining an effective dosage of light. The determination can be based on an intended tooth movement regulation effect. The method can further comprise selecting one or more light properties to provide the effective dosage of light. The method can further comprise receiving instructions from a controller, and emitting light having particular properties. The controller can be any controller described herein or can implement any of the steps described herein.

Light can be administered from one or more light source capable of irradiating light having intended properties. A light source can emit light from one or more light emitters. In some embodiments, a light source comprises about 10 to about 15 emitters, about 15 to about 20 emitters, about 20 to about 30 emitters, about 30 to about 40 emitters, about 40 to about 50 emitters, about 50 to about 70 emitters, or about 70 emitters to about 100 emitters. For example, light can be administered from a light source, which can comprise one or more of the following emitters: a light-emitting diode (LED), which can be present in an array; and a laser, for example a vertical cavity surface emitting laser (VCSEL) or other suitable light emitter such as an Indium-Gallium-Aluminum-Phosphide (InGaAlP) laser, a Gallium-Arsenic Phosphide/Gallium Phosphide (GaAsP/GaP) laser, or a Gallium-Aluminum-Arsenide/Gallium-Aluminum-Arsenide (GaAlA5/GaAs) laser. In one embodiment the light source comprises a plurality of lasers. A plurality of light emitters can emit light at one or more different wavelengths. Alternatively, one or more light emitters can emit light at the same wavelength for a light source. One or more light emitters can be arranged on a light source in any manner, such as a linear array or another arrangement described herein.

An effective amount of light can have an intensity that is effective for regulating tooth movement. In one embodiment, the light intensity is at least about 10 mW/cm$^2$. In other embodiments, the light intensity is about 1 mW/cm$^2$ or greater, about 3 mW/cm$^2$ or greater, about 5 mW/cm$^2$ or greater, about 7 mW/cm$^2$ or greater, about 12 mW/cm$^2$ or greater, about 15 mW/cm$^2$ or greater, about 20 mW/cm$^2$ or greater, about 30 mW/cm$^2$ or greater, about 50 mW/cm$^2$ or greater, about 75 mW/cm$^2$ or greater, about 100 mW/cm$^2$ or greater, about 200 mW/cm$^2$ or greater, about 500 mW/cm$^2$ or greater, or about 1 W/cm$^2$ or greater. In other embodiments, the light intensity is about 20 mW/cm$^2$ or less, about 30 mW/cm$^2$ or less, about 50 mW/cm$^2$ or less, about 75 mW/cm$^2$ or less, about 100 mW/cm$^2$ or less, about 200 mW/cm$^2$ or less, about 500 mW/cm$^2$ or less, about 1 W/cm$^2$ or less, about 2 W/cm$^2$ or less, about 5 W/cm$^2$ or less, or about 10 W/cm$^2$ or less. In one embodiment the light intensity ranges from about 1 mW/cm$^2$ to about 10 W/cm$^2$. In another embodiment, the light intensity's lower range is about 3 mW/cm$^2$, about 5 mW/cm$^2$, about 7 mW/cm$^2$, about 12 mW/cm$^2$, about 15 mW/cm$^2$, about 20 mW/cm$^2$, about 30 mW/cm$^2$, about 50 mW/cm$^2$, about 75 mW/cm$^2$, about 100 mW/cm$^2$, about 200 mW/cm$^2$, about 500 mW/cm$^2$, or about 1 W/cm$^2$. In another embodiment, the light intensity's upper range is about 20 mW/cm$^2$, about 30 mW/cm$^2$, about 50 mW/cm$^2$, about 75 mW/cm$^2$, about 100 mW/cm$^2$, about 200 mW/cm$^2$, about 500 mW/cm$^2$, about 1 W/cm$^2$, about 2 W/cm$^2$, about 5 W/cm$^2$, or about 10 W/cm$^2$. Light can be administered having an intensity falling within a range determined by any of the intensities mentioned above. In some embodiments the intensity is an average intensity. In some embodiments, the light has an intensity in the range of about 10 mW/cm$^2$ to about 60 mW/cm$^2$, or about 20 mW/cm$^2$ to about 60 mW/cm$^2$. In such embodiments, the peak light intensity can about 50 mW/cm$^2$ or greater. A peak wavelength is the wavelength at which the highest intensity of light is emitted. In some embodiments, light can be pulsed. In other embodiments, the output of light is continuous. In some embodiments, the light intensity can vary over time in a cyclical or non-cyclical fashion. The light intensity can vary with or without pulsing. In some embodiments, pulse width modulation can be used to effect a desired light intensity. If one or more wavelengths of light are administered, then each wavelength can be administered at its own intensity. Additional details regarding effective amounts or dosages of light are described below.

In some embodiments, an effective amount of light can include light having a wavelength that is within in a particular range, or light of a range of wavelengths. The light is not necessarily visible light. For example, the light can include infrared light or near-infrared light. The light can also be provided in the visible light region. Light can be administered having one or more wavelengths ranging from about 620 nm to about 1000 nm. In some embodiments, administered light has one or more wavelengths ranging from about 585 nm to about 665 nm, about 815 nm to about 895 nm, about 640 nm to about 680 nm, or about 740 nm to about 780 nm, or any given wavelength or range of wavelengths within those ranges, such as, for example, about 625 nm or about 855 nm, or about 605 nm to about 645 nm, or about 835 nm to about 875 nm. In some embodiments, the administered light has one or more wavelengths from about 605 nm to about 645 nm, or from about 835 nm to about 875 nm. In some embodiments, the administered light has one or more wavelengths from about 615 nm to about 635 nm, or from about 845 nm to about 865 nm. In some embodiments, the wavelengths of the administered light can be about 625 nm or about 855 nm. In additional embodiments, the administered light has one or more wavelengths ranging from about 400 nm to about 1200 nm. In particular embodiments, the administered light has one or more wavelengths ranging from about 500 nm to about 700 nm, about 585 nm to about 665 nm, about 605 nm to about 630 nm, about 620 nm to about 680 nm, about 815 nm to about 895 nm, about 820 nm to about 890 nm, about 640 nm to about 680 nm, or about 740 nm to about 780 nm. In some embodiments the administered light has one or more wavelengths in one or both of the following wavelength ranges: about 820 to about 890 nm and about 620 to about 680 nm. In some embodiments, the administered light has one or more wavelengths in the ranges of about 820 to about 890 nm and about 620 to about 680 nm. In some embodiments, the administered light has one or more wavelengths in the ranges of about 815 to about 895 nm and about 585 to about 665 nm. The administered light can alternatively have one or more wavelengths in one or more of the following ranges: about 613 nm to about 624 nm, about 667 nm to about 684 nm, about 750 nm to about 773 nm, about 812 nm to about 846 nm. In one embodiment, the light intensity's lower range is about 400 nm, about 450 nm, about 500 nm, about 550 nm, about 585 nm, about 595 nm, about 605 nm, about 613 nm, about 615 nm, about 620 nm, about 624 nm, about 625 nm, about 640 nm, about 650 nm, about 667 nm, about 680 nm, about 710 nm, about 740 nm, about 750 nm, about 770 nm, about 812 nm, about 815 nm, about 820 nm, about 835 nm, about 845 nm, or about 860 nm. In another embodiment, the light intensity's upper range is about 585 nm, about 605 nm, about 624 nm, about 630 nm, about 635 nm, about 645 nm, about 655 nm, about 660 nm, about 665 nm, about 680 nm, about 684 nm, about 700 nm, about 725 nm, about 755 nm, about 773 nm, about 780 nm, about 795 nm, about 815 nm, about 830 nm, about 846 nm, about 855 nm, about 865 nm, about 875 nm, about 890 nm, about 895 nm, about 935 nm, about 975 nm, about 1000 nm, about 1050 nm, about 1100 nm, or about 1200 nm.

In some embodiments, light is administered at one, two, or more of the light ranges described. In some instances, light is not administered outside of one, two, or more of the light ranges described. In other embodiments, administered light has other wavelengths, as desired for a particular application. In some embodiments, light having a first set of characteristics (e.g., wavelength, intensity, pulsing, timing) can be administered to a first region, and light with a second set of characteristics can be administered to a second region. The first region and the second region can be the same region, can partially overlap, or cannot overlap. The first set of characteristics can be the same as the second set of characteristics, can partially overlap with the second set, or can all be different from the second set. In one embodiment, one region of a jaw can receive light within a first wavelength range, while another region of the jaw can receive light within a second wavelength range. The first and second wavelengths can overlap. Alternatively, the first and second wavelengths do not overlap.

Although examples of light wavelength ranges are provided below for different applications, light having any other light wavelength value, which can include those described above, can be administered for those applications.

Extra-orally administering to a patient light having a wavelength in the range of about 815 nm to about 895 nm, such as about 835 nm to about 875 nm, or about 855 nm, is useful in the present methods, in one embodiment, for increasing the rate of movement of teeth. In another embodiment, intra-orally administering to a patient light having a wavelength in the range of about 815 nm to about 895 nm, such as about 835 nm to about 875 nm, or about 855 nm, is useful in the present methods, in one embodiment, for increasing the rate of movement of teeth. In one embodiment increasing the rate of tooth movement does not increase the tipping motion of teeth beyond that which is experienced by orthodontic patients who are not provided with light.

Extra-orally administering transdermally to a patient light having a wavelength in the range of about 585 nm to about 665 nm, such as about 605 nm to about 645 nm, or about 625 nm, is likewise useful in the present methods, in one embodiment, for increasing the rate of movement of teeth. In another embodiment, intra-orally administering to a patient light having a wavelength in the range of about 585 nm to about 665 nm, such as about 605 nm to about 645 nm, or about 625 nm, is likewise useful in the present methods, in one embodiment, for increasing the rate of movement of teeth.

In one embodiment administration of light having a wavelength in the range of about 585 nm to about 665 nm increases the amount or extent of bodily tooth movement to a greater degree than administration with light having a wavelength in the range of about 815 nm to about 895 nm. Administering light having a wavelength in the range of about 585 nm to about 665 nm (e.g., about 625 nm) can result in about 10% to about 50% less tipping than the administration of light having a wavelength in the range of about 815 nm to about 895 nm (e.g., about 855 nm). For example, about 10%, about 15%, about 20%, about 25%, about 30%, about 35%, about 40%, about 45%, or about 50% less tipping can occur. Particular wavelengths of light can minimize tipping.

Thus, in one embodiment administration of light having a wavelength in the range of about 605 nm to about 645 nm, such as about 625 nm, is useful in the present methods, in one embodiment, for facilitating the bodily movement of teeth in orthodontic treatment and optionally increase bone regeneration. In some embodiments the methods further comprise increasing bone regeneration. In another embodiment administration of light having a wavelength in the range of about 835 to about 875 nm, such as about 855 nm, is useful in the present methods, in one embodiment, for increasing the rate of movement of teeth for which some degree of tipping movement is desirable or acceptable and optionally increasing bone regeneration.

In other embodiments administration of light having a wavelength in the range of about 605 nm to about 645 nm, such as about 625 nm, is useful in the present methods, in one embodiment, for increasing the quality or degree of bone remodeling. Accordingly the present invention further relates to methods for increasing the quality or degree of bone remodeling, comprising allowing a heavy force to be exerted on one or more teeth of a patient in need thereof and administering to a patient in need thereof an effective amount of light to a region of the patient's maxillary or mandibular alveolar bone, or to other regions as described herein. For example, light can be administered to regions of oral and maxillofacial bone or tissue.

Bone remodeling can include changes in any bone characteristic, such as, but not limited to, bone shape, bone volume, bone density, or bone mineral content. Increasing the quality or degree of bone remodeling can aid in increasing the retention of teeth in a particular position, for example, in a position resulting from orthodontic treatment, such as an appliance of one or more orthodontic appliances, decreasing the potential for teeth to move back to a previous position, for example, a position prior to orthodontic treatment, such as any appliance of one or more orthodontic appliances. Thus, administration of light having a wavelength in the range of about 585 nm to about 665 nm, or about 605 nm to about 645 nm, or about 615 nm to about 635 nm, or about 625 nm, optionally also with light in the range of 815 nm to 895 nm, can be useful in the present methods, for example, for stabilizing the movement of teeth prior to, subsequent to or concurrently with orthodontic treatment. Accordingly in other embodiments the present methods further comprise performing orthodontic treatment, such as installing one or more orthodontic appliances to the patient, prior to, subsequent to or concurrently with the administration of light. In one embodiment the appliance is a retainer device or a passive orthodontic appliance. For example, suitable appliances include removable retainers such as a Hawley retainer or a vacuum formed retainer, or fixed retainers such as a bonded lingual retainer. These appliances can assist in maintaining tooth position prior to, subsequent to or concurrently with the administration of light, for example by stimulating bone regeneration. Administration with light having a wavelength in the range of about 815 nm to about 895 nm, or about 835 nm to about 875 nm, or about 845 nm to about 865 nm, or about 855 nm, can also be useful for stabilizing tooth movement, in one embodiment prior to, subsequent to or concurrently with orthodontic treatment. In one embodiment administration of light having wavelengths in the range of about 585 nm to about 665 nm increases bone regeneration to a greater degree or extent that does administration of light having wavelengths in the range of about 815 nm to about 895 nm.

Tooth-root resorption can include breakdown or destruction, or subsequent loss, of the root structure of a tooth. Tooth-root resorption can be caused by differentiation of macrophages into osteoclasts in surrounding tissue which, if in close proximity to the root surface can resorb the root surface cementum and underlying root dentine. The cause of the tooth-root resorption can be increased supra physiologic pressure on the periodontium which can cause cell death of bone soft tissue and bone in the periodontium. This can create an area of hyalinized tissue which then stimulates the macrophages and multi-nuclear giant cells to resorb the necrotic tissue and in the process can cause cementum and dentin resorption of the root.

Accordingly, administering light having a particular wavelength, is useful for modulating the speed, quality and type of tooth movement, e.g., bodily versus tipped, and for increasing or stabilizing tooth movement. In some embodiments, stabilizing tooth movement can comprise moving one or more teeth with less tipping. Stabilizing tooth movement can also include retarding or arresting tooth movements in particular ways. For example, this can include minimizing the amount of, or eliminating, slanting. Administration of light can also be useful for increasing bone regeneration. Administration of light can also be useful for reducing, minimizing, or preventing tooth root resorption, bone resorption, inflammatory dentin or cementum resorption, or inflammation of tissue.

In some embodiments, the light can be administered to substantially the entirety of a patient's maxillary and mandibular bone. Alternatively, using a light-therapy apparatus or other suitable apparatus, light of one or more particular wavelengths can be administered to different selected regions of a patient's maxillary and mandibular alveolar bone in order to effect movement of teeth (e.g. anchor (no movement), bodily, or tipped) in one or more regions of a patient's mouth. For example, one or more regions in which it is desired that the teeth not be moved, or that the teeth serve as an anchor to facilitate movement of teeth in other selected regions of a patient's jaw, can be optionally screened or masked such that they receive no light. Regions in which it is desired that the teeth be moved bodily can be administered with light having a wavelength in the range of about 585 nm to about 665 nm, in the range of about 605 nm to about 645 nm, about 615 nm to about 635 nm, or about 625 nm. Regions in which it is desired to increase tooth movement but permit some tipping of the teeth can be administered with light having a wavelength in the range of about 815 nm to about 895 nm, about 835 nm to about 875 nm, about 845 nm to about 865 nm, or about 855 nm. Tooth movement can be selectively regulated by administering an effective amount of light having one wavelength to one or more selected regions of a patient's maxillary or mandibular alveolar bone, and by administering an effective amount of light having a different wavelength to one or more different selected regions of the bone.

In some embodiments, light can be administered within a narrow range of wavelengths (e.g., 50 nm or less, 30 nm or less, 20 nm or less, 10 nm or less, 5 nm or less), or at a single wavelength. In some embodiments, light can be emitted at one, two, or more peak wavelengths of emission. A peak wavelength is the wavelength at which the highest intensity of light is emitted. In some embodiments, light can be administered at a range of wavelengths that includes a peak wavelength having the highest intensity within the range. In some embodiments, a peak wavelength can be at about 620 nm, about 640 nm, about 650 nm, about 655 nm, about 660 nm, about 665 nm, about 670 nm, about 680 nm, about 690 nm, about 800 nm, about 820 nm, about 830 nm, about 835 nm, about 840 nm, about 845 nm, about 850 nm, about 860 nm, about 870 nm, or about 890 nm.

Where two or more light wavelengths are administered, the light can be administered at any ratio of each wavelength's intensity. For example, light administered at a first wavelength can have an intensity that is about 1.1×, 1.2×, 1.3×, 1.5×, 1.7×, 2.0×, 2.5×, 3.0×, 3.5×, 4.0×, 5.0×, 10×, 12×, 15×, 20×, 30×, 50×, 100× that of light administered at a second wavelength. In some embodiments, the administered light is emitted from one or more light emitters, in another embodiment, from one or more light emitters having a first set of properties and, optionally, from a second set of light emitters having a second set of properties. In other embodiments, the number of light emitters having a first set of characteristics exceeds that of the light emitters having a second set of characteristics. For example, the number of light emitters having the first set of characteristics can be about 1.1×, 1.2×, 1.3×, 1.5×, 1.7×, 2.0×, 2.5×, 3.0×, 3.5×, 4.0×, 5.0×, 10×, 12×, 15×, 20×, 30×, 50×, 100× the number of light emitters having the second set of characteristics, or vice versa.

The light can optionally be substantially monochrome. Administering light from light emitters that emit at multiple wavelengths can allow for irradiation over multiple wavelengths or greater selectivity and precision in administration. The light can optionally comprise incoherent light. In some embodiments, light can be administered at a single frequency, light can have a phase that drifts relatively quickly, a pulse of light waves can have an amplitude that changes quickly, or a light wave can encompass a broad range of frequencies.

Light can be administered directly from a light emitter. Light can be emitted and can travel directly through a patient's face to a region. In another embodiment, the light is administered nontransdermally to a region or the oral tissue above the region. In some embodiments, light can be modified by optics before reaching the patient's face or traveling through the patient's face. For example, light can be diffused, focused, parallel, reflected, redirected, or filtered after it is emitted and before it reaches the patient's face or travels through the patient's face. In one embodiment, light of one or more wavelengths can be selectively blocked or partially filtered before reaching the patient's face or a region. In some embodiments, light can diverge or converge from an emission source before reaching the region. For example, light can diverge in a beam having an included angle Θ. in the range of about 45-60°. The emitted light diverge to have an included angle Θ of 0 to about 15°, 0 to about 30°, 0 to about 45°, 0 to about 60°, 0 to about 75°, 0 to about 90°, or 0 to about 120°.

Light that irradiates the region can optionally have the same or about the same characteristics as light that is emitted. In some embodiments, light that reaches the region does not have the same characteristics as the light that is emitted. One or more of the light characteristics can optionally be altered prior to administration or when it passes through the face of the patient. One or more of the light characteristics can optionally be altered when it passes through optics, such as one or more lenses or mirrors. For example, one or more of the light characteristics can be altered in the range of about ±20% or less, about ±15% or less, about ±10% or less, about ±5% or less, about ±3% or less, about ±1% or less, about ±0.5% or less, or about ±0.1% or less.

An effective amount of light can range from about 24 $J/cm^2$ to about 200 $J/cm^2$. The effective dosage of light can be administered once or repetitively. In some embodiments, the effective amount of light can have a light energy density that is from about 30 $J/cm^2$ to about 100 $J/cm^2$. In other embodiments, the effective amount of light can be about 5 $J/cm^2$ or less, about 10 $J/cm^2$ or less, about 20 $J/cm^2$ or less, about 30 $J/cm^2$ or less, about 50 $J/cm^2$ or less, about 75 $J/cm^2$ or less, about 100 $J/cm^2$ or less, about 125 $J/cm^2$ or less, about 150 $J/cm^2$ or less, about 175 $J/cm^2$ or less, or about 200 $J/cm^2$ or less. The effective amount of light can be about 1 $J/cm^2$ or more, about 5 $J/cm^2$ or more, about 10 $J/cm^2$ or more, about 20 $J/cm^2$ or more, about 25 $J/cm^2$ or more, about 30 $J/cm^2$ or more, about 40 $J/cm^2$ or more, about 50 $J/cm^2$ or more, about 60 $J/cm^2$ or more, about 75 $J/cm^2$ or more, about 100 $J/cm^2$ or less, about 125 $J/cm^2$ or more, about 150 $J/cm^2$ or more, or about 175 $J/cm^2$ or more. The effective amount of light can be in a range bounded by any of the energy density values described above. The effective amount of light can be increased, for example, by using a light source that emits light having a relatively higher average intensity, or by increasing the duration of administration of light.

The duration over which the effective amount, which is optionally repetitive, is administered can range from about 10 to about 40 minutes. In other embodiments, dosage can be administered in a period of time of about 30 seconds or more, about 1 minute or more, about 2 minutes or more, about 3 minutes or more, about 5 minutes or more, about 7 minutes or more, about 10 minutes or more, about 15 minutes or more, about 20 minutes or more, about 25 minutes or more, about 30 minutes or more, about 40 minutes or more, about 50 minutes or more, about 1 hour or more, about 1 hour 15 minutes or more, about 1 hour 30 minutes or more, or about 2 hours or more. The effective amount can be administered in a period of time of about 3 minutes or less, about 5 minutes or less, about 10 minutes or less, about 15 minutes or less, about 20 minutes or less, about 25 minutes or less, about 30 minutes or less, about 35 minutes or less, about 40 minutes or less, about 50 minutes or less, about 1 hour or less, about 1 hour 15 minutes or less, about 1 hour 30 minutes or less, about 2 hours or less, or about 4 hours or less. The effective amount can be administered in a range of time within any of the time values mentioned above. Such light therapy can include light emission that has been provided extra-orally. In some embodiments, one or more intra-oral light blocking masks or shades can be used. An oral mask can block one or more wavelengths of light, or can reduce the intensity of one or more wavelengths of light, from reaching a region covered by the oral mask. This can include an upper arch (e.g., maxillary teeth), or lower arch (e.g., mandibulary teeth). Accordingly in other embodiments the methods further comprise applying an intra-oral or extra-oral shade or mask to the patient. The intra-oral or extra-oral shade or mask can be applied prior to or concurrently with the administration of light.

Any time period can be provided between dosages of effective amounts of light. For example, the time period between dosages can be on the order of seconds, minutes, hours, days, weeks, months, quarter of a year, or years.

The effective amount, which in some embodiments is repetitive, can be administered with any desired frequency, e.g., four times daily, three times daily, twice daily, daily, every second day, weekly, biweekly, monthly, or quarterly. In some embodiments, dosage can be administered at regular intervals (e.g., daily), while in other embodiments, the dosage is not administered at regular intervals (e.g., administration can occur 2 times a week at any time during the week). In one embodiment, light can be administered in the morning and at night. Light can be administered throughout the time period that a patient is undergoing orthodontic treatment, or following treatment to stabilize tooth movement. For example, light can be administered after an appliance is applied, removed, adjusted, after an appointment, or after an active phase, as described herein. It can be desirable to administer light with greater frequency, e.g. four times daily, three times daily, twice daily, daily or every second day, while a patient is undergoing orthodontic treatment. Where light is being administered, for example, to stabilize tooth movement or reduce tooth-root resorption, treatments of reduced frequency, e.g. weekly, biweekly, monthly, or quarterly, can be used to minimize inconvenience to patients. In some embodiments, the effective amount of light maintains the ATP energy levels of tissue cells, e.g., ischemic tissue cells, to prevent cell death, as described above. In some embodiments, light is administered no less than about every second day. In some embodiments, a patient receives light treatment at least three or four times a week.

Light can be administered for any length of time. In some embodiments, light can be administered on the order of weeks, months, quarters, or years. For example, light can be administered while a heavy force is exerted on one or more teeth. One or more dosages of light can be administered over a period of time during which a heavy force is exerted on one or more teeth, during which a patient is wearing an orthodontic appliance that itself can exert a heavy force, or during which a patient is undergoing orthodontic treatment during which a heavy force may be applied. In some embodiments, while a patient is undergoing orthodontic treatment or is wearing an orthodontic appliance, a patient is administered with light. Administration of light, which may include regular, irregular, continuous or discontinuous administration of light, can be on the order of days, weeks, months, quarters, or years. In some embodiments, light is administered over a plurality of days, weeks, months, quarters, or years. In some embodiments, light is administered over a plurality of sessions. In some embodiments, one or more hours, days, weeks, months, quarters, or years occur between sessions.

If the light emitters are pulsed, then their duty cycle can be adjusted as desired; e.g., light can be administered with a duty cycle of about 10%, about 20%, about 30%, about 40%, about 50%, about 60%, about 70%, about 80%, or about 90%. The pulsing can occur with any frequency. For example, light can be pulsed every picosecond, nanosecond, microsecond, millisecond, second, multiple seconds, or minutes. Frequencies can include, but are not limited to, about 1 mHz, about 10 mHz, about 50 mHz, about 100 mHz, about 500 mHz, about 1 Hz, about 2 Hz, about 5 Hz, about 10 Hz, about 15 Hz, about 20 Hz, about 25 Hz, about 30 Hz, about 35 Hz, about 40 Hz, about 50 Hz, about 70 Hz, about 100 Hz, about 200 Hz, about 500 Hz, or about 1 kHz. Any of the aforementioned characteristics of light emission (e.g., whether the light is on or off, continuous or pulsed, duty cycle, frequency, intensity, wavelength) can be varied or maintained. Where the light is emitted from a source having a controller, any characteristics of light emission can be varied or maintained in accordance with instructions from its controller.

Where the light is emitted from one or more lights, light can be controlled so that the number of lights that are on or off at a given period can be individually controllable. For example, a light source can be turned on or off relative to other light sources. Various light sources can be modulated individually, to expose individual sections of a patient's maxillary and mandibular alveolar bone or other regions to a desired energy density. This can be desirable when it is desirable to administer light to different regions. Thus, the position of light being administered can be varied. In another embodiment, different types of light sources can be turned on or off relative to other light emitters. For example, at some times, light emitted in a first wavelength range can be turned on while light emitted in a second wavelength range can be turned off, vice versa, or both types of light emitters can be turned on or off. Thus, the wavelength of light being administered can be varied. In some embodiments, the intensity of light being administered can be varied (e.g., by turning some light sources on or off, or varying the intensity emitted by the light sources). Administering light selectively can enable an increased anchorage effect (by reason of lower tooth mobility) of teeth which are not exposed to any light, which can thereby permit for more precise movement of teeth to which light is administered.

In some embodiments, particularly where infrared light is administered to a patient, the present methods further comprise providing emission of a visible light c. In one embodiment the visible light is bright, e.g., uncomfortable for a patient to look at. The bright visible light can deter users or patients from looking into a light source when it is operating, can provide a perceptible indication that a light is being emitted, and can be useful in properly positioning a light source. The visible light can be, but is not necessarily, of a wavelength range that is beneficial for light therapy or regulation of tooth movement. In some embodiments, the ratio of the intensities of the visible and infrared components of the light is 1 part or less visible light to 5 parts or more infrared light. In some embodiments, light can be emitted within a range can include wavelengths less than an order of magnitude relative to one another. Alternatively, the range can include wavelengths emitted at one, two, three or more orders of magnitude relative to one another.

The region and desired light characteristics can vary from patient to patient. A physician, dentist or patient can determine a light treatment regimen for a patient. In some embodiments, he or she can use a light-therapy apparatus that administers light to provide the desired treatment.

In some instances, it can be desirable to administer light to less than all regions of the patient's maxillary or mandibular alveolar bone, for example, if it is desired that teeth in other regions do not need to be moved (e.g. it can be desired to regulate the movement of only the upper teeth of a patient, or only the lower teeth, or to use certain teeth as an anchor when regulating the movement of other teeth by administering no light to, e.g., blocking light from, the anchor teeth). Administering light to selected regions of the patient's maxillary or mandibular alveolar bone can comprise causing light to irradiate one or more selected tooth roots through the bone.

In one embodiment, light is selectively administered to less than all regions of the patient's mouth before, during, or after the exertion of heavy forces. In one embodiment, light is not administered to an anchor tooth. In this embodiment, an orthodontic appliance can be located between the anchor tooth and one or more other tooth. The orthodontic appliance can exert a force on another tooth. In some embodiments, the force is a heavy force. In some embodiments, an effective amount of light is administered to the other tooth and not to the anchored tooth. The administration of light can increase the velocity of the other tooth and reduce, minimize, or prevent root resorption of the other tooth, while not increasing the velocity of the anchor tooth.

It can also be desirable to administer light of different wavelengths to different regions of the patient's maxillary or mandibular alveolar bone, if it is desired to differentially manipulate the movement of a patient's teeth, as described below. For example, light of a first wavelength can be administered to a first region and light of a second wavelength can be administered to a second region. The first and second wavelengths can include any wavelengths described elsewhere herein, such as about 585 nm to about 665 nm, or about 815 nm to about 895 nm.

Light can be administered over an area. For example, light can be administered to a region with an area. In some embodiments, light characteristics can remain uniform over the area. In other embodiments, light characteristics can vary over the area. For example, light intensity can be uniform or can vary over an area of a region. The area of light administration can have any shape or size.

Light can be administered to a light irradiation area of any size and shape. For example, a region, such as a specified region of the patient's maxillary or mandibular alveolar bone, can have any size or shape. One or more dimensions of a light irradiation area can range from about 1 to about 80 mm, in another embodiment from about 1 to about 70 mm. In some embodiments, one or more dimensions (e.g., length, width, diameter) of a light irradiation area can range from about 1 to about 3 mm, about 3 to about 5 mm, about 5 to about 7 mm, about 7 to about 10 mm, about 10 to about 15 mm, about 15 to about 20 mm, about 20 to about 25 mm, about 25 to about 30 mm, about 30 to about 35 mm, about 35 to about 40 mm, about 40 to about 50 mm, about 50 to about 60 mm, or about 60 to about 80 mm.

A light-irradiation area can have any shape, which can include, but is not limited to, a substantially rectangular shape, square shape, triangular shape, hexagonal shape, octagonal shape, trapezoidal shape, circular shape, elliptical shape, crescent shape, cylindrical shape or half-circle. In some embodiments, the dimensions of a light source can be about the same as dimensions for a light irradiation area. In other embodiments, the dimensions of a light source can be greater than the dimensions of a light irradiation area. Alternatively, the dimensions of a light source can be less than the dimensions of the light irradiation area. The relative areas of a light source and light irradiation area can depend on any angle, which can be a parallel, convergence, or divergence angle, at which light is emitted.

In some embodiments, an effective amount of light can be provided in a treatment regimen. The treatment regimen can be used in the present methods.

In one embodiment, a typical treatment regimen provides a dose of light daily. Each of the daily doses of light can be administered over a period lasting from a few minutes to about an hour. For example, daily ½ hour doses of light can be effective and are not unduly inconvenient for patients. A single daily dose can be as effective as dividing the same dose into multiple sessions administered at different times during the day. Some treatment regimens can comprise administering light in 5 treatments per week for 12 weeks. Each treatment can last ½ hour and irradiate the tissues of a patient's jaw with light having wavelengths of 660 nm and 840 nm. The 660 nm light can have an intensity of about 20 mW/cm$^2$ at the skin's surface. The 840 nm light can have an intensity of about 10 mW/cm$^2$ at the skin's surface. These treatment regimens can enhance bone density.

Other treatment regimens can comprise administering light in daily treatments for 21 days. Each treatment lasts between 20 minutes and one hour and illuminates the tissues of a patient's jaw with light having a wavelength of 618 nm and an intensity of 20 mW/cm$^2$ at the skin's surface. These treatment regimens can accelerate healing of bone grafts.

Another treatment regimen can include a twice-daily administration of light for six months. In one embodiment the light is administered from a light-therapy apparatus. Light can be administered at a wavelength of about 660 nm or about 840 nm, or at both wavelengths. The intensity of the light can be about 20 mW/cm$^2$ at the skin's surface. An orthodontic appliance can be present in the patient's mouth while the light is administered. Subsequent to the first 6 month period, a second 6 month period can be provided where light is administered once every other day. The same orthodontic appliance or one or more different orthodontic appliances can be present in the patient's mouth at this time. The administration of light can optionally become less frequent or be administered at a lower intensity as treatment progresses.

Another treatment regimen can include administering light to a tooth having an orthodontic appliance and subsequently adjusting the orthodontic appliance. In some embodiments, adjusting an orthodontic appliance may increase or alter the magnitude of a force applied on one or more teeth. Adjusting an orthodontic appliance may alter the direction of a force applied on one or more teeth. Light can be administered to one or more selected teeth for up to an hour prior to adjusting an orthodontic appliance. Adjusting the orthodontic appliance can cause a heavy force to be exerted on the one or more teeth. Adjusting the appliance can change the magnitude or direction, or both, of the force exerted. Adjusting the appliance can comprise tightening, loosening or replacing one or more of the appliance's wires, springs or elastic devices. Different sizes, materials, or shapes of such components can be used. Light can then be applied daily to the one or more selected teeth, until the next adjustment of the appliance. This administration of light can reduce, minimize, or prevent tooth-root resorption, bone resorption, tissue inflammation, periodontium resorption or cementum resorption.

The present methods can further comprise controlling temperature of the patient's face or of any light source that is directed at or that contacts a patient's face or a region. For example, the method can include cooling, heating, or maintaining the temperature at a patient's face. A patient's face can be contacted with a temperature control mechanism, which can cause the removal or provision of heat. In some embodiments, heat can be generated by the light source. In some embodiments, the temperature of the light source can be controlled. A temperature control mechanism can communicate with the light source. Heat can be removed from or provided to the light source. Any embodiments for temperature regulation described herein can be used within the method. The method can further comprise measuring a temperature at a patient's face or at a light source. Temperature regulation can optionally occur in response to one or more temperature measurements made.

In one embodiment the present methods are performed prior to, subsequent to or concurrently with orthodontic treatment of a patient. In one embodiment the administration of light is repetitive.

An orthodontic treatment can cause one or more teeth to move or maintain its position relative to a supporting maxilla or mandible, or can include regulation of tooth movement. In some instances, orthodontic treatment can include aligning teeth. Orthodontic treatment can include treating malocclusion, which can occur when teeth fit together improperly, for example, as a result of their individual positions or positions of underlying jaw bone as they relate to one another. Malocclusion can be treated using light therapy or tooth movement regulation according to the methods described herein. Accordingly, the present invention further relates to methods for treating or preventing malocclusion, comprising allowing a heavy force to be exerted on one or more teeth of a patient in need thereof and extra-orally administering an effective amount of light to the maxillary or mandibular alveolar bone of the patient, where the light is administered before, during or after the heavy force is exerted. In another embodiment, methods for treating or preventing malocclusion comprise allowing a heavy force to be exerted on one or more teeth of a patient in need thereof and intra-orally administering an effective amount of light to the maxillary or mandibular alveolar bone of the patient, where the light is administered before, during or after the heavy force is exerted.

An orthodontic treatment can include the application of an orthodontic appliance to a patient. An orthodontic appliance can be present on one or more teeth of a patient. The methods can comprise installing an orthodontic appliance to a patient, such as installing the appliance to one or more teeth of the patient, adjusting an orthodontic appliance of the patient, or can comprise removing an orthodontic from the patient. Orthodontic treatment can include a period of time during which the orthodontic appliance is applied to the patient. In some embodiments, orthodontic treatment can include a period of time after the orthodontic appliance has been applied or removed from the patient. In some embodiments, orthodontic treatment can include a period of time preceding the application of an orthodontic appliance. In other embodiments orthodontic treatment includes a period of time prior to, during, or subsequent to the exertion of a heavy force on one or more teeth. Orthodontic treatment can include a period of time while a patient is seeing or consulting with an orthodontist.

In some embodiments, orthodontic treatment can include an active stage and a passive stage. An active stage can include some time during which an orthodontic appliance is applied to the patient. In some instances, an active stage can include a time during which a force is applied to a tooth to effect tooth movement. In some examples, the force applied to a tooth during an active stage is a heavy force. An active stage can include a period during which the patient is undergoing one or more adjustments to the patient's appliance. A passive stage can include a period after an appliance has been removed from the patient. In some instances, a passive stage can include a period during which an appliance is applied but is no longer undergoing adjustments. In some instances a passive stage can include a period during which an appliance is not providing force to effect movement of a tooth. Instead, the passive stage can include a period during which an appliance is applied to a patient and that maintains one or more teeth in its position. In some embodiments, any stage of orthodontic treatment can last on the order of days, weeks, months, quarters, or years.

In some embodiments, orthodontic treatment can result in bone remodeling. Force can be exerted on one or more tooth, any region of the jaw, or any other region of the mouth or head. Force can be exerted by an orthodontic appliance. In some embodiments, the force is a heavy force. Bone remodeling can involve altering the position or morphology of bone, including the jaw bone. For example, a jaw bone can be moved forward, or can be lengthened. In some embodiments, bone remodeling can occur in conjunction with regulating tooth movement. Accordingly, the present methods are useful for and in one embodiment result in bone remodeling. Light can be administered to a region, such as a region of a jawbone, or any oral bone or tissue, and is useful for bone remodeling. Accordingly, the invention further provides methods for inducing bone remodeling, comprising allowing a heavy force to be exerted on one or more teeth of a patient in need thereof and extra-orally or intra-orally administering an effective amount of light to the maxillary or mandibular alveolar bone of the patient, where the light is administered before, during or after the heavy force is exerted. Light therapy can be provided in conjunction with bone remodeling, and can increase the rate of bone remodeling. For example, applying an effective amount of light as described in the present methods can reduce the amount of time to achieve the same degree of bone remodeling without light by about 10%, about 20%, about 30%, about 40%, about 50%, about 60%, about 70%, about 80%, or about 90%. Light treatment can promote bone remodeling which can increase the rate of teeth movement. This can allow heavier forces to be used, which could accelerate tooth movement even more than with lighter forces. Such forces can be exerted by one or more appliances.

The present methods can be performed on a patient prior to being applied with one or more orthodontic appliances, during a time when the patient wears one or more orthodontic appliances, or after one or more orthodontic appliances has been removed from the patient. An orthodontic appliance can be fixed or movable with respect to a patient's teeth. Orthodontic appliances can include, for example, fixed active appliances such as pin and tube appliances, appliances using wires or brackets or springs, ribbon arch appliances, Begg lightwire appliances, edgewise appliances, pre-adjusted edgewise appliances, self-ligating edgewise appliances, bi-helix, tri-helix, quad-helix, rapid maxillary expansion appliance (RPE); removable active appliances such as expansion and labial segment alignment appliance INVISALIGN™; functional appliances such as herbst, bionator, frankel, biobloc, activator; orthodontic headgear including reverse headgear and conventional headgear; and other types of orthodontic apparatus. Orthodontic appliances are commercially available and can include specifications (or other documentation) that specify the magnitude of force that the appliance is capable of exerting on one or more teeth. In some embodiments, the orthodontic appliance comprises steel wires, nickel titanium wires, or titanium molybdenum wires. In some embodiments, the orthodontic appliance comprises wires or springs that are of a high gauge. Some examples of wires that an orthodontic appliance can comprise are stainless steel or nickel-titanium wires having wire dimensions of:

| | |
|---|---|
| 0.0160" square | 0.406 mm square |
| 0.0160" × 0.0220" | 0.406 mm × 0.559 mm |
| 0.0170" square | 0.432 mm square |
| 0.0170" × 0.0220" | 0.432 mm × 0.559 mm |
| 0.0170" × 0.0250" | 0.432 mm × 0.635 mm |
| 0.0180" square | 0.457 mm square |
| 0.0180" × 0.0220" | 0.457 mm × 0.559 mm |
| 0.0180" × 0.0250" | 0.457 mm × 0.635 mm |
| 0.0190" square | 0.483 mm square |
| 0.0190" × 0.0250" | 0.483 mm × 0.635 mm |
| 0.0200" square | 0.508 mm square |
| 0.0210" × 0.0250" | 0.533 mm × 0.635 mm |

Nickel-titanium closed or open-coil springs can be used. Some examples can include an elastomeric power chain, which can be capable of providing 100-800 grams of force, or intra-arch elastics. In some embodiments, the orthodontic appliance comprises an elastic material. An orthodontic appliance can exert a force on one or more teeth of the patient. In some embodiments, the orthodontic appliance can exert or be configured to exert a heavy force on one or more teeth of the patient. The orthodontic appliance can cause one or more teeth to move or maintain its position.

A heavy force can be measured using a dynamometer or any similar device. For example, a dynamometer can measure the force that a wire, spring or similar mechanism from an orthodontic appliance exerts on one or more teeth. The measured force can depend on any number of parameters such as, for example, the gauge of the wire or the stiffness of the wire. In this manner, in some embodiments, a heavy force can be calculated, in part, by measuring the tension or stiffness of the appliance's wire (or spring or similar mechanism), e.g., when such force is exerted on one or more teeth. Furthermore, in some embodiments, the appliance's wire (or spring or similar mechanism) is constructed from a material that is sensitive to temperature such that the stiffness of the wire, and therefore the heavy force exerted by that wire, can change based on the temperature of the wire. For example, in some embodiments, the stiffness of the wire (or spring or similar mechanism) increases when the wire temperature increases, and decreases when the wire temperature decreases. Thus, in some such embodiments, a heavy force can be calculated, in part, by measuring the temperature of the wire (or spring or similar mechanism) or estimating its temperature when present in a patient's oral cavity. With respect to the gauge of the wire, it is generally well known in the art that increasing the gauge (or cross-section) of a wire can increase the stiffness of the wire which ultimately increases the heavy force that the wire exerts on one or more teeth.

Installing, adjusting, or removing of an orthodontic appliance can occur before or after administering an effective dosage of light. In some embodiments, the effective amount of light can aid in regulating or accelerating the movement of teeth during orthodontic treatment with an orthodontic appliance. The effective amount of light can be useful for reducing the amount of time an orthodontic appliance is worn during an orthodontic treatment. For example, according to the methods of the present invention, the application of light can reduce treatment time (e.g., wearing orthodontic devices) by up to about 10%, about 20%, about 30%, about 40%, about 50%, about 60%, about 70%, about 75%, about 80%, about 85%, or about 90% of the treatment time. For example, administering light having a wavelength in the range of about 585 nm to about 665 nm (e.g., about 625 nm) can reduce the amount of time that a patient wears orthodontic appliances by about 5% to about 90%, for example, by about 5%, about 10%, about 20%, about 30%, about 40%, about 50%, about 60%, about 70%, about 75%, about 80%, about 85%, or about 90%. Administering light having a wavelength in the range of about 815 nm to about 895 nm (e.g., about 855 nm) can reduce the amount of time that a patient wears orthodontic appliances by about 5% to about 90%, for example, by about 5%, about 10%, about 20%, about 30%, about 40%, about 50%, about 60%, about 70%, about 75%, about 80%, about 85%, or about 90%.

Administering light having a wavelength in the range of about 585 nm to about 665 nm (e.g., about 625 nm) can result in a rate of tooth movement that is about 5% to about 90% faster than the rate of tooth movement without the administration of light. For example, the rate of tooth movement can be about 5%, about 10%, about 20%, about 30%, about 40%, about 50%, about 60%, about 70%, about 75%, about 80%, about 85%, or about 90%.

Administering light having a wavelength in the range of about 815 nm to about 895 nm (e.g., about 855 nm) can result in a rate of tooth movement that is about 5% to about 60% faster than the rate of tooth movement resulting from the administration of light having a wavelength in the range of 585 nm to about 665 nm (e.g., about 625 nm). For example, the rate of tooth movement can be about 5%, about 10%, about 20%, about 30%, about 40%, about 50%, about 55%, or about 60%.

Administering light having a wavelength in the range of about 815 nm to about 895 nm (e.g., about 855 nm) can result in a rate of tooth movement that is about 5% to about 95% faster than the rate of tooth movement without the administration of light. For example, the rate of tooth movement can be about 5%, about 10%, about 20%, about 30%, about 40%, about 50%, about 60%, about 70%, about 75%, about 80%, about 85%, about 90%, or about 95%.

Orthodontic treatments, particularly those that comprise the use of an orthodontic appliance, can exert heavy forces on one or more teeth. This can result in a rate of tooth movement that is about 5% to about 80% faster than the rate of tooth movement without the exertion of heavy forces. For example, the exertion of heavy forces in one or more teeth can increase the rate of tooth movement by about 5%, about 10%, about 20%, about 30%, about 40%, about 50%, about 60%, about 70%, about 75%, or about 80%.

In some embodiments, the administration of an effective amount of light can aid in reducing, preventing or minimizing tooth-root resorption when a heavy force is allowed to be exerted on one or more tooth. The effective amount of light can be useful for reducing the amount of tooth-root resorption as compared to when a heavy force is allowed to be exerted on one or more tooth without administering the effective amount of light. For example, according to the methods of the present invention, the administration of light can reduce tooth-root resorption by up to about 1%, about 2%, about 3%, about 5%, about 7%, about 10%, about 15%, about 20%, about 25%, about 30%, about 40%, about 50%, about 60%, about 70%, about 80%, or about 90%. Reducing tooth-root resorption, particularly while applying heavy forces, may allow for a reduction of the amount of time for orthodontic treatment, or the amount of time that a patient wears an orthodontic appliance. Administering an effective amount of light can reduce the amount of time that a patient wears orthodontic appliances by about 5% to about 90%, for example, by about 5%, about 10%, about 20%, about 30%, about 40%, about 50%, about 60%, about 70%, about 75%, about 80%, about 85%, or about 90%.

In some embodiments, administration of an effective amount of light can aid in reducing, preventing or minimizing bone resorption or inflammatory dentin or cementum resorption of the tooth root or periodontium. The effective amount of light can be useful for reducing bone resorption or inflammatory dentin or cementum resorption of the tooth root and periodontium, as compared to when a heavy force is allowed to be exerted on one or more teeth without administering the effective amount of light. For example, according to the methods of the present invention, the administration of light can reduce bone resorption or inflammatory dentin or cementum resorption of the tooth root or periodontium by up to about 1%, about 2%, about 3%, about 5%, about 7%, about 10%, about 15%, about 20%, about 25%, about 30%, about 40%, about 50%, about 60%, about 70%, about 80%, or about 90%. Reducing bone resorption or inflammatory resorption of dentin or cementum resorption of the tooth root or periodontium while exerting heavy forces can reduce the amount of time for orthodontic treatment, or amount of time that a patient wears an orthodontic appliance. Administering an effective amount of light can reduce the amount of time that a patient wears orthodontic appliances by about 5% to about 90%, for example, by about 5%, about 10%, about 20%, about 30%, about 40%, about 50%, about 60%, about 70%, about 75%, about 80%, about 85%, or about 90%.

In some embodiments, administration of the effective amount of light can aid in reducing, preventing or minimizing inflammation of tissue surrounding one or more teeth upon which heavy forces are or were exerted. The effective amount of light can be useful for reducing the amount of inflammation of tissue surrounding one or more teeth upon which heavy forces are or were exerted, as compared to when a heavy force is allowed to be exerted on one or more tooth without administering the effective amount of light. In one embodiment, according to the methods of the present invention, the administration of light can reduce inflammation of tissue surrounding one or more teeth upon which heavy forces are or were exerted by up to about 1%, about 2%, about 3%, about 5%, about 7%, about 10%, about 15%, about 20%, about 25%, about 30%, about 40%, about 50%, about 60%, about 70%, about 80%, or about 90%. Reducing inflammation of tissue surrounding one or more teeth upon which heavy forces are or were exerted while applying heavy forces can reduce the amount of time for orthodontic treatment, or amount of time that a patient wears an orthodontic appliance. Administering an effective amount of light can reduce the amount of time that a patient wears an orthodontic appliance by about 5% to about 90%, for example, by about 5%, about 10%, about 20%, about 30%, about 40%, about 50%, about 60%, about 70%, about 75%, about 80%, about 85%, or about 90%.

The light can be administered in accordance with a treatment regimen. In some embodiments, an orthodontic appliance can be installed prior to extra-orally or intra-orally administering the light, an orthodontic appliance can be installed concurrently with extra-orally or intra-orally administering the light, an orthodontic appliance can be installed subsequent to extra-orally or intra-orally administering the light, or any combination thereof. In some embodiments, an orthodontic appliance can be removed prior to extra-orally or intra-orally administering the light, an orthodontic appliance can be removed concurrently with extra-orally or intra-orally administering the light, an orthodontic appliance can be removed subsequent to extra-orally or intra-orally administering the light, or any combination thereof. In some embodiments, an orthodontic appliance can be adjusted prior to extra-orally or intra-orally administering the light, an orthodontic appliance can be adjusted concurrently with extra-orally or intra-orally administering the light, an orthodontic appliance can be adjusted subsequent to extra-orally or intra-orally administering the light, or any combination thereof.

The orthodontic appliance can exert a heavy force on one or more teeth of the patient. A heavy force can be exerted subsequent to, concurrently with, or prior to the administration of light. A heavy force may be exerted subsequent to, concurrently with, or prior to initiation of the administration of light. A heavy force can be exerted subsequent to, concurrently with, or prior to the initiation of a light treatment regimen. A heavy force can be exerted subsequent to, concurrently with, or prior to the initiation of a light treatment session. In some embodiments, a heavy force can be exerted one or more seconds, one or more minutes, one or more hours, one or more days or one or more weeks subsequent to administering the light and/or one or fewer days, one or fewer weeks, or one or fewer weeks subsequent to administering the light. The light can be administered for any length of time. In some embodiments, a heavy force is exerted one or more seconds, one or more minutes, one or more hours, one or more days or one or more weeks subsequent to initiating light administration and/or one or fewer days, one or fewer weeks, or one or fewer weeks subsequent to initiating light administration. In some embodiments, a heavy force can be exerted one or more seconds, one or more minutes, one or more hours, one or more days or one or more weeks subsequent to ending light administration and/or one or fewer days, one or fewer weeks, or one or fewer weeks subsequent to ending light administration.

Light can be administered for any period of time before, during, or after the exertion of a heavy force. For example, light can be administered for about 1 minute, about 2 minutes, about 3 minutes, about 5 minutes, about 10 minutes, about 15 minutes, about 20 minutes, about 30 minutes, about 45 minutes, about 1 hour, about 90 minutes, about 2 hours, about 3 hours, about 4 hours, or about 6 hours prior to, during, or after the exertion of a heavy force. In some embodiments, light is administered at any amount of time prior to, during, or after the initiation of the exertion of a heavy force. For example, light can be administered about 1 minute, about 2 minutes, about 3 minutes, about 5 minutes, about 10 minutes, about 15 minutes, about 20 minutes, about 30 minutes, about 45 minutes, about 1 hour, about 90 minutes, about 2 hours, about 3 hours, about 4 hours, about 6 hours, about 12 hours, about 1 day, about 36 hours, about 2 days, about 3 days, about 4 days, about 1 week, about 2 weeks, or about 1 month prior to, during, or after the initiation of the exertion of a heavy force.

Thus, a pretreatment of light may be effected prior to the exertion of the heavy force. In some embodiments, a heavy force may be exerted at one or more seconds, one or more minutes, one or more hours, one or more days or one or more weeks prior to administering the light and/or one or fewer days, one or fewer weeks, or one or fewer weeks prior to administering the light. Thus, a follow-up treatment of light can be provided after the exertion of the heavy force. In some embodiments, a heavy force is exerted during the administration of light, or at one or more stages of the administration of light.

In one embodiment, the effective amount can be in the range of about 24 J/cm$^2$ to about 200 J/cm$^2$, and can have a wavelength in the range of about 585 nm to about 665 nm, or about 815 nm to about 895 nm. Administration of light having a wavelength in the range of about 585 nm to about 665 nm is also useful in the present methods, in one embodiment, for promoting bodily movement of teeth or minimize tipping of teeth, or both. Administration of light having a wavelength in the range of 815 nm to about 895 nm, is also useful in the present methods, for example, for increasing the velocity of teeth through the patient's bone. In some other examples, an effective amount of light can have any of the light characteristics as described anywhere above. Teeth in a region of the patient's maxillary or mandibular alveolar bone to which light is not administered can be used as an anchor to facilitate movement of teeth in the selected region. In one embodiment the light is administered to the patient's face. In another embodiment, the light can be administered directly to a specific region of the patient's maxillary or mandibular alveolar bone.

In some embodiments, the present methods comprise administering to a patient in need thereof an effective dosage of light having a first wavelength to a selected first region of the patient's maxillary or mandibular alveolar bone, and further comprise administering an effective dosage of light having a second wavelength to a selected second region of the patient's maxillary or mandibular alveolar bone. In one embodiment the regulating occurs prior to, subsequent to or concurrently with orthodontic treatment of a patient. In one embodiment the effective amount of light having a first wavelength is a repetitive dosage. In another embodiment the effective dosage of light having a second wavelength is a repetitive dosage. Regions other than alveolar bone can receive the first or second wavelength of light. In one embodiment, the effective dosage of light can be in the range of 24 J/cm$^2$ to 200 J/cm$^2$. The first wavelength can be in the range of about 585 nm to about 665 nm, and the second wavelength can be in the range of about 815 nm to about 895 nm. In other examples, an effective amount of light can have any light characteristics as described anywhere above. In one embodiment the light is administered to the patient's face.

In some embodiments, the methods further comprise installing an orthodontic appliance, removing an orthodontic appliance or adjusting an orthodontic appliance. In other embodiments, the methods comprise administering light until orthodontic treatment is complete. Orthodontic treatment can be deemed complete after appointments with an orthodontic specialist are completed, after the movement of one or more teeth has been stabilized to substantially remain in the same position without the aid of an orthodontic appliance, or during a passive stage of orthodontic treatment as described in greater detail herein. Light can be administered to the region before, during, after, or any combination thereof, an orthodontic appliance is installed, adjusted, or removed. The orthodontic appliance can be applied, adjusted, or removed before, during, after, or any combination thereof, the application of light. In some embodiments, a heavy force can be exerted when the orthodontic appliance is installed or adjusted, or for a period of time following such installation or adjustment.

As described herein, the speed of tooth movement, e.g., through the bone, or the quality of that movement (e.g., "bodily" or "tipping" movement) can be regulated by administration of light. In one embodiment the present methods are useful for effecting bone regeneration, which can occur concurrently with the present methods. Bone regeneration can be enhanced by administering light according to the present methods. The light can be administered before, during or after orthodontic treatment. The light can be emitted from a light-therapy apparatus, such as described herein. Bone regeneration can include bone growth or bone resorption. This can include osteoblast or osteoclast activation. Tooth movement can require osteoclastic and osteoblastic activity. In one embodiment, the administration of light according to the present methods stimulates osteoclasts or osteoblasts and, accordingly, stimulates osteoclastic and osteoblastic activity. The administration of light can enhance bone regeneration that can accompany tooth movement.

For example, the present methods, in one embodiment for regulating tooth movement, can also comprise applying, adjusting or removing a tooth mask or other oral mask. A tooth mask can be applied or removed prior to, during, or after the administration of light. Light can be administered to a region before, during, after, or any combination thereof, an oral mask or tooth mask is applied, adjusted, or removed. In some embodiments, one or more of a patient's teeth can be at least partially covered with a tooth mask that can block at least some of the light. A tooth mask can block one or more wavelengths of light. In some embodiments, the tooth mask can completely block one or more wavelength of light, and in other embodiments, the tooth mask can reduce the amount or intensity of light reaching the teeth. In some embodiments, the intensity of the light administered to the teeth can be zero, or can be less than the intensity of the light emitted from a light source.

In accordance with another aspect of the invention, the present methods, in one embodiment for tooth-movement regulation, can regulate the bone regeneration. For example, the present methods can increase the rate of bone regeneration. In some embodiments, bone regeneration can facilitate tooth-movement regulation, for example, can increase the velocity or quality of movement, or can stabilize tooth movement. For example, bone regeneration can occur prior to, during or following tooth movement. Bone regeneration can include bone growth, bone strengthening or bone resorption. For example, during bone regeneration, bone mineral density (BMD) can increase, bone volume (BV) can increase, bone mineral content (BMC) can increase, and the ratio of bone volume to total volume (BV/TV) or bone density can increase. Higher BV/TV can indicate denser bone, where less bone regeneration can occur, which is desirable after tooth movement has occurred to enhance the stability of teeth. Other examples of parameters that can be affected during bone regeneration can include trabecular bone surface, bone quality, osteoclastic activity (e.g., osteoclast and preosteoclast counts), bone resorption. Light therapy can enhance existing cellular processes. Bone regeneration can occur in any bone tissue or oral region. For example, bone regeneration can occur in a portion or all of a maxillary alveolar bone, in mandibular alveolar bone, or around one or more teeth. In some embodiments, bone regeneration can occur around one or more teeth can, which can include a periodontium. In some embodiments, the region around one or more teeth can be within about 1 mm, about 2 mm, or about 3 mm from the surface of the teeth.

In some embodiments, light therapy according to the present methods can also result in treating or preventing jaw osteonecrosis. Accordingly, the present methods are useful for treating or preventing jaw osteonecrosis. Accordingly, the invention further provides methods for treating or preventing jaw osteonecrosis, comprising allowing a heavy force to be exerted on one or more teeth of a patient in need thereof and extra-orally or intra-orally administering an effective amount of light to the maxillary or mandibular alveolar bone of the patient, where the light is administered before, during or after the heavy force is exerted. Treating or preventing jaw osteonecrosis can comprise reversing osteonecrosis through the use of light therapy according to the methods described herein. Jaw osteonecrosis can occur with respect to any bone tissue. For example, jaw osteonecrosis can occur with respect to a portion or all of a maxillary alveolar bone, mandibular alveolar bone, or one or more teeth.

In some embodiments, light therapy according to the present methods can also result in reducing, minimizing, or preventing tooth-root resorption, bone resorption, inflammatory resorption of dentin or cementum resorption, or inflammation of tissue. Accordingly, the present methods are useful for reducing, minimizing, or preventing tooth-root resorption, bone resorption, inflammatory dentin or cementum resorption, or inflammation of tissue. Accordingly, the invention further provides methods for reducing, minimizing, or preventing tooth-root resorption, bone resorption, inflammatory dentin or cementum resorption, or inflammation of tissue, comprising allowing a heavy force to be exerted on one or more teeth of a patient in need thereof; and administering an effective amount of light to the maxillary or mandibular alveolar bone of the patient, wherein the light is administered before, during, or after the heavy force is exerted. Such methods may be used or useful in conjunction with heavy forces applied to one or more tooth.

In some embodiments, the region to which light is administered is any oral tissue, such as soft tissue or bone tissue. In some embodiments, the oral tissue is that on which oral surgery was performed. The present methods are useful for treating tissue after oral surgery. The oral surgery can be periodontal surgery or that relating to bone grafts. The oral tissue can be: a portion or all of tissue supporting one or more teeth, the gums, a maxillary alveolar bone, mandibular alveolar bone, or one or more teeth. Accordingly, the invention further provides methods for treating tissue after oral surgery, comprising allowing a heavy force to be exerted on one or more teeth of a patient in need thereof and extra-orally or intra-orally administering an effective amount of light to a region of the patient's oral tissue on which oral surgery was performed, where the light is administered before, during or after the heavy force is exerted. The present methods are also useful for increasing the rate of oral-tissue healing following oral surgery. Accordingly the invention further provides methods for increasing the rate of oral-tissue healing following oral surgery, comprising allowing a heavy force to be exerted on one or more teeth of a patient in need thereof and extra-orally or intra-orally administering an effective amount of light to a region of the patient's oral tissue on which oral surgery will be performed, where the light is administered before, during or after the heavy force is exerted. In some embodiments, the methods further comprise performing oral surgery on the oral tissue. The oral surgery can be performed prior to or subsequent to the administration of light therapy according to the present methods. In some embodiment, the region of light administration can be the alveolar bone. In some embodiments, the light administration occurs extra-orally, and light is transdermally administered to the region. In some embodiments, the light administration can occur intra-orally, and the light may be directly administered to the region. In some embodiments, the administration occurs for about 20 minutes. In some embodiments, the wavelength of administered light is about 625 nm. In some embodiments, the light may be administered following oral surgery, prior to oral surgery, or during oral surgery.

In other embodiments, the invention relates to methods for healing dental implants, for example, endosseous dental implants, or accelerating osseo-integration of endosseous dental implants, comprising allowing a heavy force to be exerted on one or more teeth of a patient in need thereof and extra-orally or intra-orally administering an effective amount of light to the maxillary or mandibular alveolar bone of the patient, where the light is administered before, during or after the heavy force is exerted. In other embodiments, the methods comprise intra-orally administering to a patient in need thereof an effective amount of light to a region of the patient's maxillary or mandibular alveolar bone. In one embodiment, these methods can be performed according to the teachings disclosed herein for the methods for regulating tooth movement.

In some embodiments, the present methods can further comprise applying a substance to a region, or in the proximity of a region, before, during, or after the administration of light. In some embodiments the methods can exclude the application of a substance to a region, or in the proximity of a region, before, during, or after the administration of light, or before, during, or after the exertion of heavy forces. In some instances, a substance can already occur at a region naturally. In some embodiments, the methods can optionally comprise applying a substance to at least a portion of the face overlying a region before, during, or after the administration of light. In some embodiments the methods for regulating tooth movement can exclude the application of a substance to at least a portion of the face overlying a region before, during, or after the administration of light. Optionally, light can be administered before, during, or after the administration of a substance. In some embodiments, light is administered only without the administration of a substance. The substance can enhance or inhibit the effects of the light administration. In one embodiment, the substance can be a visible-light- or infrared-light-absorbing substance, such as a dye. One or more light characteristics, such as wavelength, can be selected in response to the presence or application of the substance.

Light Therapy Systems

An aspect of the invention relates to light-therapy apparatuses. The light-therapy apparatuses are useful for providing light and, accordingly, useful in the present methods; for regulating movement of teeth; for reducing, minimizing or preventing tooth-root resorption; for reducing, minimizing or preventing bone resorption or inflammatory dentin or cementum resorption of a tooth root or periodontium; for reducing, preventing or minimizing inflammation of tissue surrounding one or more teeth upon which heavy forces are or were exerted; for performing craniofacial surgery; for performing oral or maxillofacial surgery; for performing orthognathic surgery; for bone regeneration; or for treating or preventing jaw osteonecrosis, periodontitis, or malocclusion. Apparatuses and systems as described herein can also be applied to treat a variety of conditions including: conditions treated by orthodontics, application of heavy forces to one or more teeth, stimulation and acceleration of healing after oral surgery or periodontal surgery, stimulation of the healing of wounds at the locations of bone grafts, healing and acceleration of osseo-integration of endosseous dental implants; or any other applications as described elsewhere herein. In one embodiment, the application to jaw osteonecrosis permits treatment of a condition for which existing treatments are highly invasive. Treating osteonecrosis using light therapy is significantly more cost-effective and comfortable for the patient than existing surgical treatment options. A light-therapy apparatus useful for methods of regulating tooth movement and other methods described herein, can have other effects. For example, extra-oral application of light on the condylar portion of the mandible can increase the growth of the mandible in orthopedic expansion and growth treatments.

A light therapy system is provided and comprises a light-therapy apparatus. A light therapy system can also optionally comprise an oral appliance, such as an orthodontic appliance, or oral or tooth mask. Any orthodontic appliance, as described anywhere above, can be part of the light therapy system. An oral or tooth mask can block or partially filter one or more wavelength of light from a region covered by the mask. For example, a tooth mask can cover one or more teeth. The tooth mask can cover one or more mandibular or maxillary tooth. An oral mask can cover any region of the mouth. For example, an oral mask can cover one or more teeth, or one or more portion of the gums. An oral mask or tooth mask can be formed of a transparent, translucent, or opaque. An oral mask or tooth mask can block all wavelengths, reduce the intensity of all wavelengths, filter only some wavelengths, or reduce the intensity of only some wavelengths. In some embodiments, an oral mask or tooth mask can alter one or more light characteristics.

A light therapy system can also optionally include an external controller or a computer (or any other device described below) in communication with a controller.

Any embodiments of a light-therapy apparatus as described herein can be incorporated within the light therapy system. The light-therapy apparatus can optionally comprise one or more support features that can engage with a portion of a patient's face or head. In another embodiment the light-therapy apparatus engages with the mouth of the patient. The light-therapy apparatus can also comprise one or more light sources, wherein the one or more light sources can each comprise one or more light emitters. The light therapy system can also comprise a controller that controls the operation of the light-therapy apparatus. The controller can control the wavelength, intensity or duration of light emitted by the light-therapy apparatus or the position of its components. The controller can control any other light characteristics. The controller can be integral to or separate from the light-therapy apparatus. The light therapy system provides light and, accordingly, is useful in the present methods.

In some embodiments, a light therapy system comprises one or more other appliances. For example, an orthodontic appliance can be applied within an oral cavity of the patient. In another embodiment, an oral mask or tooth mask can be applied within the oral cavity of the patient. A light therapy system can include oral appliances or inserts that are within the oral cavity of the patient.

The light-therapy apparatus can be fixed or movable with respect to the orthodontic appliance, oral or tooth mask, or any other appliance.

Figure 2:
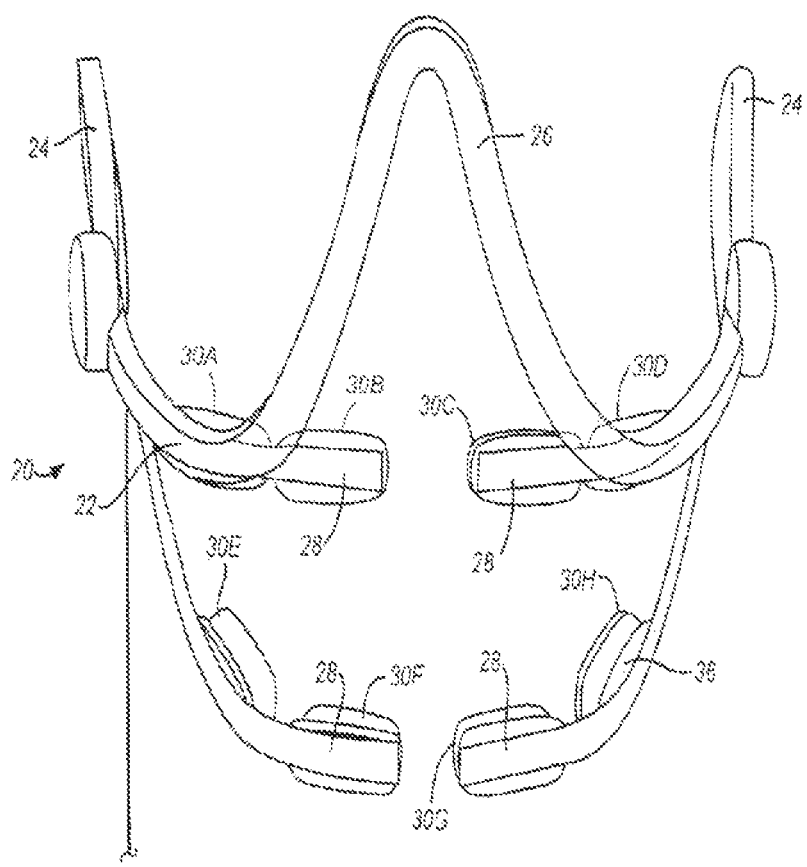
FIG. 2 is a front view of the embodiment shown in FIG. 1.
Figure 3:
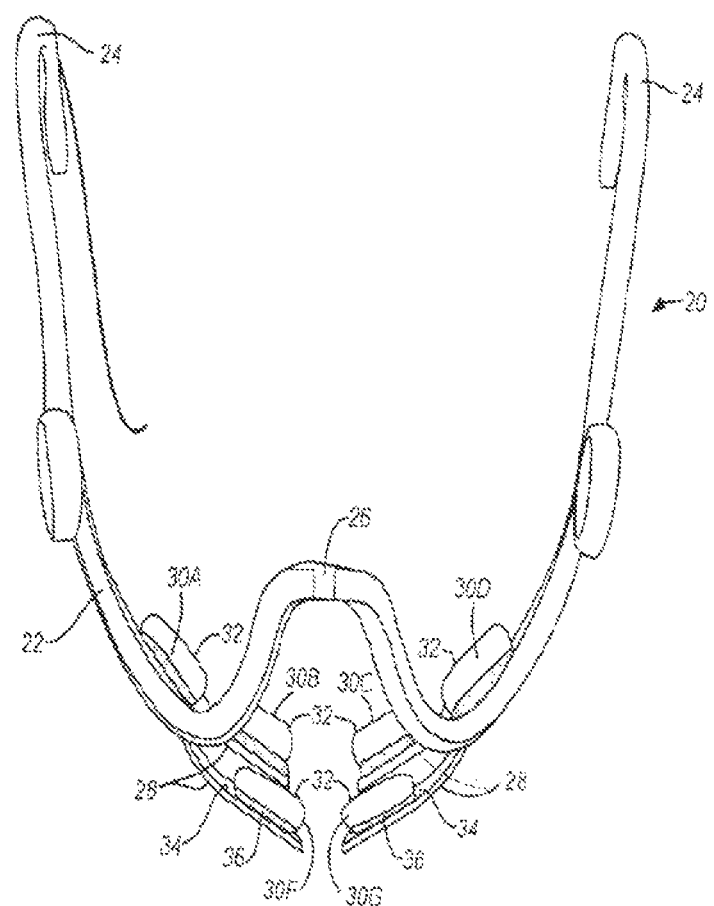
FIG. 3 is a top view of the embodiment shown in FIG. 1.
Figure 4:
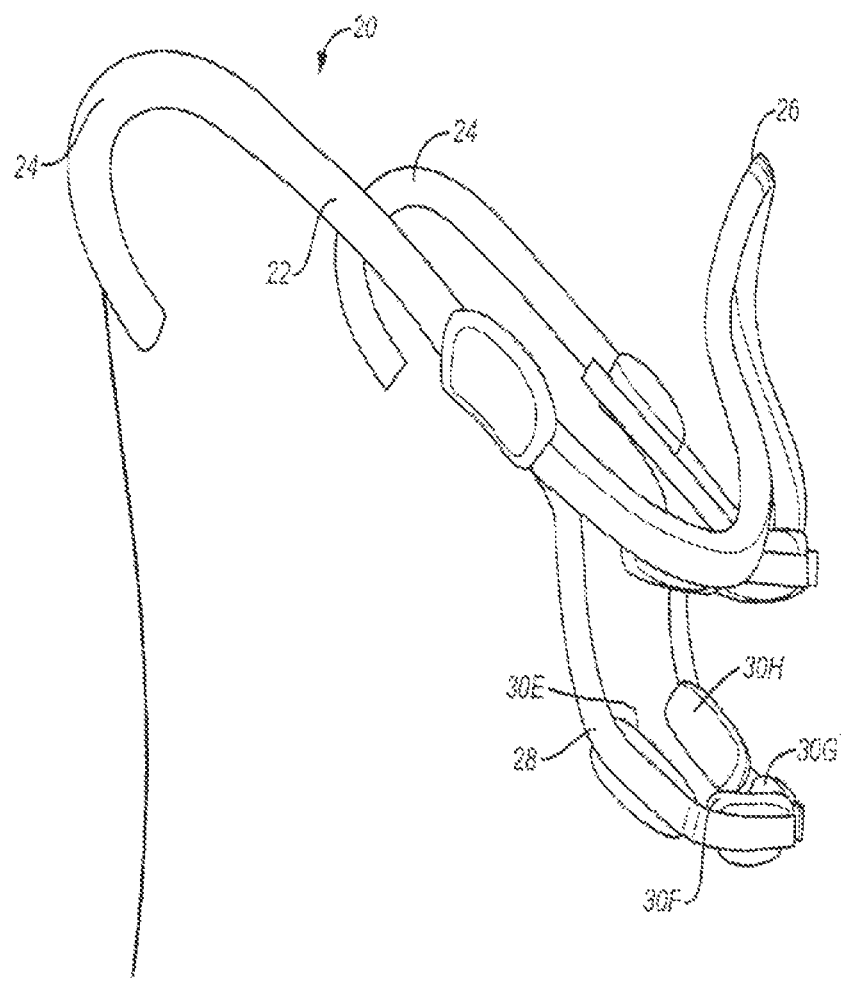
FIG. 4 is a right isometric view of the embodiment shown in FIG. 1.

An embodiment of an orthodontic light-therapy apparatus 20 is shown in FIGS. 1-4. FIG. 1 is an isometric view of an embodiment of a light-therapy apparatus useful for providing light to one or more specified regions of a patient's maxillary or mandibular alveolar bone. FIG. 2 is a front view of the embodiment shown in FIG. 1. FIG. 3 is a top view of the embodiment shown in FIG. 1. FIG. 4 is a right isometric view of the embodiment shown in FIG. 1. The light-therapy apparatus can be useful for providing light to any region described anywhere above.

Light-therapy apparatus 20 has a frame 22 which is sized and shaped to engage with one or more features of a patient's face. Features of a patient's face can include, but are not limited to, the patient's ears, nose, nostrils, mouth, lips, chin, jaw, cheek, brow, or forehead. The light-therapy apparatus 20 can have a frame 22 that optionally engages with other features of a patient's head or portion of their anatomy. For example, the frame can engage with the crown of the patient's head, the top or back of the patient's head, the neck, or shoulders.

In the illustrative embodiment illustrated in FIGS. 1-4, frame 22 is shaped to provide ear-engaging portions 24, a nose-engaging portion 26, and support arms 28. A frame can engage with features of a patient's face by conforming to the shape of the feature, wrapping around the feature, overlying the feature, grasping the feature, adhering to the feature or providing pressure or weight to the feature. In some embodiments, frame 22 is formed as an integral unit. In other embodiments, frame 22 is formed from two or more separate pieces of material, which are suitably joined to provide frame 22. In some embodiments, frame 22 includes more than one type of material; for example, support arms 28 can be made from a material that is different from other portions of frame 22. Alternatively, the frame 22 can be formed of the same type of material.

Support arms 28 can be disposed so that they are overlying and contacting a patient's face, directly over the patient's jawbone when light-therapy apparatus 20 is worn in a use configuration by a patient. Portions 24 and 26 facilitate retention of light-therapy apparatus 20 on the facial area of a patient, while support arms 28 support a plurality of light sources 30 (also shown as light sources 30A-30H in some figures), as described below. Support arms 28 can also facilitate engagement of light-therapy apparatus 20 on the facial region of a patient, e.g., by providing a biasing force inwardly against a patient's face. Other suitable configurations of frame 22 in addition to the illustrated embodiment are useful for securing light-therapy apparatus 20 to a patient's face and to support light sources 30 at the desired locations and with the desired orientations. The frame can support one or more light sources so that they contact the patient's face. The frame can be positioned so that the light source contacts the skin of a portion of the face overlying the region.

The frame 22 can include one or more support arms 28 that can be formed of an elongated portion. The support arms can be straight, curved, or bent in order to engage with a patient's face as desired. In some instances, the frame 22 includes other shaped portions that can include surfaces that can be flat, curved, or bent, that can cover one or more portion of the face. In one embodiment, the frame 22 can be curved over the bridge of a patient's nose, or curved around their ears. The frame can curve around the mouth or around a portion of the mouth.

FIG. 2 provides an example of a frame 22 where four elongated support arms extend around the mouth. For example, one, two or more support arms can be provided below the mouth. The support arms can be configured to lie over the patient's face, directly above the patient's jaw. One, two or more elongated support arms can be provided above the mouth or below the nose. The support arms can form two tracks, an upper track above the mouth, and a lower track below the mouth. In another embodiments, only one track is provided, which can be above the mouth, below the mouth, or in line with the mouth. Alternatively, additional tracks can be provided; for example, multiple support arm tracks can be provided above the mouth, below the mouth, or in line with the mouth. The support arms can lie over a right side or a left side of the patient's face. In some embodiments, an elongated support arm can form a continuous piece lying over both a right side and left side of a patient's face. Alternatively, separate elongate portions can be provided for a right side and left side of a patient's face. Elongate portions can optionally overly a central region of the patient's face. In some embodiments, elongate portions do not overly a central region of the patient's face. Any description herein of elongated support arms can also apply to support arms or other portions of the frame 22 that can have other shapes. Any arrangement of support arms can be applied to any of the light-therapy apparatus embodiments described herein.

In some embodiments, a support arm can include a support feature. In some embodiments, at least one of a right side of the support or left side of the support can comprise a support feature. In some embodiments, both the right and left side of the support can comprise support features. A support feature can allow one or more component of the light-therapy apparatus to removably engage with the support. In some embodiments, the support feature can allow the one or more components to move relative to the support while being engaged with the support. In some embodiments, the one or more components can comprise a light emitter, a light source, a secondary support, a hinge, or a light assembly. The support feature can be a track. In some embodiments, a track can include a slot, channel, groove, or other female feature which can be configured to accept a protrusion, ridge, or any other male feature, which can be provided on a component, such as a light source, a secondary support, a hinge, or a light assembly. In one embodiment, the track can be formed on an inner surface portion of the support (e.g., side of the support closer to a patient's face when in use). Alternatively, the track can be provided on an outer surface portion of the support (e.g., side of the support further from the patient's face when in use). In some embodiments, the track can be provided through the support. Alternatively, a support feature, such as a track, can have male features that can engage with a female feature of a component. Interlocking features can be provided between the support and one or more component.

FIGS. 8A-8D show another embodiment of a light-therapy apparatus 80. The light-therapy apparatus 80 can have a frame 82 which is sized and shaped to engage with features of a patient's face. The frame 82 can optionally be shaped to engage with features of a patient's head or another portion of the patient's anatomy. Alternatively, the frame 82 is not shaped to engage with other features of the patient's head or other portions of the patient's anatomy.

In some embodiments, the frame 82 can be shaped to provide ear engaging portions, a nose engaging portion 86, and support arms 88. In some embodiments, the frame 82 can be formed as an integral unit. For example, the ear engaging portions, the nose engaging portion, and the support arms can be formed of a continuous integral unit. In one instance, the ear engaging portions, the nose engaging portion, and the support arms can form a single continuous elongated piece. In other embodiments, frame 82 can be formed from two or more separate pieces of material, which are suitably joined to provide frame 82. In some embodiments, one support arm per side of the face can be provided. Alternatively, multiple support arms per side of the face can be provided. One or more support arm can be engaged with the nose engaging portion or ear engaging portion.

Support arms 88 can be disposed so that they are adjacent to a patient's face overlying the jawbone or so that they are in the proximity of a patient's jawbone when light-therapy apparatus 80 is worn in a use configuration by a patient. In some embodiments, the support arms can be positioned so that one more light source 81 can contact the patient's face over the patient's jawbone or contact any other selected region of a patient's face. Portions, such as an ear engaging portion, nose engaging portion 26, or any other portion of a frame that can engage with features of a patient's face, can facilitate retention of light-therapy apparatus 80 on the facial area of a patient, while support arms 88 supports one or a plurality of light sources 81 (also shown as light sources 81A-81D in some figures), as described below. Support arms 88 can also facilitate engagement of light-therapy apparatus 80 on the facial region of a patient, e.g., by providing a biasing force inwardly against a patient's face. Other suitable configurations of frame 82 in addition to the illustrated embodiment could be used to secure light-therapy apparatus 80 to a patient's face and to support light sources 81 at the desired locations and with the desired orientations. Other features, configurations, or components, as described in other embodiments, can be incorporated within this embodiment.

A frame, for any embodiment of a light-therapy apparatus, can be constructed from any suitable material; for example, lightweight plastic, steel, aluminum, copper, copper clad materials (such as aluminum or steel), nickel, titanium, silver, iron, other suitable metal or plastic, tubular plastic, plastic composite embedded with metal particles, graphite, graphite-epoxy, or any combinations or alloys thereof. The frame or portions of frame can optionally include a resin covering or suitable padding to cushion a patient's face. The frame can be made from flexible material, or from material which is thermally conductive. If a frame is made from a thermally conductive material such as, for example, aluminum, the frame can be capable of dissipating heat from one or more light sources, described below.

A frame can be made from a material which provides the frame with flexibility or which permits the frame to be conformed to the anatomical features of a particular patient's face. The frame or other components of the light-therapy apparatus can be bent in one or two dimensions. They can be moldable to conform to contours of the patient's face. A physician, dentist, orthodontist, therapist, technician or other individual, including a patient, can initially "fit" a particular light-therapy apparatus to a particular patient by adjusting and conforming that particular light-therapy apparatus to the anatomical features of that particular patient to provide an individualized fit. The material of which the frame is constructed can be sufficiently resilient to retain the individualized fit over the course of orthodontic therapy for that particular patient, and yet sufficiently flexible to permit that particular light-therapy apparatus to be re-adjusted (e.g. in response to complaints of discomfort from a patient) or adjusted to fit a different patient.

Any description, components, features, details of an embodiment of a light-therapy apparatus can be applied to any other embodiment of a light-therapy apparatus, and vice versa. For example, modifications to any device of FIGS. 1-4 (e.g., a frame 22 or light source 30 as provided in FIGS. 1-4) can be made to any of FIGS. 8A-8D (e.g., frame 82 or light source 81 in FIGS. 8A-8D), FIG. 9, FIG. 14, FIG. 17, or FIG. 18.

Providing a flexible frame 22 can also facilitate light source 30 contacting the cheek of a patient by support arms 28 (i.e., support arms 28 can bias light source 30 against the desired region of light administration on a patient's face, directly over his or her jawbone). In some embodiments, the morphology of the frame or the support arms, can cause the light source to contact a portion of a patient's face when the light-therapy apparatus is in use, e.g., when the light-therapy apparatus is worn by a patient. Other features can bias the light source, e.g., by providing pressure, to contact a portion of the patient's face, including but not limited to, elastic components, springs, inflatable portions, moving mechanical portions. Such bias can be provided when the patient's face is relaxed or when the patient's face is tensed. Bias of light source 30 on the cheek of a patient can depress the soft tissue, which can increase the effective transmission of light through the tissue. Thus, in some embodiments, it can be desirable for a light source to contact the skin of a patient's face or depress the skin of the patient's face.

In other embodiments, a gap can be provided between a light source and a skin of the patient's face. The frame can be configured to provide the gap between the light source and the patient's face. The light source can be in close proximity to the skin of the patient's face without contacting the patient's face. In some embodiments, the light source does not contact a patient's face when the patient's face is relaxed but can contact the face if the patient flexes a portion of the patient's face or tenses the face. In some embodiments, a light source can be about 1 mm or less, 2 mm or less, 3 mm or less, 5 mm or less, 7 mm or less, 1 cm or less, 1.5 cm or less, 2 cm or less, 2.5 cm or less, 3 cm or less, or any distance described anywhere above, away from a patient's face while the patient's face is relaxed.

In some embodiments, the light source can contact a translucent or transparent material, such as a gel or solid film that contacts the patient's face. The frame can be configured so that the translucent or transparent material contacts the patient's face when the apparatus is in use. In some embodiments, the light source can include an exterior surface formed of a translucent or transparent material, such as a gel or solid film that contacts the patient's face. One or more light emitters of the light source can contact that exterior surface. Alternatively, a gap can be provided between the light emitters and the exterior surface. In some embodiments, the translucent or transparent material filters light of one or more particular wavelengths. In some other embodiments, the material dissipates heat generated by operation of the light source.

In some embodiments, a light emitter provided on a light source can be positioned at a distance from a region. The frame can be configured so that the light source is at a distance from the region. The region can be within a patient's oral cavity. In some embodiments, the light emitter can be provided external to the oral cavity. A portion of a patient's face, such as the cheek, lips, or chin can be lie between the light emitter and the oral cavity when the device is in use. A light emitter can be positioned at about 0.1 mm or less, about 0.5 mm or less, about 1 mm or less, about 2 mm or less, about 3 mm or less, about 5 mm or less, about 7 mm or less, about 1 cm or less, about 1.5 cm or less, about 2 cm or less, about 2.5 cm or less, about 3 cm or less, or any distance described anywhere above, from a region.

Optionally, regions of greater flexibility than the remainder of frame can be provided between light sources or at other suitable locations on frame, to allow frame to be bent to provide a better fit around the facial area. Regions of greater flexibility can be provided, for example, by forming the region of greater flexibility from a portion of material that is thinner than the remainder of frame, by forming the region of greater flexibility from a material that is more flexible than the remainder of frame, or by providing hinge-like members (e.g., a thin crease or other bend line set into the material of which frame is constructed) within the frame. Other examples of how flexibility can be provided, can include using a bendable material, using a stretchable elastic material, using a spring, including multiple components that can slide or move relative to one another, that can unfold relative to one another, using telescoping features, including one or more joint (e.g., ball and socket, hinges), or having parts that can lock to one another at different size options. The frame can be adjustable to fit patients with different sized or shaped heads. In some instances, a frame size can be selected based on the size or shape of a patient's head.

In some embodiments, at least one light source 30 is secured to frame 22 in order to emit light towards a patient when light-therapy apparatus 20 is in the use position. Light source 30 is disposed extra-orally, i.e., outside of a patient's oral cavity, when light-therapy apparatus 20 is in the use position. When in use, the light source irradiates through the skin of a patient's face. Light can reach a region that is within a patient's oral cavity by transcutaneously irradiating through the skin. In some embodiments, when in use, light from a light source 30 is not configured to directly irradiate into the oral cavity, and reaches the oral cavity only through the skin. In one embodiment, light can reach a region only transdermally.

A light-therapy apparatus can have one or more light source capable of emitting light in the wavelengths described below or described anywhere above. The light provided by the light source is not necessarily visible light—any desired wavelength can be used. For example, light emitted by the light source can include infrared light or near-infrared light. The light source can also irradiate in the visible light region. For example, the light source can be configured to irradiate light falling within or ranging from about 400 nm to about 1200 nm. In particular embodiments, the light source can be configured to irradiate light falling within or ranging from about 500 to about 700, about 585 nm to about 665 nm, about 605 nm to about 630 nm, about 620 nm to about 680 nm, about 815 nm to about 895 nm, about 815 to about 895 nm, about 820 nm to about 890 nm, about 640 nm to about 680 nm, or about 740 nm to about 780 nm. In some embodiments, the wavelengths can fall within or range from about 605 nm to about 645 nm, or from about 835 nm to about 875 nm. In some embodiments, the wavelengths can fall within or range from about 615 nm to about 635 nm, or from about 845 nm to about 865 nm. In some embodiments, the wavelengths can be about 625 nm or about 855 nm. In some embodiments, a light source can be configured to emit light at one, two, or more of the light ranges described. In some instances, a light source does not emit light outside one, two, or more of the light ranges described. In other embodiments, light emitters can be configured to irradiate light having other wavelengths, as desired for a particular application. Light can be emitted at any of the wavelengths described anywhere above.

In some embodiments a light source can be capable of emitting light at one, two, or more peak wavelengths of emission. A peak wavelength can be the wavelength at which the highest intensity of light is emitted. In some embodiments, light can be emitted at a range of wavelengths and the peak wavelength can be the wavelength with the highest intensity within the range. In some embodiments, a peak wavelength can be provided at about 620 nm, about 640 nm, about 650 nm, about 655 nm, about 660 nm, about 665 nm, about 670 nm, about 680 nm, about 690 nm, about 800 nm, about 820 nm, about 830 nm, about 835 nm, about 840 nm, about 845 nm, about 850 nm, about 860 nm, about 870 nm, or about 890 nm. The light can have any other wavelength characteristics as described anywhere above.

A light source can be any suitable light source, which can include one, two, three, four, five, six, seven, eight, or more light emitters. In some embodiments, a light source comprises about 10 to about 15 emitters, about 15 to about 20 emitters, about 20 to about 30 emitters, about 30 to about 40 emitters, about 40 to about 50 emitters, about 50 to about 70 emitters, or about 70 emitters to about 100 emitters. For example, a light source can comprise a light-emitting diode (LED) (e.g., gallium arsenide (GaAs) LED, aluminium gallium arsenide (AlGaAs) LED, gallium arsenide phosphide (GaAsP) LED, aluminium gallium indium phosphide (AlGaInP) LED, gallium(III) phosphide (GaP) LED, indium gallium nitride (InGaN)/gallium(III) nitride (GaN) LED, or aluminium gallium phosphide (AlGaP) LED), which can be present in an array; or a laser, for example a vertical cavity surface emitting laser (VCSEL) or other suitable light emitter such as an Indium-Gallium-Aluminum-Phosphide (InGaAlP) laser, a Gallium-Arsenic Phosphide/Gallium Phosphide (GaAsP/GaP) laser, or a Gallium-Aluminum-Arsenide/Gallium-Aluminum-Arsenide (GaAlA5/GaAs) laser. In one embodiment the light source comprises a plurality of lasers. A plurality of light emitters capable of emitting light at several different wavelengths can be used for light source 30. Alternatively, one or more light emitters capable of emitting light at the same wavelength can be used for the light source. One or more light emitters can be arranged on a light source in any manner. For example, a plurality of light emitters can be arranged in one or more rows or columns. The rows or columns can form an array, or a staggered set of rows or columns, concentric shapes. Light emitters can be provided from any commercially available source, and can include but are not limited to Optowell XH85 vcsel, ULM Vcsel, or Osram MIDLED.

A light source 30 can be of any size and shape useful to irradiate through a patient's face a specified region of the patient's maxillary or mandibular alveolar bone. For example, in some embodiments, the light source 30 can have a height of about 9-10 mm along a vertical axis tangential to a patient's face, and a width in the range of about 15-18 mm along a horizontal axis tangential to a patient's face, as measured when light-therapy apparatus 20 is in the use configuration. One or more dimensions of a light source range from about 1-70 mm. In some embodiments, one or more dimensions of a light source range from about 1-3 mm, about 3-5 mm, about 5-7 mm, about 7-10 mm, about 10-15 mm, about 15-20 mm, about 20-25 mm, about 25-30 mm, about 30-35 mm, about 35-40 mm, about 40-50 mm, or about 50-60 mm.

A light source can have any shape, which can include, but is not limited to, a substantially rectangular shape, square shape, triangular shape, hexagonal shape, octagonal shape, trapezoidal shape, circular shape, elliptical shape, crescent shape, cylindrical shape or half-circle. A light source can have rounded or pointed corners. In some embodiments, the dimensions of a light source can be about the same as dimensions for a region area. In other embodiments, the dimensions of a light source can be greater than the dimensions of a region area. Alternatively, the dimensions of a light source can be less than the dimensions of the region area. The relative areas of a light source and region can depend on a parallel, convergence, or divergence angle at which light is emitted.

In some embodiments, each of the light sources within a light-therapy apparatus can be the same size or shape. In other embodiments, the light sources can have different sizes or shapes. Light source size or shape can be selected to administer a desired distribution of light to a region. A light source can have one type of light emitter. Alternatively, a light source can have two, three, four, five, or more different types of light emitters. Each light source can have a different light emitter or combination of light emitters, or can have the same light emitter or combination of light emitters. For example, each light source can have LEDs emitting light within the range of about 585 nm to about 665 nm, and LEDs emitting light within the range of about 815 nm to about 895 nm. In another embodiment, a first light source can have LEDs emitting from about 585 to about 665 nm, while a second light source can have LEDs emitting from about 815 to about 895 nm.

In some embodiments, one or more light source can include a substrate supporting the one or more light emitters. For example, one or more light source can comprise an array of light emitters mounted on a flexible sheet of material that will hold a shape when it is bent. The flexible material can advantageously comprise a metal sheet that can serve as a heat sink or thermal path to a heat sink. The flexible sheet can be molded to conform to the contours of a patient's face while the light-therapy apparatus is being fitted or is in use. The substrate can also include a cushioned material that can contact a patient's face without causing discomfort.

In some embodiments, light emitters of different characteristics (e.g., wavelength, intensity, pulsing, size), can be provided for a light source. In some instances, the different light emitters can be evenly interspersed within a light source. For example, light emitters of a first wavelength can be evenly interspersed within light emitters of a second wavelength. Alternatively, different light emitters can be localized. For example, light emitters of a first wavelength can be provided within a first region of a light source, and light emitters of a second wavelength can be provided within a second region of the light source.

A plurality of light sources 30 can be disposed on frame 22 to administer light of the desired wavelength substantially uniformly to desired regions of a patient's face, so as to irradiate, in one embodiment through the face, the patient's maxillary or mandibular alveolar bone, or any other region as described elsewhere herein. Any number of light sources can be disposed on a frame. For example, one, two, three, four, five, six, seven, eight, nine, ten, eleven, twelve, thirteen, fourteen, fifteen, sixteen, seventeen, eighteen, nineteen, twenty, or more light sources can be provided for a light-therapy apparatus. The light sources can be distributed along any portion of the frame. In some embodiments, the same number of light sources can be provided on the right side and the left side of the frame. Alternatively, different numbers of light sources can be provided the right and left sides of the frame. One, two, three or more light sources can be positioned to administer light to a region. In some embodiments, the light administered by light sources to a particular region can be the same for each light source, or can vary.

One or more of the light sources can be removable. In some embodiments, all of the light sources are removable, while in other embodiments, one or more of the light sources are not removable. In some instances, none of the light sources are removable. Different types of light sources can be used to provide a desired light with a desired distribution to a region. For example, different light sources can be used for different applications, such as different stages of orthodontic treatment. For example, a first light source providing light at a first wavelength range can be used for one purpose, and a second light source providing light at a second wavelength range can be used for the same or for a different purpose. Or a first light source having a first size or shape can be used instead of or in conjunction with a second light source having a second size or shape. Additional light sources can be added or removed. Different light sources can be added or removed during the course of a treatment, such as an orthodontic treatment, bone regeneration treatment, or any of the other treatments disclosed herein, or during the course of preventing one or more abnormal conditions disclosed herein.

Each individual light source 30 can be separately configured or separately controllable, to provide light of a specified wavelength or intensity to a specific region of a patient's jawbone, or any other region for a desired period. In one embodiment the light is provided through the patient's face.

In some instances, one or more groups or subgroups of light sources can be separately configured or separately controllable, while all light sources belonging to the group or subgroup provide light of the same wavelength or intensity. In another implementation, all light sources belonging to a light-therapy apparatus can be controlled together.

In some embodiments, a light-therapy apparatus can be configured to administer light to only some regions of the patient's maxillary or mandibular alveolar bone, if it is desired that teeth in other regions do not need to be moved (e.g. it can be desired to move only the upper teeth of a patient, or only the lower teeth, or to use certain teeth as an anchor when moving other teeth by administering no light to the anchor teeth). The light-therapy apparatus can also be capable of providing light of different wavelengths to different regions of the patient's maxillary or mandibular alveolar bone, if it is desired to differentially manipulate the movement of a patient's teeth, as described below. For example, light of a first wavelength can be administered to a first region and light of a second wavelength can be administered to a second region. The first and second wavelengths can include any wavelengths described elsewhere herein, such as about 585 nm to about 665 nm, and about 815 nm to about 895 nm, respectively.

In some embodiments, light can be administered to a region that can include a portion of tissue (e.g., bone tissue, or soft tissue) or other regions within the patient's oral cavity without being administered to other portions of the patient's oral cavity. In some embodiments, light can be administered to a region that can include a portion of tissue (e.g., bone tissue, or soft tissue) or other regions within the patient's oral cavity at a much greater intensity than it is administered to other portions of the patient's oral cavity. For example, 3×, 5×, 10×, 20×, 50×, or 100× greater intensity of light can be administered to a region, than another portion of the patient's oral cavity. In some embodiments, this is achieved by applying to the patient one or more intra-oral or extra-oral light-translucent or light-opaque masks that shield from light one or more non-regions. In some embodiments, light reaching a region can have an intensity that is greater than a threshold value. In some embodiments, the threshold value can be at an intensity as described elsewhere herein.

A patient can position light-therapy apparatus 20 herself or himself to accurately and repeatedly illuminate a desired location in the patient's dental and maxillofacial areas when light-therapy apparatus 20 is in a use position. Consistent positioning of light-therapy apparatus 20 during the course of a patient's treatment can make therapy more effective and repeatable, and ease of use of light-therapy apparatus 20 can facilitate patient compliance with a given treatment regimen.

In the embodiment illustrated in FIGS. 1-4, a plurality of light sources 30A, 30B, 30C, 30D, 30E, 30F, 30G, and 30H are disposed at symmetrical locations about frame 22. In other embodiments, a plurality of light sources 30 can be disposed asymmetrically about frame 22, the position of light sources 30 on frame 22 can be adjustable, or one or more than one light source 30 can be removable, to permit light-therapy apparatus 20 to be configured to administer, in one embodiment through the patient's face, light to a specific region or regions of a patient's maxillary or mandibular alveolar bone. For example, each light source 30 can be configured to illuminate the bone surrounding a specific number of teeth, for example two or three teeth, at a specific location.

In use, light is emitted from an inner surface 32 of one or more light source 30 extra-orally towards a desired area. As used herein, the term "inner surface" refers to the surface of an element that is closest to the facial regions of a patient when light-therapy apparatus 20 is in the use position. Inner surface 32 can have rounded edges 33, as shown for example in FIGS. 7A and 7B, and can include a clear resin window covering the light emitters, to provide greater comfort for a patient when light-therapy apparatus 20 is in the use position and when the light emitter's contact the patient's face.

Any suitable light emitter can be used for the one or more light source 30. In some embodiments, light is emitted by arrays of discrete LEDs. The LEDs can be arranged in any of a wide variety of patterns. For example, the LEDs can be arranged in staggered parallel rows to maximize the density of LEDs in the LED array. The LEDs can be arranged to achieve substantially uniform optical intensity over the light-emitting inner surface 32 of one or more light source 30. Alternatively, the LEDs can be clustered or distributed to provide varying optical intensities over an area of a light source. In some embodiments, each array can comprise 5 to about 20 LEDs or other light emitters. In some embodiments, each array can comprise about 20 to about 50 or more LEDs or other light emitters. In other embodiments, light from one or more light source 30 can be emitted by one or more than one VCSEL. A plurality of VCSELs can be disposed in an array on a light source 30. The VCSELs can be disposed in aligned or staggered parallel rows. In another embodiment, a combination of different types of light emitters, such as LEDs and VCSELs can be provided for the same light source.

A light-therapy apparatus can be configured to provide light with a desired light intensity. In one embodiment the average light intensity produced by a light source 30 is at least about 10 mW/cm². In other embodiments, the average light intensity produced by a light source is about 1 mW/cm² or greater, about 3 mW/cm² or greater, about 5 mW/cm² or greater, about 7 mW/cm² or greater, about 12 mW/cm² or greater, about 15 mW/cm² or greater, about 20 mW/cm² or greater, about 30 mW/cm² or greater, about 50 mW/cm² or greater, about 75 mW/cm² or greater, about 100 mW/cm² or greater, about 200 mW/cm² or greater, about 500 mW/cm² or greater, or about 1 W/cm² or greater. In other embodiments, the average light intensity produced by a light source can be about 20 mW/cm² or less, about 30 mW/cm² or less, about 50 mW/cm² or less, about 75 mW/cm² or less, about 100 mW/cm² or less, about 200 mW/cm² or less, about 500 mW/cm² or less, about 1 W/cm² or less, or about 2 W/cm² or less. In some embodiments, a light source 30 has an average intensity that is, or can be adjusted to be, in the range of about 10 mW/cm² to about 60 mW/cm², or about 20 mW/cm² to about 60 mW/cm². In some embodiments, the output of light source 30 is pulsed. In such embodiments, the peak light intensity can be significantly higher than about 50 mW/cm². In other embodiments, the output of light is continuous. In some embodiments, the light intensity can vary over time in a cyclical or non-cyclical fashion. The light intensity can vary with or without pulsing. In some embodiments, the light intensity can vary with pulse width modulation. Any other light intensity described anywhere above can be provided by the light-therapy apparatus.

The light emitters can be controllable so that the number of lights that are on or off at a given period can be individually controllable. For example, each light emitter can be on or off relative to other light emitters. This can be desirable when it is desirable to administer light to different regions. Thus, the light-therapy apparatus can alter the position of light being administered. In another embodiment, each light emitter can be on or off relative to other light emitters. For example, at some times, light emitters emitting in a first wavelength range can be on while light emitters emitting in a second wavelength range can be off, vice versa, or both types of light emitters can be on or off. Thus, the wavelength of light being administered can be varied. In some embodiments, the intensity of light being administered can be varied (e.g., by turning some light emitters on or off, or varying the intensity emitted by the light emitters). If the light emitters are pulsed, their duty cycle can be adjustable; e.g., light emitters can be capable of having a duty cycle of about 10%, about 20%, about 30%, about 40%, about 50%, about 60%, about 70%, about 80%, or about 90%. The light emitters can be capable of pulsing can occur with any frequency. For example, light emitters can be pulsed on the order of every picosecond, nanosecond, microsecond, millisecond, second, multiple seconds, or minutes. Light emitters can provide light with frequencies of about 1 mHz, about 10 mHz, about 50 mHz, about 100 mHz, about 500 mHz, about 1 Hz, about 2 Hz, about 5 Hz, about 10 Hz, about 15 Hz, about 20 Hz, about 25 Hz, about 30 Hz, about 35 Hz, about 40 Hz, about 50 Hz, about 70 Hz, about 100 Hz, about 200 Hz, about 500 Hz, or about 1 kHz. The light-therapy apparatus can be controllable so that any of the aforementioned characteristics of light emission (e.g., whether the light is on or off, continuous or pulsed, duty cycle, frequency, intensity, wavelength) can be varied or maintained in accordance with instructions from a controller.

The light-therapy apparatus can be capable of emitting light with varying intensities. Any ratio of intensities can be provided for light emitted at any of the wavelengths. For example, light emitted at a first wavelength can have about a 1.1×, 1.2×, 1.3×, 1.5×, 1.7×, 2.0×, 2.5×, 3.0×, 3.5×, 4.0×, 5.0×, 10×, 12×, 15×, 20×, 30×, 50×, 100× intensity compared to a light emitted at a second wavelength. In some embodiments, the same number of light emitters having a first set of characteristics and a second set of characteristics can be provided. In other embodiments, more light emitters having a first set of characteristics can be provided than light emitters having a second set of characteristics. For example, about 1.1×, 1.2×, 1.3×, 1.5×, 1.7×, 2.0×, 2.5×, 3.0×, 3.5×, 4.0×, 5.0×, 10×, 12×, 15×, 20×, 30×, 50×, 100× light emitters having the first set of characteristics can be provided as light emitters having the second set of characteristics.

One or more light source 30 can include optical elements such as one or more lenses or reflectors to focus and direct light from the light source 30 onto a selected area. Any type of optical lens or reflector can be used. For example, an optical lens can be used to collimate the light, diffuse the light, or focus the light. In some embodiments, one or more Fresnel lenses or telecentric lenses can be used. Any type of reflector can be used. A lens can be provided to cause light divergence, or light convergence. For example, one or more mirrors can be incorporated. The mirrors can be used to assist with scattering, redirecting, or focusing the light. Such optical elements can be suitably encapsulated in plastic or similar material, which can be transparent, translucent or opaque. The plastic or other encapsulating material can form an exterior surface of a light source. The light emitters or optical elements can be provided within an interior portion of the light source. Alternatively, encapsulating materials need not provided, and the optical elements or the light emitters can be provided as an exterior surface of a light source. In some embodiments, there can be a gap between a light emitter and an encapsulating material. A gap can exist between a light emitter and an exterior surface of the light source.

An exterior surface of a light source can contact a patient's face. For example, an encapsulating material for a light source can contact a patient's face. In other examples, optics, such as a lens optionally contacts the patient's face. In some embodiments, a light emitter can contact the face directly, while in other embodiments, the light emitter does not contact the face directly.

Figure 5:
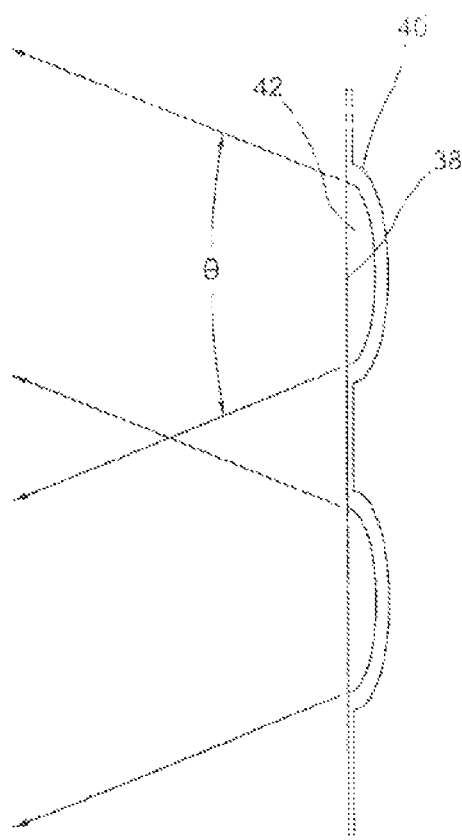
FIG. 5 is a schematic cross-sectional view through a portion of a light source having a light emitter and a reflector.

FIG. 5 shows a portion of a light source 30. In the illustrated embodiment, a light emitter 38 (which can, for example, comprise a junction in a light-emitting diode or other light-emitting semiconductor device) is located adjacent to a reflective backing 40. A curved light-reflecting recess 42 is provided adjacent to light emitter 38. Light from light emitter 38 is reflected in recess 42 to form a beam. The beams from all light emitters of a light source 30 can combine to illuminate the selected tissues. The area covered by the beam will depend upon the tissues which it is desired to treat. In some embodiments, the beam of light emitted by a light source 30 diverges to cover an area of tissue larger than the area of the light-emitting part of a light source 30. In other embodiments the emitted light converges to provide increased light intensity at the location of the tissues that it is desired to treat. In some embodiments, the emitted light diverges in a beam having an included angle Θ in the range of about 45° to about 60°. The emitted light can form a diverging to have an included angle Θ of 0° to about 15°, 0° to about 30°, 0° to about 45°, 0° to about 60°, 0°. to about 75°, 0° to about 90°, or 0° to about 120°.

Since LEDs and other light emitters can emit heat when they are operated, it can be desirable to provide a suitable mechanism for dissipating the heat to prevent any parts of light-therapy apparatus 20 that are proximate to a patient's skin from getting too hot. In some embodiments, heat is dissipated by passive cooling, such as, for example, provision of appropriate heat sinks or permitting air to flow freely around light sources 30. Heat sinks 36 are an example of passive cooling. Heat sinks can be in thermal communication with one or more light source. In one embodiment, one or more light source can comprise thermally-conductive LED wafers mounted on a suitable heat sink Heat from the LED wafers can be conducted into the heat sink and dissipated.

In some embodiments, one or more light source 30 can include a forced air, liquid, or solid state cooling system. In one embodiment, a heat sink has pins projecting from its face that is away from LED arrays. A fan causes air to flow past pins to carry away excess heat. Other fluids, such as other gases, or water or other liquids, can be driven past the pins to assist with carrying away excess heat.

A cooling system allows for administration of light without the danger of potential burns to the patient and allows for greater efficiency and control of the apparatus. A cooling system can be installed on light-therapy apparatus 20 in any suitable manner. The cooling system can be in thermal contact with one or more light source. In some embodiments, a cable recess (illustrated as 64A or 64B in FIGS. 7A and 7B) can be provided within one or more light source 30 to accommodate aspects of a cooling system or cables that can be used with or form part of light-therapy apparatus 20.

In one embodiment, as shown in FIGS. 8A-8D, a cooling mechanism 83 can be provided. In one embodiment, the cooling mechanism can contact one or more light source 81, and can be formed of a conductive material. The cooling mechanism can conduct heat from the one or more light source and dissipate the heat to the surroundings. The cooling mechanism can function as a heat spreader or heat sink. The cooling mechanism can have an increased surface area by including one or more open region 83a disposed between one or more solid region 83b. A fluid is optionally forced through the cooling mechanism.

Figure 7A:
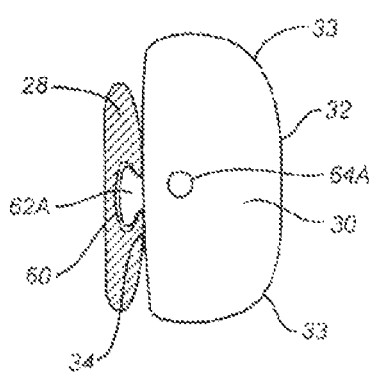
FIG. 7A is a partial cross-sectional view of a support arm of an embodiment of a light-therapy apparatus showing the engagement between a track engaging ridge on a light source and a track formed in the support arm.

In one embodiment that can use either passive or active cooling, or both, support arms 28 can be constructed from milled aluminum, and one or more light source 30 can be constructed so as to be engageable with a track formed on the inner surface 34 of support arms 28, as shown for example in FIG. 7A. One or more light source 30 can be engageable with a track 60 formed in the inner surface 34 of support arms 28 via a track-engaging ridge 62A formed on the one or more light source 30. Track 60 and track-engaging ridge 62A can have any suitable complementary configuration and orientation to retain one or more light source 30 against support arms 28 and oriented toward a wearer's face when light-therapy apparatus 20 is in the use position. One or more light source 30 can be slideable within track 60, to facilitate the positioning of light source 30. One or more light source 30 can alternatively be coupled to support arms 28 in any other suitable manner, such as by a clip, clamp, adhesive, thermally conductive adhesive, hook and loop fastener, or any other connection mechanism. In some embodiments, one or more light source 30 can be integrally formed with support arms 28.

In some embodiments, the track can have a fixed position relative to the rest of the frame. In one embodiment, a track can be a shaped feature within the frame. In other embodiments, the track can be adjustable to the rest of the frame. For example, the track can be formed of a material that can allow a user to bend the track to a desired configuration, and can stay at that configuration. In other embodiments, adjustment features, such as hinges, joints, or other moving parts can allow a user to adjust a track position.

One or more light source can slide along a length of the track. Alternatively, light sources can be attached or removed at different points along the track. In some embodiments, light sources can be attached or removed only at certain locations along the track (e.g., discrete portions that accept the light sources). Alternatively, one or more light source can be attached or removed at any point along the track. Thus, one or more light source can be displaced.

In some embodiments, one or more light sources can be applied to the frame so that they have a fixed orientation. Alternatively, the one or more light sources can be rotatable relative to the frame. Depending on the dimensions of a light source, this can allow variation in the region receiving light. One or more light source can be rotatable about one or more axis. For example, one or more light source can be rotatable about a first axis that is about parallel, i.e., ranging from +18° to −18°. of being parallel, with the support arm, about a second axis that is perpendicular to the support arm, or about a third axis that is perpendicular to both the first and second axis. In some embodiments, one or more light source can be supported by a hinge, pivot, or other configuration that can allow one axis of rotation. In other embodiments, multiple hints, pivots, or other mechanisms can be provided that can allow for two or more axes of rotation. In another embodiment, one or more light source can be supported by a ball and socket joint that can provide multiple degrees of freedom. The orientation of one or more light source relative to the frame can be manually adjusted. A user can turn one or more light source to a desired orientation. Alternatively, the orientation of one or more light source can be remotely controlled. For example, one or more actuator can be provided that can cause one or more light source to turn to a desired orientation. Actuators can operate based on a signal received from a controller. The signal can be received via a wired connection or wirelessly, as described elsewhere herein.

In another embodiment, as shown in FIGS. 8A-8D, one or more light source 81 can be configured to slide along a support arm 88. For example, a support arm on the right side of the face and a support arm on the left side of the face can include a track 85 that can enable a light assembly to slide along the track. The track can be parallel to the support arm. Alternatively, the track can be provided at some non-parallel angle to the support arm. In some embodiments, the track or support arm can have a substantially horizontal orientation when the apparatus is in use. A light assembly can include one or more light source 81, temperature control system 83 or vertical track 87. In some embodiments, one or more light assembly can be provided on a right support arm or one or more light assembly can be provided on a left support arm. In some embodiments, a support arm does not include a light assembly. A track on a support arm can be about horizontal, i.e., ranging from +18° to −18° of being horizontal. In alternate embodiments, the track can have any other orientation, which can include a vertical track, slanted travel, or curved track. In some embodiments, one, two, three, or more tracks can be provided on a support arm. The position of a light assembly relative to a support arm can be manually adjusted. For example, a user can push the light assembly to a desired position along the support arm. Alternatively, the position of the light assembly can be remotely controlled. For example, one or more actuator can be provided that can cause the light assembly to move to a desired position. Actuators can include, but are not limited to, motors, solenoids, linear actuators, pneumatic actuators, hydraulic actuators, electric actuators, piezoelectric actuators, or magnets. Actuators can cause the light assembly to move based on a signal received from a controller.

In some embodiments a vertical track 87 can be provided. The vertical track can be about perpendicular, i.e., ranging from +9° to −9° of being perpendicular, to a track along a support arm 88. Any description herein of the vehicle track can be applied to any other secondary track of any orientation that can be in communication with a track on a support arm. The vertical track can be adjustable relative to a track on the support arm. For example, the vertical track can slide along the track along the support arm. In some embodiments, the vertical track can be removable or attachable to the support arm, such as on the track along the support arm. In some instances, the vertical track can be attachable at one or more location along the support arm. Such locations can be discrete or continuous. One, two, three, four, or more vertical tracks can be attachable to the support arm simultaneously. The position of a vertical track relative to a support arm can be manually adjusted. For example, a user can push the vertical track to a desired position along the support arm. Alternatively, the position of the light assembly can be remotely controlled. For example, one or more actuator can be provided that can cause the light assembly to move to a desired position. The actuator can respond to a signal from a controller. The vertical track is optionally rotatable relative to the support arm. For example, the vertical track can be rotatable so that it is no longer vertically oriented, but can be horizontally oriented, or provided at a slant. The vertical track can be rotated manually. Alternatively, one or more actuator can be provided that can cause the vertical track to rotate to a desired position. The actuator can respond to one or more signal from a controller.

One or more light source 81 can be configured to slide along a vertical track. Alternatively, one or more light source can be attachable or removable from the vertical track at discrete or continuous locations. The position of one or more light source relative to a vertical track can be manually adjusted. For example, a user can push one or more light source to a desired position along the vertical track. Alternatively, the position of one or more light source can be remotely controlled. For example, one or more actuator can be provided that can cause one or more light source to move to a desired position. One or more light source can have a fixed orientation relative to the vertical track. Alternatively, it can be rotatable about a first axis, second axis, or third axis, such as those previously described. One or more light source can be manually oriented, or can have an actuator that orients the light source in response to a signal received from a controller. In one embodiment, one or more light source can be attached to a vertical bar 89 that can allow the light source to rotate about the bar within a limited range. This can allow the light source to have a desired position relative to a patient's face when in use. In one embodiment, two light sources can be provided along a vertical track. In alternate embodiments of the invention, the vertical track need not be perpendicular to a support arm and vertical. For example, a secondary track can be provided at any angle relative to the support arm (e.g., at about 15 degrees, about 30 degrees, about 45 degrees, about 60 degrees, about 75 degrees, or about 90 degrees relative to the support arm). In some embodiments, the secondary track can have a fixed orientation relative to the support arm. Alternatively, the secondary track can be rotatable relative to the support arm.

In some embodiments, one or more light source can rotate or move relative to the secondary track. For example, a hinge, pivot, ball and socket joint, or other type of mechanism can be provided that can allow one or more light source to rotate relative to the second track. In some embodiments, one or more light source can rotate within a limited range. In some embodiments, the relative position of one or more light source can be adjusted manually. For example, one or more light source can contact a patient's face and the position of the light source can conform to the contours of the patient's face. For example, the relative angle of the light source can conform to the patient's face. In other embodiments, one or more actuator can be provided to adjust the position of one or more light source. An actuator can operate in response to a signal received from a controller. In some embodiments, the position of one or more light source can be locked so that once a desired configuration for the light source has been set, it cannot be adjusted manually. Alternatively, one or more light source can be responsive to force, so that a patient or other individual can be able to adjust the position of the light source.

In some embodiments, a third track, or fourth track can be provided. In one embodiment, a third track can be provided on a secondary track, or a fourth track can be provided on a third track. The support arm can comprise any number of tracks that provide various degrees of flexibility in the locations of one or more light source. In other embodiments, the support arm comprises one or more other components or configurations which can include but are not limited to bars, notches, slides, elastics, or holes.

Figure 7B:
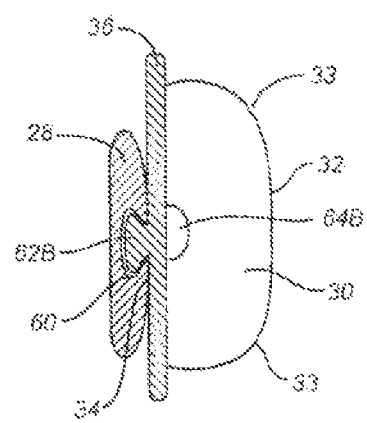
FIG. 7B is a partial cross-sectional view of a support arm of an embodiment of a light-therapy apparatus showing the engagement between a track engaging ridge on a heat sink and a track formed in the support arm.
Figure 8A:
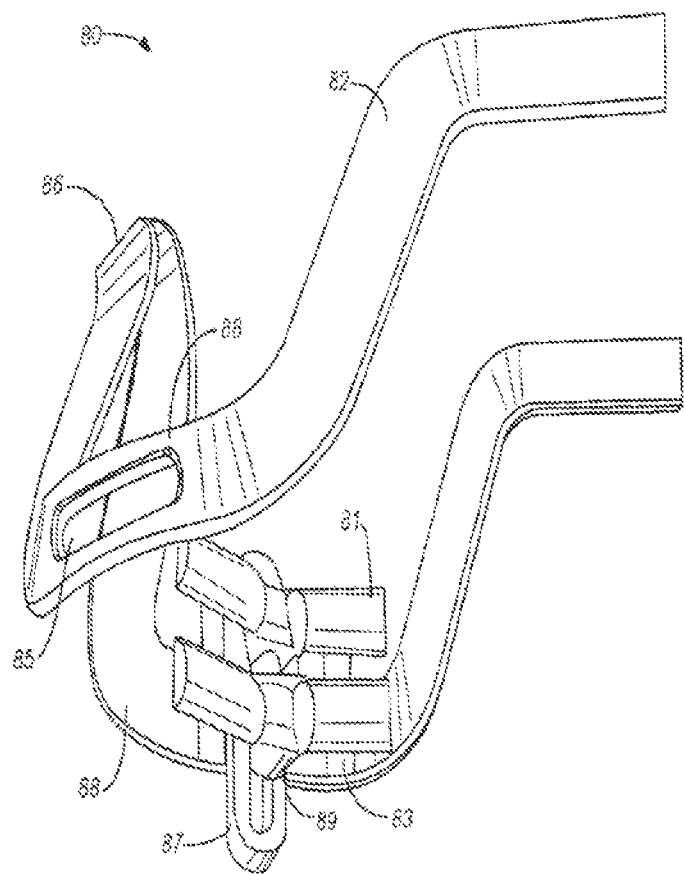
FIG. 8A shows a first view of a light-therapy apparatus in accordance with another embodiment of the invention.
Figure 8B:
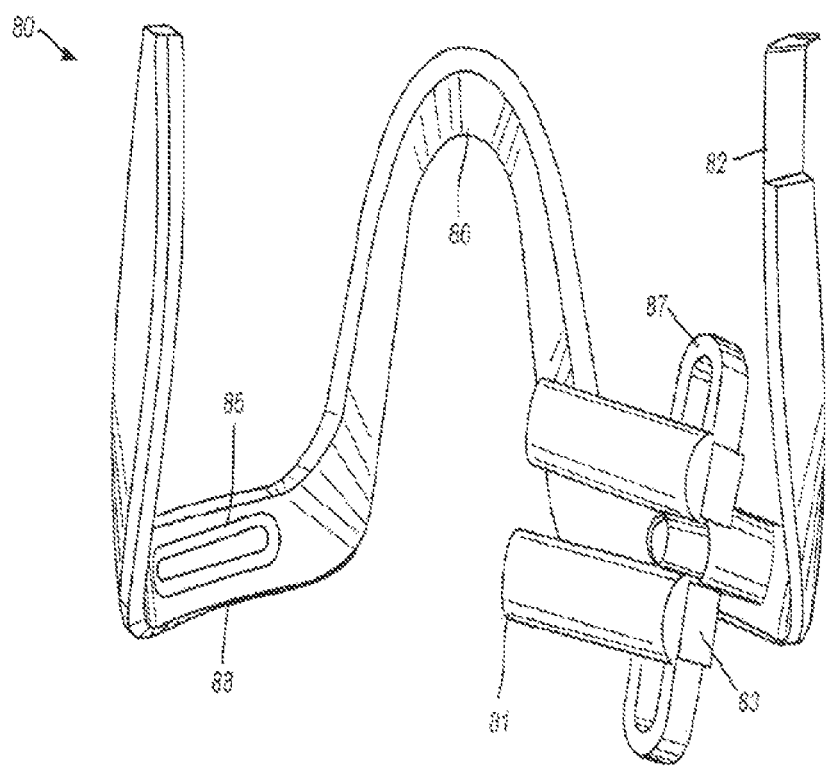
FIG. 8B shows another view of the light-therapy apparatus.
Figure 8C:
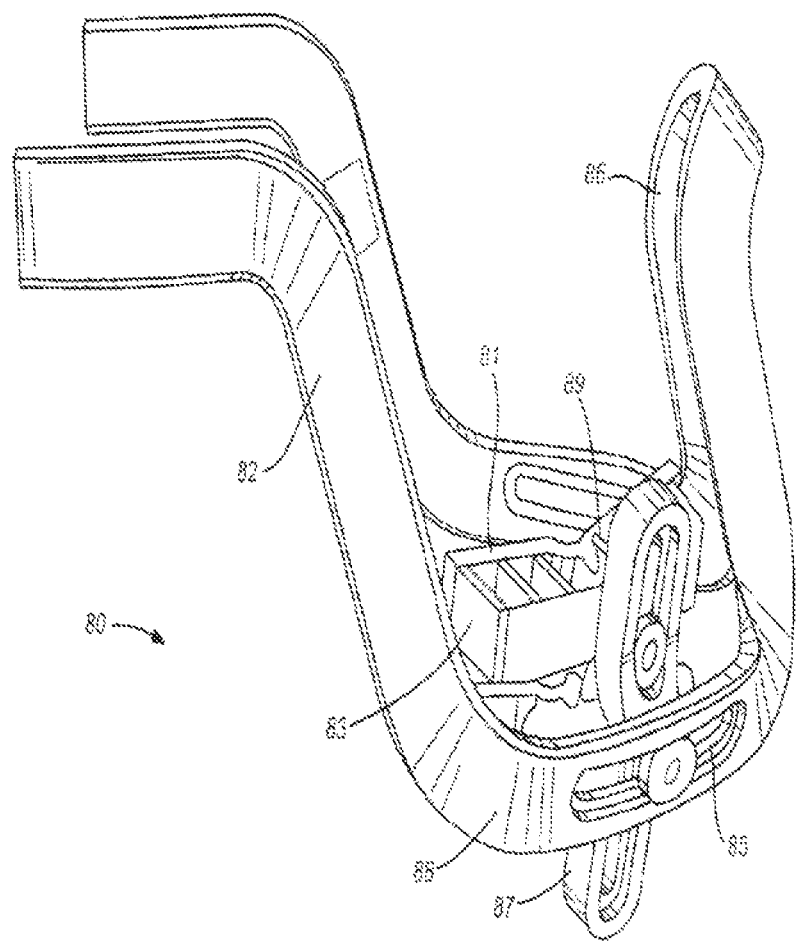
FIG. 8C shows an additional view of the light-therapy apparatus.
Figure 8D:
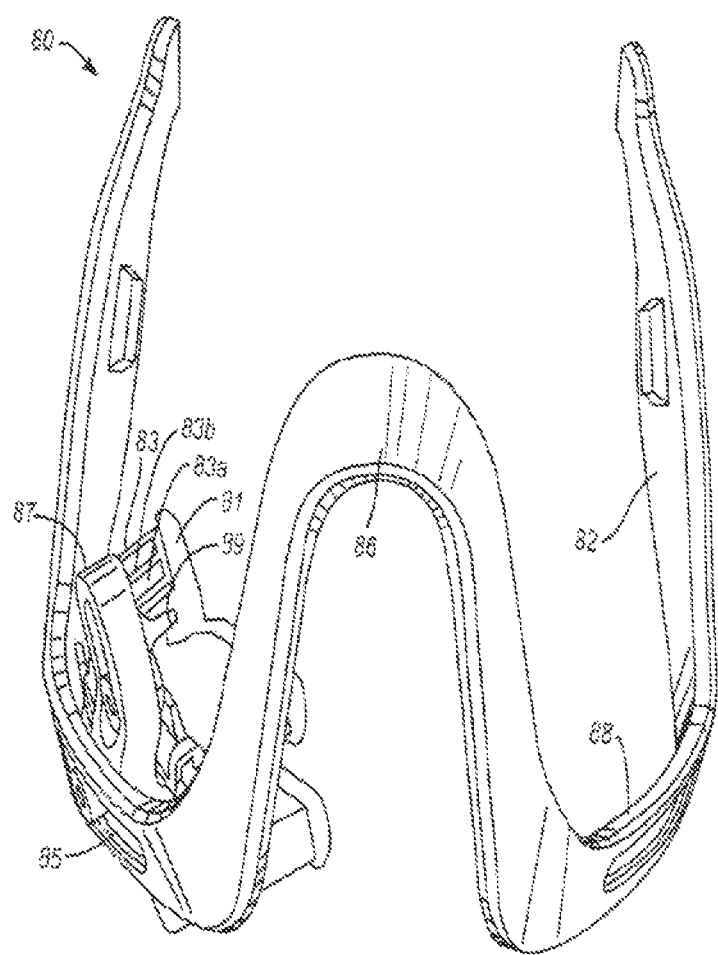
FIG. 8D provides another view of the light-therapy apparatus.

A heat sink 36 can interpose one or more light source 30 and inner surface 34 of support arms 28. Heat sink 36 can, for example, be made of copper, aluminum, or other suitable thermally conductive material, to enhance dissipation of heat from light source 30. With reference to FIG. 7B, heat sink 36 can be engageable with track 60 formed in the inner surface 34 of support arms 28 via a track-engaging ridge 62B formed on heat sink 36. Track 60 and track-engaging ridge 62B can have any suitable complementary configuration and orientation to retain heat sink 36 against support arms 28, and to retain light source 30 oriented toward a wearer's face when light-therapy apparatus 20 is in the use position. Heat sink 36 can alternatively be coupled to support arms 28 in any suitable manner, rather than via engagement with track 60 through optional track-engaging ridge 62B. For example, heat sink 36 can be coupled to light source 30 by a clip, clamp, adhesive, thermally conductive adhesive, hook and loop fastener, or any other connection mechanism. In some embodiments, heat sink 36 can be integrally formed with either or both of light source 30 or support arms 28. In some embodiments, a heat sink can be coupled to each light source.

A gas, liquid, or solid state cooling system can be provided on support arms 28 to maintain light source 30 at a suitable temperature, or passive cooling means can be employed as previously described. In some embodiments, the temperature of the inner surface 32 of light source 30 can be maintained below a temperature of about 41° C., in one embodiment, from about 20° C. to about 35° C. A cable recess, illustrated for example as 64A or 64B (FIGS. 7A and 7B) can be provided in light source 30 to accommodate cables for carrying electricity to light source 30 or components of a gas or liquid cooling system. An optional sensor or a controller 50 as described below can be provided, to automatically switch off any light source if the temperature of inner surface 32 or some other designated portion of that particular light source 30 exceeds a predetermined value.

The temperature of a light source can be varied or maintained to maintain or approach a desired temperature. For example, a cooling system can be used to reduce the temperature of a light source and prevent it from becoming too hot. In some situations, a temperature control system can be provided that can prevent a light source from being too cold or too hot. A desired temperature range can be preset. The desired temperature range can be fixed or adjustable. In some embodiments, a desired temperature range can range about ±10° C., about ±7° C., about ±5° C., or about ±3° C. of the ambient air temperature, or range about ±10° C., about ±7° C., about ±5° C., or about ±3° C. of the skin temperature of the user wearing the apparatus.

In some embodiments, light-therapy apparatus 20 is disposed and supported exclusively or substantially external to a mouth of a patient. A light-therapy apparatus which is supported exclusively or substantially external to a mouth of a patient can facilitate the use of that light-therapy apparatus optionally with one or more of a wide variety of intra-oral orthodontic devices. For example, orthodontic appliances, such as those disclosed herein, can be provided as intra-oral orthodontic devices and employed in the present apparatuses or methods. In other embodiments, a portion of light-therapy apparatus 20 can be disposed within a mouth of a patient, to assist in securing or positioning light-therapy apparatus 20 on a patient's face or head. For example, bite wings or an intra-oral tray which is supported in position by having a patient hold the intra-oral tray between her or his upper and lower teeth can be coupled to light-therapy apparatus 20 to assist in retaining or supporting the apparatus. An example of a suitable intra-oral tray is described in PCT publication numbers WO2009/000075 and WO 2006/087633, both of which are incorporated by reference herein in their entirety. In some embodiments, an intra-oral device can comprise one or more light sources or be capable of intra-orally administering light to a region. In some embodiments, light can be administered to a region intra-orally or extra-orally or both. In other embodiments, light is administered to a region only extra-orally, and is not administered to a region intra-orally. In some instances, light can only be administered to a region transdermally through the skin of the patient.

Figure 9:
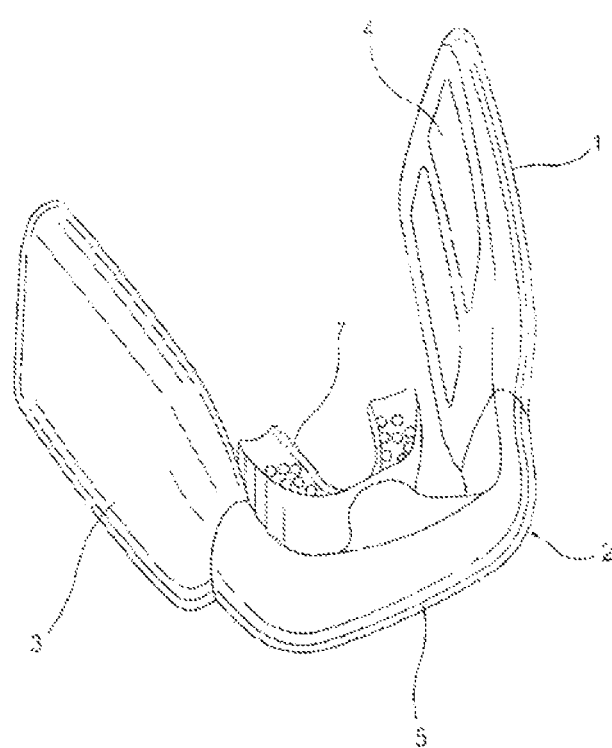
FIG. 9 is a view from the front side of an extra-oral light-therapy apparatus having an intra-oral tray, an extra-oral bridge, and left and right side extra-oral LED arrays.
Figure 9A:
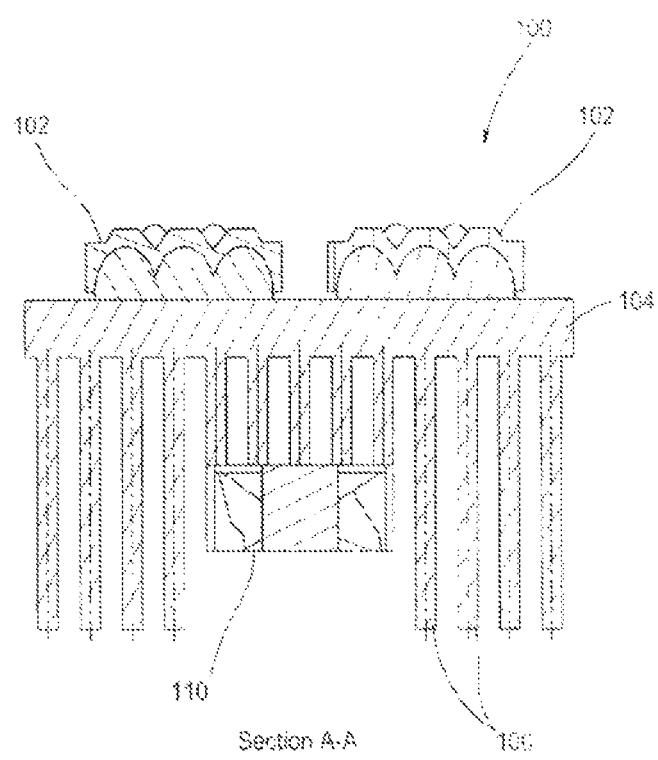
FIGS. 9A, 9B and 9C are respectively a cross-section, a front side elevation and a rear elevation of a light source having a cooling fan, a heat sink and two arrays of light emitters.
Figure 9B:
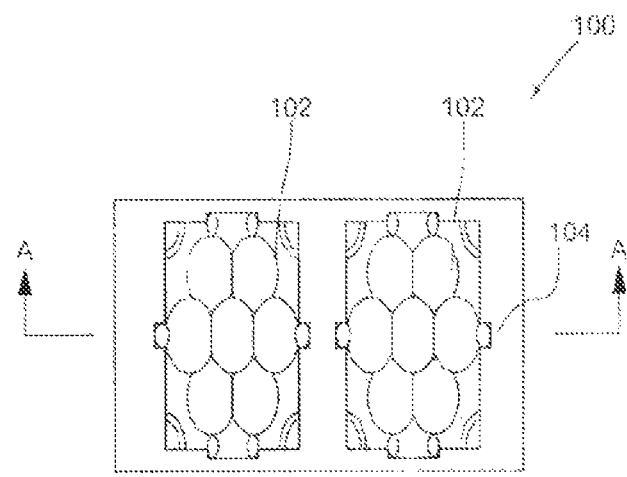
Figure 9C:
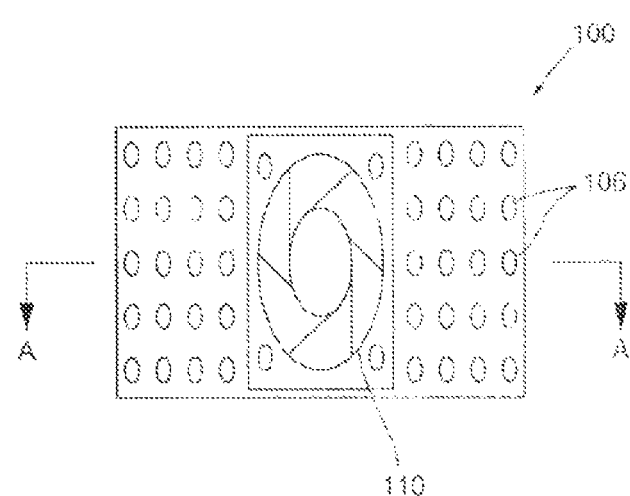
Figure 10:
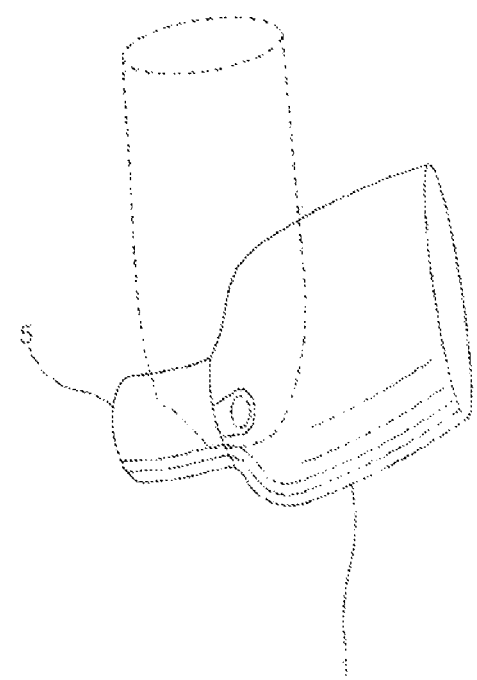
FIG. 10 is a right side view of the apparatus of FIG. 9 with the end of the extra-oral bridge attached to the extra-oral LED array.

FIG. 9 shows an illustrative light-therapy apparatus 2 that comprises an extra-oral light source 4 having a right side 1 and a left side 3 (as viewed from the front of the apparatus), an extra-oral bridge 5, and an intra-oral tray 7. Intra-oral tray 7 registers to a patient's teeth. A light source 4 is rigidly connected to intra-oral tray 7 by extra-oral bridge 5. Alternatively, some flexibility can be provided between the intra-oral tray and the extra-oral bridge. Therefore, a patient can position a light source 4 accurately and repeatably to illuminate a desired location in the patient's dental or maxillofacial areas by inserting intra-oral tray 7 into his or her mouth and biting intra-oral tray 7 so that it registers to at least some of the patient's teeth. This stabilizes light-therapy apparatus 2 and positions a light source 4 at a desired position. The consistent alignment and targeting of light from the light source 4 during subsequent treatments makes the treatments more repeatable.

Figure 11:
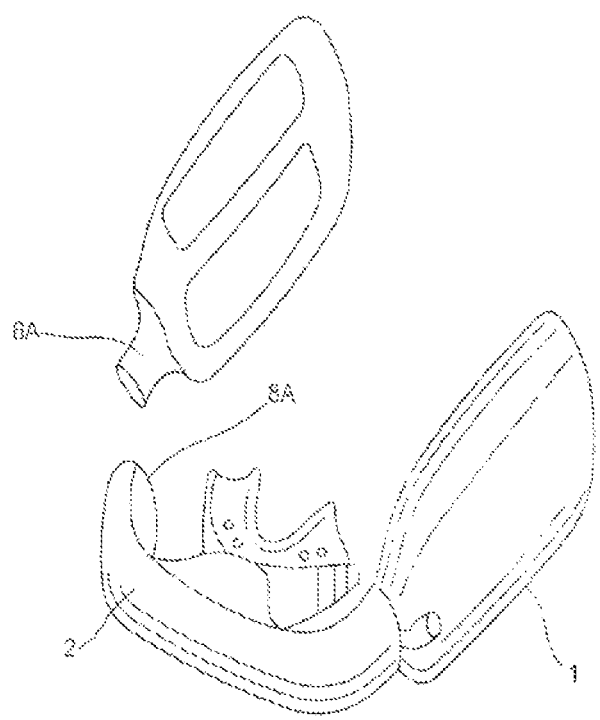
FIG. 11 is a view from the front-left side of the extra-oral bridge, intra-oral tray and extra-oral LED array of FIG. 9.

In the illustrated embodiment, extra-oral bridge 5 is removable from an extra-oral light source 4 and intra-oral tray 7. Providing a light-therapy apparatus 2 having major components that are detachably connectable to one another adds versatility. A design which permits the major components of the light-therapy apparatus to be disassembled and reassembled while preserving alignment of extra-oral light source 4 to intra-oral tray 7 has the advantage that the apparatus can be disassembled for storage or transportation and then used immediately after assembly. FIG. 11 shows light-therapy apparatus 2 with extra-oral light source left side 3 detached from extra-oral bridge 5.

Extra-oral bridge 5, extra-oral light source right side 1, and extra-oral light source left side 3 can be secured together via a suitable connector. For example, extra-oral bridge 5, the extra-oral light source right side 1, and the extra-oral light source left side 3 can be connected by inserting male connector portions 6A of the extra-oral light source right and left sides 1 and 3 into corresponding female connector portions 8A of extra-oral bridge 5 (see FIG. 11). Suitably, the suitable connector allows extra-oral light source right and left sides 1 and 3 to be detached from extra-oral bridge 5 for ease of use and flexibility.

In some embodiments, extra-oral light source right and left sides 1 and 3 are rotatable between a sagittal orientation (as shown in FIG. 9) and a vertical orientation (indicated in dotted outline in FIG. 9). Light source right and left sides 1 and 3 can be locked at a desired angle of rotation by any suitable mechanism. This permits light source right and left sides 1 and 3 to be arranged so that the light that they emit fully covers the desired treatment areas.

Figure 13:
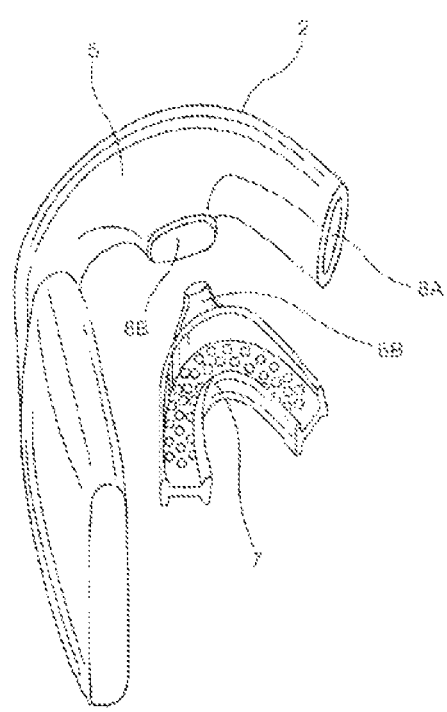
FIG. 13 is a view from the left rear side of the extra-oral bridge, intra-oral tray and extra-oral LED array of FIG. 9 with the intra-oral tray detached.

Intra-oral tray 7 can be connected to extra-oral bridge 5 by way of another suitable connector. In the embodiment illustrated in FIG. 13, a male portion 6B of intra-oral tray 7 is removably received in a female portion 8B of extra-oral bridge 5. Where intra-oral tray 7 is removable from extra-oral bridge 5, extra-oral bridge 5 can be reused for other patients (after suitable sterilization). Intra-oral tray 7 can be disposed of after it is no longer required by a patient. In some embodiments, extra-oral bridge 5 is non-removably attached to intra-oral tray 7.

Intra-oral tray 7 can be inserted into a patient's mouth and can be suitably shaped to fit around a patient's teeth. Intra-oral tray 7 can register with a few selected teeth (for example, intra-oral tray 7 can comprise a bite tab) or can fit around the patient's full set of teeth. In one embodiment, the intra-oral tray 7 comprises a frame of a plastic or other suitable material that can serve as a skeleton for a settable material. The intra-oral tray frame can be perforated to aid retention of the settable material. The intra-oral tray frame can comprise extra-oral bridge 5 or a connector to connect to extra-oral bridge 5. The intra-oral tray can be optionally provided, and other securing means for an extra-oral bridge can be provided. For example, frames, as described elsewhere herein, can support an extra-oral bridge or extra-oral light source relative to the patient's face.

Prior to being used in the administration of light, a frame for intra-oral tray 7 can be filled with a suitable settable material (for example a clear vinyl siloxane gel or similar material) which sets around the patient's teeth and subsequently allows repeatable alignment of intra-oral tray 7 in the patient's mouth. Where intra-oral tray 7 could be in the path of light as it travels from light source 4 to selected tissues, the material of intra-oral tray 7 should be transparent to the light.

Extra-oral bridge 5 can conform around the jaw line of a patient. The light source right and left sides 1 and 3 can be respectively positioned on the right and left sides of a patient's face along the patient's jaw line. Extra-oral bridge 5 can be adjustable to permit alignment of light source left and right sides 1 and 3 with selected areas to be irradiated. Light source left and right sides 1 and 3 are extra-oral (outside of the patient's oral cavity). Light can pass from left and right sides 1 and 3 through tissues of the patient's lips and cheeks into selected areas on the patient's gums or in the patient's jaws. Light can be administered transcutaneously through the patient's face to any region as disclosed herein.

Figure 12:
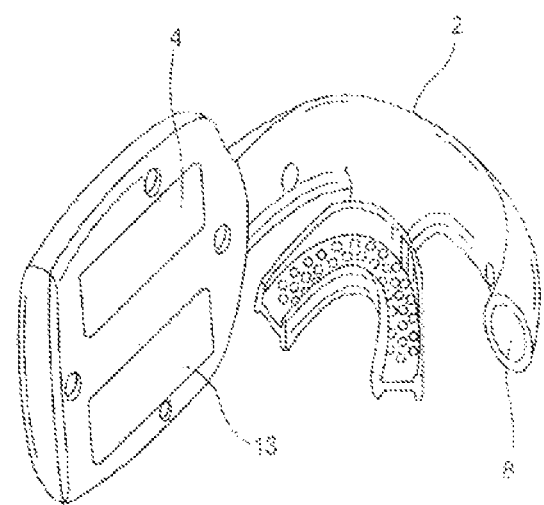
FIG. 12 is a view from the rear right side of the extra-oral bridge, intra-oral tray and extra-oral LED array of FIG. 9.

In some embodiments, one or more light source 4 emits light toward the patient. Any light source, with any configuration of light emitters as described anywhere else herein can be used. In some embodiments, a light source 4 has an inner surface 13 (see FIG. 12) that is placed near or against the patient's skin adjacent to the tissues that it is desired to treat. In some embodiments, one or more light source can contact the patient's face. The one or more light source can contact the portion of the face overlying a desired region. Light is emitted is from inner surface 13 toward the area of treatment. In some embodiments, left and right sides 1 and 3 of light source 4 each have a length similar to a significant fraction of the length of a human jaw. For example, left and right sides 1 and 3 can each have a length of about 20 mm to about 90 mm in some embodiments and about 25 to about 45 mm or about 60 mm in some embodiments. A light source can have any other dimensions, including those disclosed herein. In cases where a light source 4 is intended to treat or prevent a localized condition, then light source 4 can be smaller in extent. In some embodiments, light source 4 has optics that emit light in the form of diverging beams. The light source is usable with optics as described anywhere above. In such cases, light source 4 can be somewhat smaller than the area of tissues to be treated because light from light source 4 can diverge as it passes through the tissues of the patient's lips and cheeks before reaching the tissues of the jaw and or gums.

Light source 4 can be wide enough to irradiate both upper and lower jaws of a patient simultaneously although in some embodiments light source 4 can be narrower. For example, light source 4 has a width in the range of about 12 mm to about 40 mm in some embodiments (e.g. about 15 to about 17 mm in some embodiments). In some embodiments, a light source irradiates only an upper jaw or a lower jaw, or portions thereof.

While the invention is described herein as usefully employing LEDs, other light emitters such as lasers could suitably be employed. The character of the light emitted by light source right and left sides 1 and 3 will depend upon the nature of the LEDs or other light emitters in light source 4. It is generally desirable that the emitted light include light in the wavelength range of 620 nm to 1000 nm. In some embodiments the emitted light includes light having a wavelength in at least one of the following wavelength ranges: about 820 to about 890 nm or about 620 to about 680 nm. In some embodiments, light having a wavelength in the ranges of about 820 to about 890 nm and about 620 to about 680 nm can be provided. Light having wavelengths corresponding to or falling within one or more of the following ranges can be particularly effective: about 613 nm to about 624 nm, about 667 nm to about 684 nm, about 750 nm to about 773 nm, about 812 nm to about 846 nm, or any other wavelengths described elsewhere herein. The range about 613 nm to about 624 nm corresponds to a band at which reduced cytochrome c oxidase absorbs light. The range about 812 nm to about 846 nm corresponds to a band at which oxidized cytochrome c oxidase absorbs light. Light sources can be configured to provide light of any other wavelength as described anywhere above.

Figure 14:
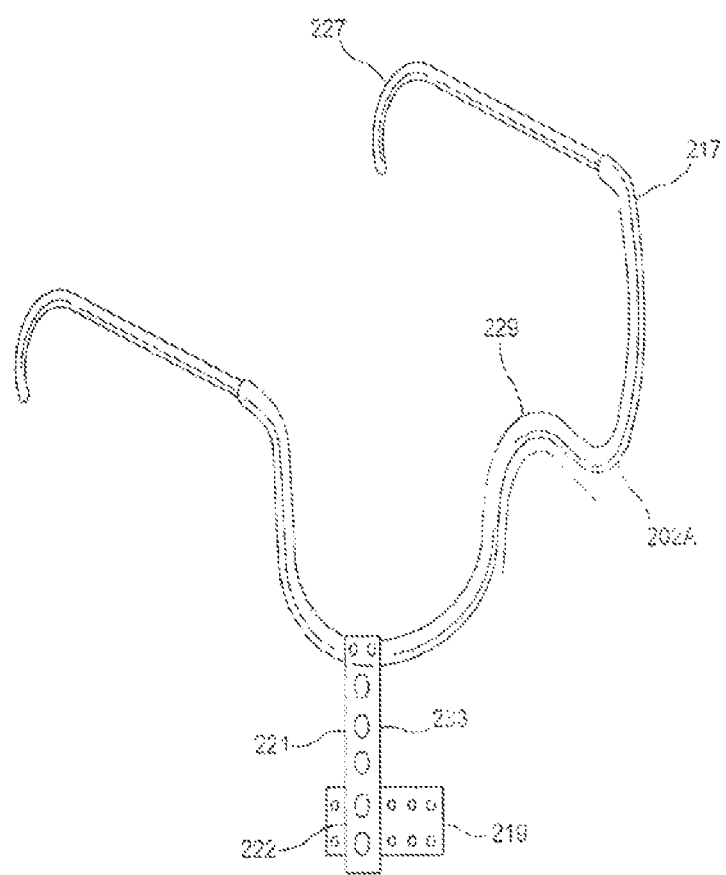
FIG. 14 is a perspective view of a light-therapy apparatus according to an alternative embodiment in which an LED array is supported by a head-set.
Figure 15:
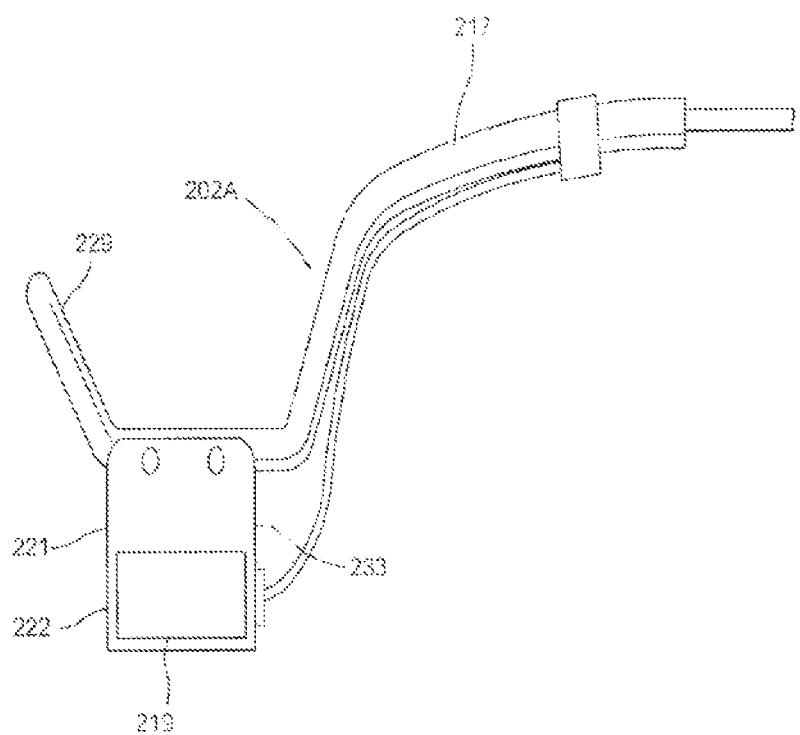
FIG. 15 is a side view of the light-therapy apparatus of FIG. 14.

FIGS. 14 and 15 show a light-therapy apparatus 202A having a head-set style arrangement. Light-therapy apparatus 202A comprises a head-set 217 and at least one extra-oral light source 219 mounted to head-set 217 by way of a suitable connector 221. Head-set 217 can have the general form of a frame for eyeglasses. In the illustrated embodiment, headset 217 has arms 227 that fit above and around the patient's ears and a frame 229 that fits over the bridge of the patient's nose. Head-set 217 can also include lenses (not shown). Suitably, the lenses can be made of a material that blocks radiation at wavelengths emitted by light source 219 so that the patient's eyes are protected from the radiation. Light source 219 can comprise an array of LEDs or other light emitters.

When head-set 217 has been adjusted to fit an individual patient, frame 229 registers with the bridge of the patient's nose and arms 227 sit on the patient's ears. Head-set 217 is configured to sit on the patient's head in the same way each time it is put on. Head set 217 can be adjusted for fit by adjusting arms 227 which can be made of a firm, resilient material that allows for some flexibility for a better and more secure fit for individual users. In some embodiments, arms 227 can also be adjusted horizontally along their axis. Frame 229 can also be adjustable, for example, by bending to allow for a better and more secure fit. An elastic keeper such as an elastic strap can be provided to hold head-set 217 in place during use.

Figure 16:
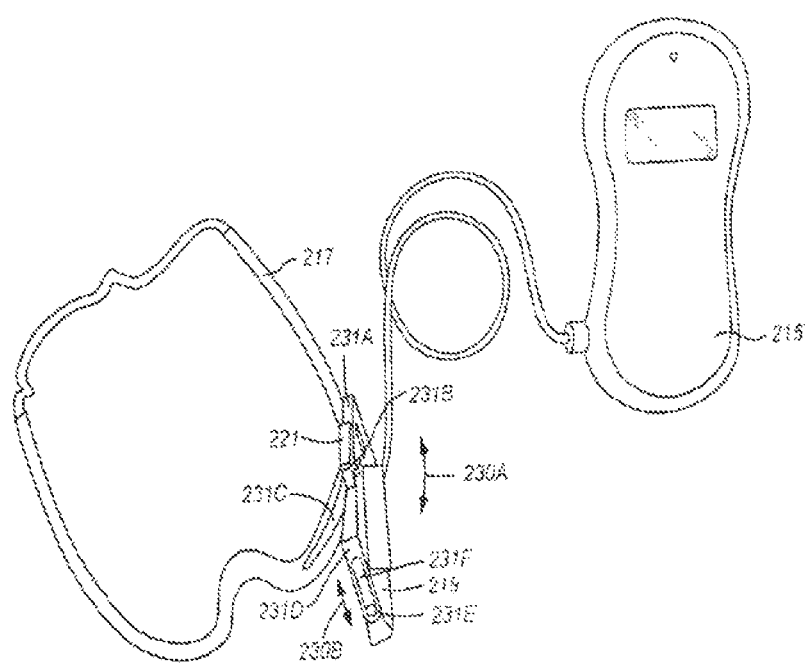
FIG. 16 is a perspective view of a light-therapy apparatus according to another alternative embodiment in which an LED array is supported by a head-set.

In the embodiment shown in FIG. 16, connector 221 permits the position of light source 219 to be adjusted both along a horizontal axis 230A and a vertical axis 230B relative to head-set 217. A yoke 231A is mounted to head-set 217 by screws 231B which pass through slot 231C. The position of light source 219 in horizontal direction 230A can be adjusted by loosening screws 231B, sliding yoke 231A to a desired position along slot 231C and retightening screws 231B. Light source 219 is connected to arms 231D of yoke 231A by screws 231E which pass through slots 231F. The vertical position of light source 219 can be adjusted by loosening screws 231E, sliding light source 219 up or down along slots 231F to a desired vertical position and then retightening screws 231E. Any other mechanism, including those described elsewhere herein, can be used to allow the light source position to be altered vertically or horizontally.

In the illustrated embodiment slot 231C is curved when viewed from above. Slot 231C generally follows the curvature of a typical maxillary bone such that light source 219 can effectively be applied against the patient's skin for a range of positions of light source 219 along slot 231C. Since the lower portions of people's faces are typically narrower than upper portions, connector 221 can hold light source 219 so that it is tilted with its lower edge projecting more in the direction of the patient than its upper edge. In some embodiments the angle of tile of light source 219 is adjustable. Head-set 217 can be adjusted so that light source 19 is biased against the patient's face when head set 217 is being worn by a patient. When the apparatus is in use, the light source can be contacting the patient's face. The light source can contact the region of the face overlying the region, thereby administering light transdermally to the region.

Many alternative designs for connector 221 can be provided. For example, connector 221 can comprise a bar, rod or similar device that can be clamped or otherwise fastened to head-set 217 and a clip or similar mechanism that fastens light source 219 to the bar, rod or similar device.

Figure 17:
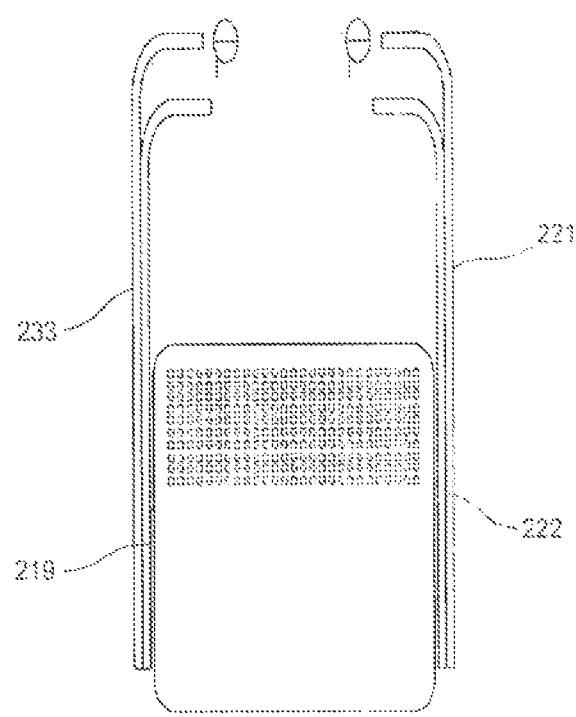
FIG. 17 is a front view of at least one LED array, and a connector detached from the head-set.

As shown in FIG. 17, in some embodiments light source 219 can be removably detached from headset 217. This can be convenient for storage or transportation of light-therapy apparatus 202A. When the apparatus is in use, the light source can contact a patient's face.

In another embodiment, head-set 217 comprises an adjustable strap (not shown) which fits around the crown of a patient's head for securing the extra-oral light-therapy apparatus 202A. The adjustable strap can also fit around a patient's chin and extend back to the crown and around the crown of a patient's head. The adjustable strap can be made of a flexible, elastic woven material.

Figure 18:
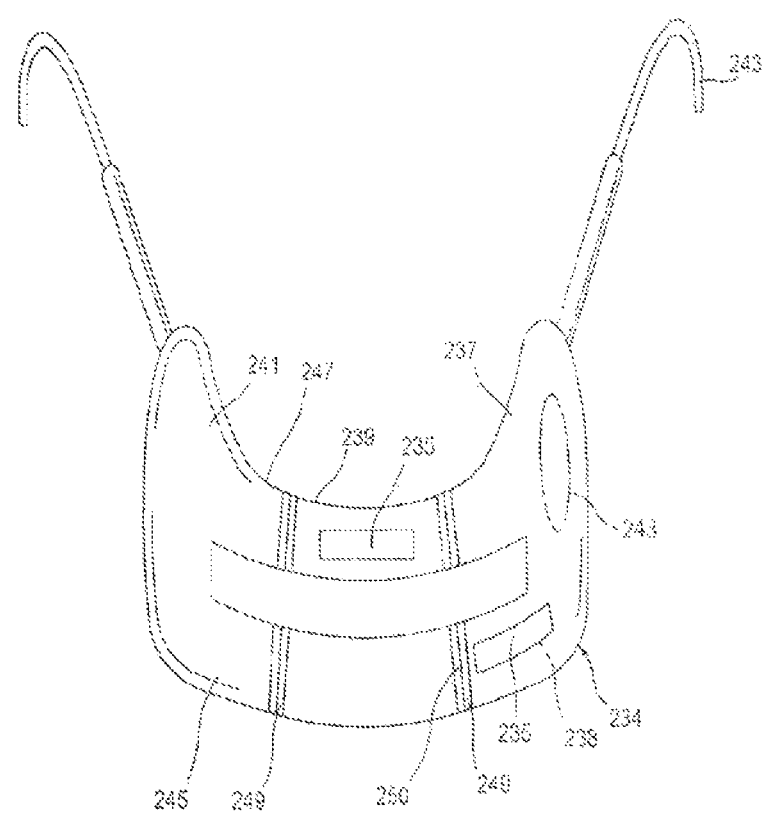
FIG. 18 is a front view of an external light-therapy apparatus having two LED arrays, a hinge-like member, and an attaching means.
Figure 19:
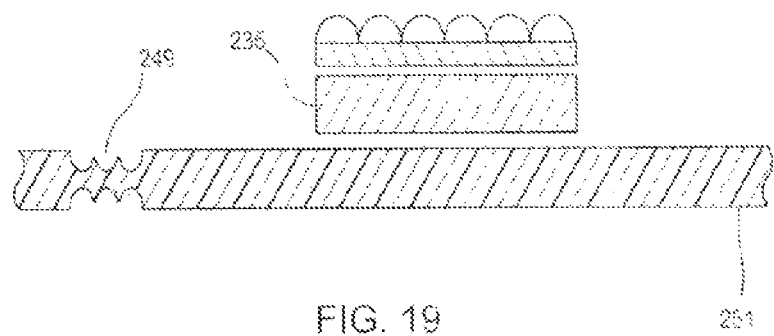
FIG. 19 is a cross-sectional view of an LED array mounted onto a substrate.

FIG. 18 shows a light-therapy apparatus 234 comprising at least one light source 235. Light source 235 comprises at least one light emitter, for example an LED array, mounted on a thin molded substrate 251 (FIG. 19). More than one array of light emitters can be provided in light source 235. For example, the light source 235 shown in FIG. 18 has two arrays of LEDs. Arrays 36 of light emitters can be arranged in lower level 245 and an upper level 247. The upper and lower levels can be separately controlled. The upper and lower levels respectively irradiate tissues of the upper and lower jaws. An attaching means 243 is provided for securing the apparatus to the area of treatment.

A power source and controller, which can comprise a programmable controller 215 as described above, operate light source 235 to emit light according to a desired protocol.

In the illustrative apparatus 234 shown in FIG. 18, light source 235 has a right section 237, a center section 239 and a left section 241. Right section 237 and the left section 241 are respectively supported on the right and left sides of a patient's face. One or more light sources can contact a patient's face when the apparatus is worn by the patient. A light source 235 as shown in FIG. 18 can be supported by way of any suitable attaching means including: a head-set 217 as described above; an intra-oral tray 7 which can comprise a full tray or one or more bite tabs as described above; an adhesive such as double-sided adhesive tape; a strap or set of straps; or supporting or attachment mechanisms.

The LED arrays can be removably attached to light source 235 by suitable connectors 238 such as ribbon connectors or can be more permanently integrated into light source 235 as illustrated in FIG. 19. Providing removable, repositionable LED arrays on a light source 235 permits LED arrays to be arranged on light source 235 so as to optimally illuminate selected tissues. LED arrays can be concentrated to illuminate selected tissues while areas of light source 35 that overly non-selected tissues do not need to have any LED arrays.

Figure 20:
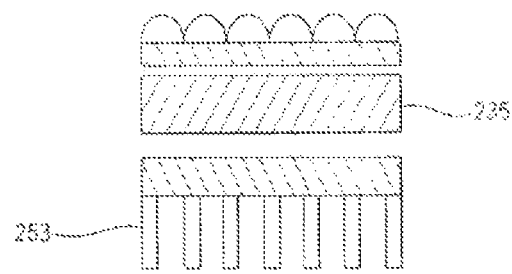
FIG. 20 is a cross-sectional view of an LED array detached from the substrate.

FIG. 20 shows a cross-section of an LED array 236 of external light-therapy apparatus 234 detached from substrate 251. A clip or similar attaching means 253 allows the at least one LED array 236 to be mounted onto substrate 251. Substrate 251 can serve as a heat sink as described above. Substrate 251 can be made of aluminum or similar metal that is a good heat conductor. Substrate 251 can be moldable (i.e., flexible in one or two dimensions so that it can be formed to follow contours of a patient's face and, once formed, retains its shape).

Hinge-like members 249 can be provided between arrays 236 to allow light source 235 to be bent to provide a better fit around the facial area. Hinge-like member 249 can comprise a thin crease 250 or other bend line set into the substrate material, as illustrated in FIG. 19. Hinge-like member 249 allows the center section 239 to fit around a patient's mouth and the right section 237 and the left section 241 to fit around a patient's face.

The apparatus can be applied by fitting a support to a patient. The support can comprise a head-set, intra-oral tray, a bite tab, one or more straps, one or more nose piece, one or more ear piece, or any other support or attachment mechanism. When the support has been fitted so that it can be repeatably worn by the patient one or more light sources can be attached to the support at locations where light from the light sources can illuminate a treatment area.

A treatment regimen can then be established. The physician, dentist, or therapist at her or his office or a patient at her or his home can optionally employ the apparatus in one or more methods of the invention.

Other embodiments, configurations, components, steps, or features can be incorporated in the invention. See, e.g., U.S. Patent Publication No. 2007/0248930 and U.S. Patent Publication No. 2006/0200212, which is hereby incorporated by reference in its entirety.

To calibrate light-therapy apparatus, a sensor useful for measuring reflectance (not shown) can be provided at a location that will be adjacent the skin of a patient when light-therapy apparatus is in the use position. The sensor can measure the reflectance of light from the skin of the patient, and if the value measured is outside a predetermined range (e.g. because light-therapy apparatus has been displaced from a patient's head), the sensor can automatically pause a treatment or the emission of light from light source. Pausing treatment or the emission of light if light-therapy apparatus is displaced from a patient's head can minimize the risk of accidental injury, e.g., due to exposure of a patient's eyes to light from light source.

In some embodiments, depending on a signal from the reflectance sensor, a controller can determine whether one or more light characteristic is to be maintained or adjusted (e.g., increased or decreased). Light characteristics can include, but are not limited to, light intensity, light wavelength, light coherency, light range, peak wavelength of emission, continuity, pulsing, duty cycle, frequency, duration, or whether a light emitter is on or off.

The light source can be configured to emit light that is substantially monochrome in some embodiments, although this is not mandatory. Providing light emitters that emit at multiple wavelengths allows for irradiation over multiple wavelengths for greater biological activity and greater selectivity and precision in administration. The light source can emit incoherent light, although this is not mandatory. In some examples, light can be provided at a single frequency, light can have a phase that drifts quickly, pulse of light waves can have an amplitude that changes quickly, or a light wave with a broad range of frequencies can be provided. The light can be administered continuously or pulsed at suitable frequencies and duty cycles. The light source can be configured to administer any of these light characteristics as described anywhere above.

In some embodiments a light source emits light that includes infrared light, and the light source also emits light that includes bright visible light. The bright visible light deters users from looking into light source 30 when it is operating, provides a perceptible indication that the apparatus is operating, and can be useful in properly positioning the light-therapy apparatus 20. The visible light can be, but is not necessarily, in a wavelength range that is beneficial for light therapy. In some embodiments, the ratio of the intensities of the visible and infrared components of the light is 1 part or less visible light to 5 parts or more infrared light. In some embodiments, a light source can comprise light emitters emitting light over a range of wavelengths. In some embodiments, the range can include wavelengths less than an order of magnitude. Alternatively, the range can include wavelengths emitted at one, two, three or more orders of magnitude.

Figure 6:
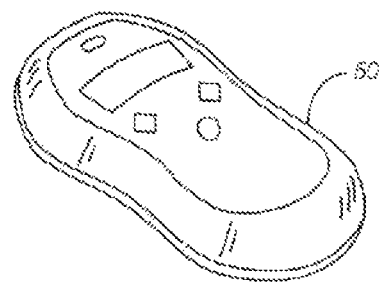
FIG. 6 is a top view of a programmable controller for use with a light-therapy apparatus.

FIG. 6 illustrates an example of a programmable controller 50 of a type that can be used to control the operation of light-therapy apparatus 20. Although controller 50 is described in this exemplary embodiment as being programmable, it is not necessary that controller 50 be programmable. For example, a controller can have controls that allow various parameters to be set, such as light wavelength, light intensity, light pulsing, light duty cycle, light frequency, or light duration, and can appropriately activate light emitters of one or more light sources 30 in response to an appropriate signal. A controller can control light emissions with any light characteristics, which can include those described anywhere above. Each of the light sources, e.g. light sources 30A-30H shown in FIG. 2, can be regulated independently by one or more controllers 50. A physician, dentist, orthodontist, therapist, technician or other professional can set those controls or program controller 50 so that an appropriate treatment is delivered when a patient initiates delivery of the treatment. Alternatively, the patient who is receiving the treatment might set controls. In some embodiments, the controls can include preset programs that can be suited to particular situations. In other embodiments, one or more parameter can be individually adjusted or entered.

In some embodiments, as shown in FIG. 6, a programmable controller can be a handheld device. Alternatively, the programmable controller can be part of another device or in communication with another device, such as a computer, which can include a personal computer, server computer, or laptop computer; personal digital assistants (PDAs) such as a Palm-based device or Windows CE device; phones such as cellular phones or location-aware portable phones (such as GPS); a roaming device, such as a network-connected roaming device; a wireless device such as a wireless email device or other device capable of communicating wireless with a computer network; or any other type of network device that can communicate over a network. Any description herein of computers or any other devices can apply to other devices, including controllers. A device can have a memory that can include tangible computer readable media that can include code, logic, instructions to perform any steps, calculations, algorithms, or execute programs or pre-stored instructions.

Programmable controller 50 can be a separate, remote unit or can be directly connected to or integrated with a light source 30. The programmable controller can connected to or integrated with any portion of the light-therapy apparatus, which can include a local controller, actuation mechanism, frame, or any other part of the controller.

A cable 52 can be provided to connect light-therapy apparatus 20 to programmable controller 50, a source of electricity for light source 30, or a suitable heating or cooling system. In some embodiments, wired communication can be provided between the programmable controller and the light-therapy apparatus. In other embodiments, the programmable controller and the light-therapy apparatus can communicate wirelessly. Examples of wireless signals can include, but are not limited to, radio-frequency (e.g., RFID) signals, bluetooth, or control-area-network (CAN) messages.

In some embodiments, controller 50 can comprise a microprocessor, data store, power supply, clock and associated electronic circuitry. A power source can include an external power source or an internal power source. For example, power can be provided by an electric plug. The plug might be in communication with a grid/utility, generator, or energy storage system. In some embodiments, the power source might be a renewable power source. The power source can be an energy storage system, such as a battery, ultracapacitor, or fuel cell. In some embodiments, the power source can be portable.

Control parameters are stored in the data store. A controller can comprise a memory that can include tangible computer readable media that can include code, logic, instructions to perform any steps, calculations, algorithms, or execute programs or pre-stored instructions. Programmable controller 50 operates light source 30 according to the parameters in the data store. The parameters can specify one or more of: treatment duration; wavelength or wavelengths of light emitted by light emitters 38; light intensity of particular wavelength or wavelength ranges during the treatment; whether light emitters 38 operate continuously or are pulsed; if light emitters 38 are pulsed, the rate at which light emitters 38 are pulsed; if light emitters 38 are pulsed, the duty cycle at which light emitters 38 are pulsed, light coherency of the light emitters 38, or any other light characteristic as described anywhere above. The light emitters within the same light source can have the same light parameters. Alternatively, there can be light emitters of different light parameters within the same light source.

If light-therapy apparatus 20 has sets of light emitters 38 having different characteristics (e.g. sets of LEDs that emit light at different wavelengths or sets of light sources 30 that illuminate selected tissues in different locations) then separate control parameters can be provided for different sets of the light emitters 38 or light sources 30. In some embodiments, different sets of parameters are specified for different segments (intervals) of a light treatment. For example, light therapy treatments can be defined for a set of intervals each lasting from a few seconds to a few hundred seconds or a fraction of an hour. Different parameters can be specified for each of the intervals. The intervals are not necessarily equal in length. In some embodiments, a clock of a controller can assist in determining whether a predefined time interval has passed.

In some embodiments, different sets of parameters can be specified for different areas of light-therapy apparatus 20. In some cases, some light sources 30 of light-therapy apparatus 20 can be turned off because the treatment plan for a patient does not require light of particular wavelength or light at all wavelengths to be administered at locations corresponding to those parts of the light-therapy apparatus 20. For example, with reference to FIG. 2, programmable controller 50 can be programmed such that only light sources 30A, 30B, 30C and 30D are activated for a particular treatment regime in which it is desired that light therapy be administered only to a patient's upper teeth. Alternatively, programmable controller 50 can be programmed such that only light sources 30A, 30D, 30E and 30H are activated for a particular treatment regime in which it is desired that light be administered only to a patient's molars. Various other combinations and permutations of the activation of various light sources disposed about light-therapy apparatus 20 in any suitable configuration can be devised and implemented, depending on the desired application. In some embodiments, light-therapy apparatus 20 is configured (i.e. light sources 30 are positioned and oriented) so as to provide substantially uniform illumination of substantially the entire maxillary and mandibular alveolar bone or teeth of a patient. The light-therapy apparatus can be configured to provide substantially uniform illumination to other regions of the patient. The regions can optionally be limited to alveolar bone or basal bone.

A physician, dentist, orthodontist, therapist, assistant, technician, or other professional can program a patient's treatment regimen into programmable controller 50. This can be done, for example, with the aid of suitable software running on a computer that is in data communication with programmable controller 50 or by way of a suitable user interface built into programmable controller 50. In some embodiments, programming a treatment regimen can include specifying desired values for one or more parameter of light treatment. Programming a treatment regimen can also include specifying timing associated with the one or more parameters of light treatment. For example, a treatment regimen can be programmed so that for the first several minutes, light is provided at a first wavelength, and for the next several minutes, light is provided at a second wavelength. In some embodiments, default values can be provided. A user can be able to adjust the default values to create a customized light treatment regimen. In other embodiments, no default values are provided and a user can enter different parameter values.

Programmable controller 50 can have one or more pre-set programs built in. As an alternative to, or as an aid to programming controller 50, the physician, dentist, orthodontist, therapist or other professional can select a pre-set program that is appropriate for controlling light-therapy apparatus 20 to administer light to a patient. Such pre-set programs can be provided for particular types or stages of orthodontic treatment. In some embodiments, a pre-set program can be selected, and a user can modify the pre-set program as desired. For example, a user can be able to deviate from a pre-set program by adjusting any of the following: timing, light wavelength, light intensity, light pulsing or continuous, light duty cycle, light frequency, which lights are on or off, location of light source, or any other parameter that is described elsewhere herein.

In some embodiments, a program can be determined prior to using the light-therapy apparatus. For example, after a user has created or selected a program, the light-therapy apparatus can be used, and one or more light source can emit light. In some embodiments, once a program is being implemented or a light-therapy apparatus is in use, the light treatment regimen is not to be altered. In other embodiments, a light treatment regimen can be altered while the light-therapy apparatus is in use. For example, while light is being emitted, the light intensity can be adjusted, the light pulsing or continuous characteristics, the light wavelength, light selection, or location of the light source relative to a patient's face can be adjusted. The treatment regimen can be adjusted via the controller or a device in communication with the controller. In some embodiments, a patient wearing a light-therapy apparatus can adjust the treatment regimen. In other embodiments, physician, dentist, orthodontist, therapist, technician, assistant, or other professional can adjust the treatment regimen.

A user can interact with a user interface to program a controller, select a program or adjust a value of a program. Any user interface known in the art can be utilized. For example, a programmable controller can include one or more button, pointing device (e.g., mouse, joystick, trackball), keyboard, switch, knob, dial, touchscreen, or video display. The user interface can be provided to the controller directly, or can be provided to a device (e.g., computer) that can be in communication with the controller. A controller can include a display that can provide information to the user about selected parameters, timing or pre-set programs.

Programmable controller 50 can maintain a log of treatments that have been administered. For example, controller 50 can log the date and time that each treatment was initiated, the duration of the treatment, and whether or not the treatment was completed. The date and time can be logged based on a clock associated with the programmable controller. One or more timestamp can be provided indicating timing. The log can indicate parameters associated with the treatment. The log can be stored within a memory of the programmable controller. Alternatively, the log can be stored within a memory of a device in communication with the programmable controller, such as a computer.

The log can be accessed by a user to view log data. In one embodiment, the log can be accessed by a dentist, physician, orthodontist, technician, or patient who uses the light-therapy apparatus. A user can access the log directly from a controller or a device in communication with the controller. A user can access the log from any device that can be in communication with a device that stores the log data. The controller or devices can communicate directly with one another or over a network. The network can include a local area network, or a wide area network, such as the Internet.

This log can be subsequently reviewed by a dentist, physician, orthodontist or other medical professional to evaluate whether or not the patient has complied with a prescribed treatment regimen. The log can be displayed to a screen or other video display of a device. The log can track the times and durations of light therapy treatments administered by light-therapy apparatus 20 and can also track other features such as operating temperatures, operational status, treatment parameters, timing, or any combination thereof.

In some embodiments, a programmable controller 50 has a button or other suitable user patient interface that allows a patient to initiate a treatment according to previously-set parameters in the data store. In some embodiments, the patient interface is very simple such that minimal instruction is required to explain to a patient how to use light-therapy apparatus 20. Programmable controller 50 can include an audible or visual indicator that generates a signal to remind a patient that it is time for a treatment (or that a scheduled treatment is overdue).

In some embodiments, a treatment regimen can be pre-selected or programmed at the same device (e.g., controller, computer) through which a patient can initiate a treatment. Alternatively, a treatment regimen can be pre-selected or programmed at a different device (e.g., controller, computer) through which a patient can initiate a treatment. In some embodiments, communications can be provided between the controller and another device (e.g., computer) that can allow one or more treatment program to be delivered to the controller. In some embodiments, two-way communications can be provided between the controller and another device. In other embodiments, one-way communications can be provided from the other device to the controller or vice versa.

A patient can use light-therapy apparatus 20 at home or in another location by operating programmable controller 50 to initiate delivery of a treatment. The patient can use the light-therapy apparatus while at an appointment with a medical professional, or at a laboratory or clinic. Alternatively, a patient can use this apparatus while not at an appointment with a medical professional, or at a laboratory or clinic. The patient can use this apparatus while the patient is mobile or traveling.

Programmable controller 50 can comprise circuitry that monitors temperature at one or more locations in light source 30. The circuitry can monitor a signal modulated by a temperature sensor in light source 30. In some embodiments, the temperature sensor can be a thermocouple, thermistor, or resistance temperature sensor (RTD). In other embodiments, programmable controller 50 can monitor e.g. the current and voltage driving light emitters (e.g., LEDs, lasers) in light source 30. The current/voltage relationship can be temperature-dependent. Thus, by monitoring the current/voltage relationship programmable controller 50 can determine whether the light emitter (e.g., LED, laser) is at an undesirably high temperature. A temperature sensor can also be used to determine whether a light source or light assembly, or any component thereof is at an undesirably high temperature. Furthermore, the temperature sensor can determine whether a light emitter, light source, or light assembly has an undesirably low temperature. A temperature sensor can be used to determine whether any part of a light-therapy apparatus falls within a desired temperature range.

Programmable controller 50 can shut off or reduce current to any particular light source (e.g. one or more of light sources 30A-30H) when it detects that the temperature of that light source is undesirably high (or is trending towards being undesirably high). The programmable controller can also shut off or reduce current to any particular light emitter (e.g., one or more light emitter can be provided for a light source) if the controller detects that the temperature at that light emitter is undesirably high. Alternatively, the programmable controller can shut off or reduce current to a group or subgroups of light emitters or light sources if the temperature of a particular light emitter or light source is too high. For example, the programmable controller can shut off or reduce current to all light sources if a temperature is too high.

If light-therapy apparatus 20 is provided with a cooling apparatus, controller 50 can increase the operation of the cooling apparatus when it detects that the temperature of light source 30 is above a desired level. If increasing operation of the cooling apparatus does not bring the temperature of a light source or light emitter or any other portion of a light-therapy apparatus to a desired level, one or more light emitters or light sources can be shut off or reduced.

Shut-off or current reducing steps can occur automatically when a temperature threshold is reached. In some embodiments, a user can define the temperature threshold. In other embodiments the temperature threshold can be pre-set. In some embodiments, an alarm or alert can be provided when a temperature threshold is reached, and a user can manually shut off or reduce current to a light source or light emitter. In some embodiments, a temperature measurement can be displayed to a user.

Another aspect of the invention further provides for a light therapy kit comprising a light-therapy apparatus as described herein and instructions for use in the present methods. The kit can further comprise a light source that is separate from the light-therapy apparatus. The light sources can be disposable, so that they can be easily replaced after a given amount of use. In some embodiments, a light-therapy apparatus and light sources can be individually packaged or can be packaged together.

The kit can also comprise a programmable controller as described herein. The kit can further comprise any components useful for the controller to operate. For example, the kit can comprise a component to power the controller or light-therapy apparatus. The kit can also comprise a component that allows the controller to operably connect with a light-therapy apparatus.

The kit can also comprise software, an algorithm, or a set of computer readable media that can provide instructions to a controller. The software, algorithm, or set of computer readable media can be provided on a memory medium. The memory medium can be a removable or portable, such as a CD, USB flash drive, or external hard drive.

The kit can be conveniently packaged and can be commercially available. The kit can also include written instructions for use or maintenance of items therein.

In use, a physician, dentist, orthodontist, therapist or other professional can program a patient's prescribed treatment regimen into a programmable controller 50 (see FIG. 6, for example). Programmable controller 50 controls parameters of a light therapy treatment to be administered by light-therapy apparatus 20. For example, controller 50 can control the duration of the treatment, wavelength or wavelengths of light administered, light intensity, pulse frequency, or any other light or treatment characteristics. Programmable controller 50 runs a patient's prescribed treatment regimen causing the at least one light source 30 to emit pulsed or continuous light of specified wavelengths according to the prescribed parameters onto the treatment area of a patient's maxillary or mandibular alveolar bone. The treatment area can include any other regions described elsewhere herein. This can include alveolar bone, basal bone, or teeth. Light can be administered mostly only to the treatment area. Light-therapy apparatus 20 can provide effective, stabilized repeatable, accurate, programmable, and consistent light therapy for a desired treatment to specifically administer light of a desired wavelength or wavelengths to a particular treatment region at a substantially uniform intensity. Scattering of light as it enters a patient's soft tissues can also cause the beam of light to diverge, resulting in uniform illumination of the patient's soft or hard tissue.

In accordance with another aspect of the invention, a light-therapy apparatus can be used in a method of administering light to a region of a patient's oral tissue. The method can include providing a light-therapy apparatus comprising a support sized and shaped to engage with features of the patient's face and one or more light source supported by the support, engaging the support with one or more features of the patient's face, determining whether the position of one or more light source needs to be adjusted in order to administer a desired intensity of light to the region, depending on said determination, varying or maintaining the position of the one or more light source, and administering light to the region.

The light-therapy apparatus can optionally be an apparatus as described in any of the embodiments anywhere above. The light-therapy apparatus can include a support that can be engaged with one or more features of the patient's face. For example, the light-therapy apparatus can engage with features of a patient's face by conforming to the shape of the feature, wrapping around the feature, overlying the feature, grasping the feature, adhering to the feature or providing pressure or weight to the feature. For example, the light-therapy apparatus can include an ear-engaging portion that can wrap around the back of the patient's ear. In another embodiment, the light-therapy apparatus can include a nose-engaging portion that can rest on the bridge of the patient's nose.

A method for administering light to a region can also include determining whether the position of one or more light source needs to be adjusted in order to administer a desired intensity of light to the region. Such determination can be made manually or automatically. For example, the patient or a medical professional can determine the position of a light source when the light-therapy apparatus is worn. The patient or medical professional can determine the relative position of the light source to a desired region. The light-therapy apparatus comprises one or more sensor. In some embodiments, the sensor can be a temperature sensor or a reflectance sensor. In another embodiment, a sensor can determine the relative position of the light source with respect to the region. Determining whether a light characteristic needs to be adjusted in order to administer a desired light to the region can be based on one or more signal from the one or more sensor.

Depending on said determination, the position of the one or more light source can be varied or maintained. The position of the light can be varied manually or automatically.

For example, a patient or medical professional can manually move a light source. In another embodiment, one or more actuator can be provided in communication with a controller. The controller can provide one or more signal to the actuator, thereby causing the actuator to move or maintain its position. The light source can be displaced, rotated, or tilted to provide a desired intensity of light to a region. In some instances, the light source can be pressed against the patient's face above the region, and the position of the light source can be set to that location. In some embodiments, after the position of a light source is adjusted, the light source can remain at that position in the absence of any outside force. In some embodiments, a light source can be locked into a position after it is adjusted, so that the light source can remain in that position even if a force is exerted on it.

In some embodiments, after a light has been set to a desired position, the method can include administering light to the region. In some other embodiments, light can be administered before or while the light is being set to a desired position. In some embodiments, a light-therapy apparatus can be engaged with the patient, the light source can be positioned, and the light can be administered without removing the light-therapy apparatus from the patient. In some embodiments, the light-therapy apparatus can be engaged with the patient, the light source can be positioned, and the light-therapy apparatus can be removed from the patient. This can be a series of steps for fitting the light-therapy apparatus to the patient. The light-therapy apparatus can subsequently be re-engaged with the patient and light can be administered to the patient. This can include steps for administering the light to the patient, after fitting the light-therapy apparatus to the patient. The light sources can already be positioned to administer light to the region. In some instances, light can be administered to the patient on multiple occasions following a single fitting.

In some embodiments, the method can include varying the position of one or more light source by adjusting the position of the light along the length of the support. The method the method can also include varying the position of one or more light by rotating the light source about an axis. The axis can be vertical, horizontal, or provided at any other orientation.

In some embodiments, light therapy apparatuses may be provided which are particularly suitable for intra-oral administration of light to one or more regions within a patient's oral cavity or mouth, such as a region of the patient's maxillary or mandibular alveolar bone. An intra-oral light therapy apparatus may incorporate one or more features or components of one or more embodiment of a light source or light therapy apparatus described herein. In one embodiment an intra-oral light therapy apparatus irradiates light having one or more characteristics of light described above.

Examples of intra-oral light therapy devices can include a laser beam delivered by an optical fiber to a point of irradiation. In one embodiment, a low-energy laser source, such as a gallium-aluminum-arsenide laser can be used. See, e.g., Kawasaki, et al., "Effects of Low-Energy Laser Irradiation on Bone Remodeling During Experimental Tooth Movement in Rats," Lasers in Surgery and Medicine 26:282-291 (2000); Cruz, et al., "Effects of Low-Intensity Laser Therapy on the Orthodontic Movement Velocity of Human Teeth: A Preliminary Study," Lasers in Surgery and Medicine 35: 117-120 (2004); Abi-Ramia, et al., "Effects of Low-Level Laser Therapy and Orthodontic Tooth Movement on Dental Pulp in Rats," Angle Orthodontist, 80(1): 116-122 (2010), which are hereby incorporated by reference in their entirety.

Other examples of intra-oral light therapy devices can include an oral tray that fits over one or more tooth or gums. In another embodiment, an oral tray need not fit over one or more tooth, but may be contoured to fit within a patient's oral cavity. Light from a light source can be transmitted to one or more teeth, or gum or mucosal tissue overlying one or more tooth root, via the oral tray. In some embodiments, the tray reflects or conveys light from a natural source (e.g., sun) or man-made source (e.g., lasers, LEDs, or light sources having any of the characteristics previously mentioned). In some embodiments, a light source is embedded within the tray or attached to the tray. In other embodiments, the intra-oral therapy devices include a cap-like structure that can fit over one or more tooth, or gum or mucosal tissue overlying one or more tooth root. The cap-light structure can transmit light from a distal light source. Alternatively, the cap-like structure comprises a light source provided therein. In some embodiments, the intra-oral light therapy devices are handheld devices that can provide or direct light to one or more tooth, or gum or mucosal tissue overlying one or more tooth root. The light can be provided from a proximal or distal light source. In some embodiments, the handheld devices comprise or otherwise utilize fiberoptics. The light-providing portion of the handheld device can be held adjacent to a tooth, gums, or mucosal tissue overlying a tooth root. In some instances, the light providing portion of the handheld device can be located within a patient's oral cavity. See, e.g., U.S. Pat. No. 2,884,926; U.S. Patent Publication No. 2008/0255498; U.S. Patent Application No. 2006/0085052; U.S. Patent Publication No. 2008/0032252, which are hereby incorporated by reference in their entirety.

In some embodiments, a light therapy apparatus as described above is useful for administering light intra-orally. Thus, a light therapy apparatus can be configured to provide light extra-orally or intra-orally or both. An intra-oral light therapy apparatus may be used in conjunction with an extra-oral light therapy apparatus as described above.

Example

The invention is further described with reference to the following specific examples, which are not meant to limit the invention, but rather to further illustrate it.

A patient presents with an upper right first and second molar that have drifted forward due to a congenitally missing second bicuspid. The patient would benefit from having her teeth distalized. While a temporary orthodontic device (TAD) anchorage with an implant could be used to exert force to retract these teeth, heavy forces, without more, can cause the implant to fail prematurely.

The implant is installed, and light having a wavelength of about 850 nm and intensity of 70 mW/cm$^2$ is administered to the implant and to the mandibular and maxillary alveolar bone surrounding the first and second molars only. The teeth and implant are pretreated with light for 10 minutes immediately prior to the activation of the TAD anchorage appliance, which administers a force of about 300 grams to the teeth (about 150 grams of force exerted per tooth). Light treatment occurs for an additional 10 minutes immediately following the activation of the appliance. Light is administered daily for about 20 minutes for about 2-3 weeks following the activation of the appliance. It is believed that not only would the two teeth be distalized, but the administration of light would prevent the loosening and resorption of the bone around the TAD. The heavy forces would allow the 2 molars to distalize without the risk of causing resorption of the teeth roots as well as counter the occlusal forces that tend to prevent distalizing of posterior teeth.

While particular embodiments of the present invention have been shown and described herein, such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

The invention claimed is:

1. An intra-oral light therapy system, comprising:
   an oral tray configured to fit within an oral cavity of a patient;
   a plurality of emitters embedded within the oral tray and configured to overlie and irradiate mucosal tissue overlying a root of a tooth of the patient with light when in use in the oral cavity;
   a reference sensor for sensing the light; and
   a controller comprising instructions to irradiate the root of the tooth of the patient using a plurality of emitters by controlling the plurality of emitters to emit light at a wavelength ranging from 620 nm to 1,000 nm and an intensity ranging from about 1 mW/cm$^2$ to about 100 mW/cm$^2$, wherein the controller is adapted to control the plurality of emitters according to a treatment regimen and a signal sensed by the reference sensor.

2. The intra-oral light therapy system of claim 1, wherein each emitter includes at least one light-emitting diode (LED).

3. The intra-oral light therapy system of claim 1, wherein the oral tray is adapted to exert an orthodontic force on the tooth.

4. The intra-oral light therapy system of claim 1, wherein the intra-oral light therapy system is adapted to couple to an extra-oral light source.

5. The intra-oral light therapy system of claim 4, wherein the intra-oral light therapy system is adapted to couple to the extra oral light source via a removable extra-oral bridge coupled to the oral tray.

6. The intra-oral light therapy system of claim 1, wherein the intra-oral light therapy system comprises the reference sensor and the instructions of the controller are adapted to maintain or adjust a characteristic of the light based upon the signal sensed by the reference sensor.

7. The intra-oral light therapy system of claim 6, wherein the characteristic is one of the wavelength, the intensity, coherency, range, peak wavelength of emission, continuity, pulse, duty cycle, frequency or duration.

8. An intra-oral light therapy system, comprising:
   an oral tray configured to fit within an oral cavity of a patient;
   a plurality of emitters embedded within the oral tray and configured to overlie and irradiate mucosal tissue overlying one or more roots of a plurality of teeth of the patient when in use in the oral cavity, wherein each of the plurality of emitters is configured to emit light having a wavelength ranging from 620 nm to 1,000 nm and an intensity ranging from about 50 mW/cm$^2$ to about 200 mW/cm$^2$;
   a reference sensor for sensing the light; and
   a controller comprising instructions to control the plurality of emitters according to a treatment regimen in response to the patient initiating a treatment session, wherein the controller is adapted to control the plurality of emitters according to the treatment regimen and a signal sensed by the reference sensor.

9. The intra-oral light therapy system of claim 8, wherein the oral tray is adapted to exert an orthodontic force on the tooth.

10. The intra-oral light therapy system of claim 8, wherein the treatment regimen comprises emitting light on only a portion of the plurality of teeth of the patient.

11. The intra-oral light therapy system of claim 8, wherein the intra-oral light therapy system is adapted to couple to an extra-oral light source.

12. The intra-oral light therapy system of claim 11, wherein the controller is adapted to activate the extra-oral light source according to the treatment regimen.

13. The intra-oral light therapy system of claim 8, wherein the intra-oral light therapy system comprises the reference sensor and the instructions of the controller are adapted to maintain or adjust a characteristic of the light based upon the signal sensed by the reference sensor.

14. An intra-oral light therapy system, comprising:
   an oral tray configured to fit within an oral cavity of a patient and exert an orthodontic force on a tooth;
   a plurality of emitters embedded within the oral tray and configured to overlie and irradiate mucosal tissue overlying a root of a tooth of the patient with light when in use in the oral cavity; and
   a controller comprising instructions to irradiate the root of the tooth of the patient using the emitter by controlling the plurality of emitters to emit light at a wavelength ranging from 620 nm to 1,000 nm and an intensity ranging from about 1 mW/cm2 to about 100 mW/cm2.

15. The intra-oral light therapy system of claim 14, wherein each emitter includes at least one light-emitting diode (LED).

16. The intra-oral light therapy system of claim 14, wherein the intra-oral light therapy system is adapted to couple to an extra-oral light source.

17. The intra-oral light therapy system of claim 16, wherein the intra-oral light therapy system is adapted to couple to the extra oral light source via a removable extra-oral bridge coupled to the oral tray.

18. The intra-oral light therapy system of claim 14, wherein the intra-oral light therapy system comprises a reference sensor and the instructions of the controller are adapted to maintain or adjust a characteristic of the light based upon a signal sensed by the reference sensor.

19. The intra-oral light therapy system of claim 18, wherein the characteristic is one of the wavelength, the intensity, coherency, range, peak wavelength of emission, continuity, pulse, duty cycle, frequency or duration.

20. An intra-oral light therapy system, comprising:
   an oral tray configured to fit within an oral cavity of a patient and exert an orthodontic force on a tooth;
   a plurality of emitters embedded within the oral tray and configured to overlie and irradiate mucosal tissue overlying one or more roots of a plurality of teeth of the patient when in use in the oral cavity, wherein each of the plurality of emitters is configured to emit light having a wavelength ranging from 620 nm to 1,000 nm and an intensity ranging from about 50 mW/cm2 to about 200 mW/cm2; and a controller comprising instructions to control the plurality of emitters according to a treatment regimen in response to the patient initiating a treatment session.

21. The intra-oral light therapy system of claim 20, wherein the treatment regimen comprises emitting light on only a portion of the plurality of teeth of the patient.

22. The intra-oral light therapy system of claim 20, wherein the intra-oral light therapy system is adapted to couple to an extra-oral light source.

23. The intra-oral light therapy system of claim 22, wherein the controller is adapted to activate the extra-oral light source according to the treatment regimen.

24. The intra-oral light therapy system of claim 20, wherein the intra-oral light therapy system comprises a reference sensor and the instructions of the controller are adapted to maintain or adjust a characteristic of the light based upon a signal sensed by the reference sensor.

25. The intra-oral light therapy system of claim 24, wherein the controller is adapted to control the plurality of emitters according to the treatment regimen and the signal sensed by the reference sensor.

* * * * *